(12) United States Patent
Shu et al.

(10) Patent No.: US 7,223,902 B1
(45) Date of Patent: May 29, 2007

(54) **METHOD OF PRODUCING RECOMBINANT *ASPERGILLUS NIGER* β-GLUCOSIDASE AND AN AROMA SPREADING PLANT**

(75) Inventors: Wei Shu, Rehovot (IL); Ira Marton, Rehovot (IL); Daniel L. Siegel, Rehovot (IL); Bravdo Ben-Ami, Rehovot (IL); Mara Dekel, Rehovot (IL); Oded Shoseyov, Karme Yossef (IL)

(73) Assignee: Yissum Research Development Company of the Hebrew University of Jerusalem, Jerusalem (IL)

(*) Notice: Subject to any disclaimer, the term of this patent is extended or adjusted under 35 U.S.C. 154(b) by 295 days.

(21) Appl. No.: 10/130,150

(22) PCT Filed: Nov. 15, 2000

(86) PCT No.: PCT/IL00/00758

§ 371 (c)(1),
(2), (4) Date: May 16, 2002

(87) PCT Pub. No.: WO01/36586

PCT Pub. Date: May 25, 2001

Related U.S. Application Data

(63) Continuation of application No. 09/443,338, filed on Nov. 19, 1999, now abandoned.

(51) Int. Cl.
*C12N 15/82* (2006.01)

(52) U.S. Cl. ...................... 800/288; 800/287
(58) Field of Classification Search ................ 800/284, 800/278; 435/320.1, 69.1, 209, 468, 69.8
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell et al. |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,879,219 A | 11/1989 | Wands et al. |
| 5,011,771 A | 4/1991 | Bellet et al. |
| 5,281,521 A | 1/1994 | Trojanowski et al. |
| 5,316,931 A | 5/1994 | Donson et al. |
| 5,863,783 A | 1/1999 | Van Heuvel et al. |
| 5,997,913 A | 12/1999 | Fowler et al. |
| 6,015,703 A | 1/2000 | White et al. |

FOREIGN PATENT DOCUMENTS

EP        0307071     *  3/1989

OTHER PUBLICATIONS

Goodall GJ and Filipowicz W. The minimum functional length of pre-mRNA introns in monocots and dicots. (1990) PMB vol. 14, pp. 727-733.*
Iwashita *Apsergillus kawachii* DNA for beta-D-glucosidase, complete cds. (1999) GenBank Accession AB003470.*
Dan s, Marton I, Dekel M. Bravdo B-A, He S, Withers SG, and Shoseyov O. Cloning, Expression, Characterization and Nucleophile Identification of Family 3, *Aspergillus niger* beta-Glucosidase. (2000) JBC vol. 275, pp. 4973-4980.*
Vaquero C, Sack M, Chandler J, Drossard J, Schuster F, Monecke M, Schillberg S, and Rischer R. Transient expression of a tumore-specific single-chain fragment and a chimeric antibody in tobacco leaves. (1999) PNAS vol. 96, pp. 11128-11133.*
Leah R, Kigel J, Svendsen I, and Mundy J. Biochemical and Molecular Characterization of a Barley Seed beta-Glucosidase. (1995) JBC vol. 270, pp. 15789-15797.*
Bovy AG, Angenent GC, Dons HJM, and van Altworst A-C. Heterologous expression of the Arabidopsis etr1-1 allele inhibits the senescence of carnation flowers. (1999) Molecular Breeding vol. 5, pp. 301-308.*
Le Traon-Masson et al, "Purification and Characterization of two β-D-glucosidases from an *Aspergillus niger* enzyme preparation: affinity and specificity toward glucosylated compounds characteristics of the processing of fruits", (1998) Enz. Micro. Technol., 22 (5) 374-382.
Penttila et al, "Cloning of *Aspergillus niger* Genes in Yeast. Expression of the Gene Coding *Aspergillus* Beta-Glucosidase", Mol. Gen. Genet. 194, 494-499, 1984.
Dekker R.F.H., "Kinetic, Inhibition, and Stability Properties of a Commercial Beta-D Glucosiade Cellobiase Preparation from *Aspergillus-niger* and its Suitability in the Hydrolysis of Lignocellulose", Biotechnology and Bioengineering, vol. 28, No. 9, 1986, pp. 1438-1442, XP002000249, ISSN: 0006-3592, *the whole document*.

(Continued)

*Primary Examiner*—Ashwin D. Mehta
*Assistant Examiner*—Cathy Kingdon Worley

(57) ABSTRACT

The invention provides a method of producing a recombinant polypeptide having β-glucosidase enzymatic activity, a polynucleotide encoding the polypeptide, nucleic acid constructs carrying the polynucleotide, transformed cells, such as yeast cells, and transgenic organisms expressing the polynucleotide. The invention provides various uses of the polypeptide, the polynucleotide, cells and/or organisms, including producing a recombinant polypeptide having β-glucosidase enzymatic activity, increasing the level of aromatic compounds in alcoholic beverages, as well as other fermentation products of plant material, hydrolyzing cellobiose and thus increasing the level of fermentable glucose, increasing the production of alcohol; such as ethanol from plant material, increasing the aroma released from a plant, or a plant, product, and hydrolysis or transglycosylation of glycosides.

7 Claims, 12 Drawing Sheets

OTHER PUBLICATIONS

Zhou s. et al; "Engineering Endoglucanase-secreting Strains of Ethanologenic Klebsiella Oxytoca P2." Journal of Industrial Microbiology & Biotechnology, vol. 22, No. 6, Jun. 1999, pp. 600-607, XP000971439, ISSN: 1367-5435, *the whole document*.

Shoseyov O. et al. "Immobilized endo-beta-glucosidase enriches flavour of wine and passion fruit juice" Journal of Agricultural and Food Chemistry, vol. 38, No. 6, 1990, pp. 1387-1390, XP001122152, ISSN: 0021-8561, *the whole document*.

Iwashita Kazuhiro et al. "The bg1A gene of *Aspergillus kawachii* encodes both extracellular and cell wall-bound beta-glocosidases", applied and envrionmental Microbiology, vol. 65, No. 12, Dec. 1999, pp. 5546-5553, XP002228145, ISSN: 0099-2240, *figure 3*.

Siegel et al., -& Database EMBL (online), Feb. 18, 2000, retrieved from EBI, database accession No. AJ132386, XP002228148.

Bhat M.K. et al. "Cellulose Degrading Enzymes and Their Potential Industrial Applications." Biotechnology Advances, vol. 15, No. 3-4, 1997, pp. 583-620, XP004089630, ISSN: 0734-9750, p. 604, paragraph 3.

Iwashita et al. database access. No. AB003470.

Kawaguchi et al. database access. No. P48825.

Iwashita et al. database access. No. BAA19913.

Shoseyov et al, "Endo-β-Glucosidase from *Aspergillus Niger* Grown on a Monoterpine Glycoside Containing Medium", (1988), Phytochem. 27(7), 1973-1976.

Yeoh, et al, "Kinetic Properties of β-glucosidase from *Aspergillus ornatus*", (1986), Appl. Microbiol. Biotechnol. 25, 25-28.

Zarevucka et al, "A Chemoenzymatic Synthesis of the O-Glycosides", (1998) Chirality 10, 676-68.

Yi et al, "A novel approach to biotransformations in aqueous-organic two-phase systems: enzymatic synthesis of alkyl beta-[D]-glucosides using microencapsulated beta-glucosidase", Biotechnol Bioeng. Nov. 5, 1998;60(3):385-90.

Henrissat et al, "Updating the sequence-based classification of glycosyl hydrolases", Biochem J. Jun. 1, 1996;316 (Pt 2):695-6.

Hrmova et al, Barley beta-D-glucan exohydrolases with beta-D-glucosidase activity. Purification, characterization, and determination of primary structure from a cDNA clone, J Biol Chem. Mar. 1, 1996;271(9):5277-86.*

Y. Gueguen, et al. "A Very Efficient Beta-Glucosidase Catalyst for the Hydrolysis of Flavor Precursors of Wines and Fruit Juices", J. Agric. Food chem. 44:2336-2340, 1996.*

Shoseyov et al, Immobilized Endo-β-glucosidase Rnriches Flavor of Wine and Passion Fruit Juice, (1990), J. Agric. Food. Chem. 39, 1387-1390.*

Prade et al, "Enzymatic sysnthesis of disaccharides using *Agrobacterium* sp. B-glucosidase", (1998) Carbohyd. Res. 305, 371-381.*

Watanabe et al, "Purification and Properties of *Aspergillus niger* β-glucosidase", (1992), Eur. J. Biochem. 209, 651-659.*

Wong et al, "Identification of Glu-540 as the catalytic nucleophile of human beta-glucuronidase using electrospray mass spectrometry", J Biol Chem. Dec. 18, 1998;273(51):34057-62.*

Clark et al,, "Qualitative and quantative analysis of flavor additives on tobacco products using SPME-GC-Mass Spectroscopy". J. Aagric. Food Chem. 45 (3), 844-849, 1997.*

Shana et al, "Cloning and Characterization of Elongation Specific endo-1,4-β-glucanase (cell) from *Arabidopsis thaliana*", Plant Mol. Biol., 34:837-842, 1997.*

Parodi, AJ, "Role of N-oligosaccharide endoplasmic reticulum processing reactions in glycoprotein folding and degradation", Biochem J., May 15, 2000;348 Pt 1:1-13.*

* cited by examiner

```
  1  TCCATTCGCCCATGCTTAGCGTGTCTTTTCTTTGAACACTGCATGCGGGACTGTGAATTG   60
 61  CATGAGTGGGTAGCTTTGCGGAGACAGCTGCACTGGCATACATCATCGTTGGGTTCCTCA  120
121  ATTCGCATGCCGTGGCGGACGGTCACTTTGTGGCGCTCAAACTATTTAATATGGCCCAGC  180
181  TCCCCTTTCTCTCGCTGTTTTCGTTTCTGTCCTCCCTAAACCTCCAGTCTCTCCATTGGA  240
241  CAGGTGTTGCACGGTTGCTCACCTGGTTTGTTTTGCTCCCCCTTTGGGCGACCTTGCCAT  300
301  CATGAGGTTCACTTTGATCGAGGCGGTGGCTCTGACTGCCGTCTCGCTGGCCAGCGCTGT  360
     MetArgPheThrLeuIleGluAlaValAlaLeuThrAlaValSerLeuAlaSerAla
                            Signal Peptide
361  ACGTGCCGTTACTTTGTCCTGAGAATTGCAATTGTGCTTAATTAGATTCATTTGTTTGTT  420
                              Intron#1
421  TCATCATCGCTGACAATGGTCTTTTCATAGGATGAATTGGCCTACTCCCCACCGTATTAC  480
                                     AspGluLeuAlaTyrSerProProTyrTyr
481  CCATCCCCTTGGGCCAATGGCCAGGGCGACTGGGCGCAGGCATACCAGCGCGCTGTTGAT  540
     ProSerProTrpAlaAsnGlyGlnGlyAspTrpAlaGlnAlaTyrGlnArgAlaValAsp
541  ATTGTCTCGCAAATGACATTGGATGAGAAGGTCAATCTGACCACAGGAACTGGGTAGGGC  600
     IleValSerGlnMetThrLeuAspGluLysValAsnLeuThrThrGlyThrGly
601  TTACATGGCGCAATCTGTATGCTCCGGCTAACAACTTCTACATGGGAATTGGAACTATGT  660
                  Intron#2                       TrpGluLeuGluLeuCys
661  GTTGGTCAGACTGGCGGTGTTCCCCGGTAGGTTTGAAAATATTGTCGAGACAGGGGACAT  720
     ValGlyGlnThrGlyGlyValProArg          Intron#3
721  TATTGATTAACGGTGACAGATTGGGAGTTCCGGGAATGTGTTTACAGGATAGCCCTCTGG  780
                        LeuGlyValProGlyMetCysLeuGlnAspSerProLeuG
781  GCGTTCGCGACTGTAAGCCATCTGCTGTTGTTAGGCTTCGATGCTCTTACTGACACGGCG  840
     lyValArgAspS                           Intron#4
841  CAGCCGACTACAACTCTGCTTTCCCTGCCGGCATGAACGTGGCTGCAACCTGGGACAAGA  900
       erAspTyrAsnSerAlaPheProAlaGlyMetAsnValAlaAlaThrTrpAspLysA
901  ATCTGGCATACCTTCGCGGCAAGGCTATGGGTCAGGAATTTAGTGACAAGGGTGCCGATA  960
     snLeuAlaTyrLeuArgGlyLysAlaMetGlyGlnGluPheSerAspLysGlyAlaAspI
961  TCCAATTGGGTCCAGCTGCCGGCCCTCTCGGTAGAAGTCCCGACGGTGGTCGTAACTGGG 1020
     leGlnLeuGlyProAlaAlaGlyProLeuGlyArgSerProAspGlyGlyArgAsnTrpG
1021 AGGGCTTCTCCCCAGACCCTGCCCTAAGTGGTGTGCTCTTTGCCGAGACCATCAAGGGTA 1080
     luGlyPheSerProAspProAlaLeuSerGlyValLeuPheAlaGluThrIleLysGlyI
1081 TCCAAGATGCTGGTGTGGTTGCGACGGCTAAGCACTACATTGCTTACGAGCAAGAGCATT 1140
     leGlnAspAlaGlyValValAlaThrAlaLysHisTyrIleAlaTyrGluGlnGluHisP
1141 TCCGTCAGGCGCCTGAAGCCCAAGGTTTTGGATTTAATATTTCCGAGAGTGGAAGTGCGA 1200
     heArgGlnAlaProGluAlaGlnGlyPheGlyPheAsnIleSerGluSerGlySerAlaA
1201 ACCTCGACGATAAGACTATGCACGAGCTGTACCTCTGGCCCTTCGCGGATGCCATCCGTG 1260
     snLeuAspAspLysThrMetHisGluLeuTyrLeuTrpProPheAlaAspAlaIleArgA
1261 CAGGTGCTGGCGCTGTGATGTGCTCCTACAACCAGATCAACAACAGTTATGGCTGCCAGA 1320
     laGlyAlaGlyAlaValMetCysSerTyrAsnGlnIleAsnAsnSerTyrGlyCysGlnA
1321 ACAGCTACACTCTGAACAAGCTGCTCAAGGCCGAGCTGGGCTTCCAGGGCTTTGTCATGA 1380
     snSerTyrThrLeuAsnLysLeuLeuLysAlaGluLeuGlyPheGlnGlyPheValMetS
```

Fig. 5a

```
1381  GTGATTGGGCTGCTCACCATGCTGGTGTGAGTGGTGCTTTCGCAGGATTGGATATGTCTA  1440
      erAspTrpAlaAlaHisHisAlaGlyValSerGlyAlaLeuAlaGlyLeuAspMetSerM

1441  TGCCAGGAGACGTCGACTACGACAGTGGTACGTCTTACTGGGGTACAAACTTGACCATTA  1500
      etProGlyAspValAspTyrAspSerGlyThrSerTyrTrpGlyThrAsnLeuThrIleS

1501  GCGTGCTCAACGGAACGGTGCCCCAATGGCGTGTTGATGACATGGCTGTCCGCATCATGG  1560
      erValLeuAsnGlyThrValProGlnTrpArgValAspAspMetAlaValArgIleMetA

1561  CCGCCTACTACAAGGTCGGCCGTGACCGTCTGTGGACTCCTCCCAACTTCAGCTCATGGA  1620
      laAlaTyrTyrLysValGlyArgAspArgLeuTrpThrProProAsnPheSerSerTrpT

1621  CCAGAGATGAATACCGGCTACAAGTACTACTACGTGTCGGAGGGACCGTACGAGAAGGTCA  1680
      hrArgAspGluTyrGlyTyrLysTyrTyrTyrValSerGluGlyProTyrGluLysValA

1681  ACCAGTACGTGAATGTGCAACGCAACCACAGCGAACTGATTCGCCGCATTGGAGCGGACA  1740
      snGlnTyrValAsnValGlnArgAsnHisSerGluLeuIleArgArgIleGlyAlaAspS

1741  GCACGGTGCTCCTCAAGAACGACGGCGCTCTGCCTTTGACTGGTAAGGAGCGCCTGGTCG  1800
      erThrValLeuLeuLysAsnAspGlyAlaLeuProLeuThrGlyLysGluArgLeuValA

1801  CGCTTATCGGAGAAGATGCGGGCTCCAACCCTTATGGTGCCAACGGCTGCAGTGACCGTG  1860
      laLeuIleGlyGluAspAlaGlySerAsnProTyrGlyAlaAsnGlyCysSerAspArgG

1861  GATGCGACAATGGAACATTGGCGATGGGCTGGGGAAGTGGTACTGCCAACTTCCCATACC  1920
      lyCysAspAsnGlyThrLeuAlaMetGlyTrpGlySerGlyThrAlaAsnPheProTyrL

1921  TGGTGACCCCCGAGCAGGCCATCTCAAACGAGGTGCTTAAGCACAAGAATGGTGTATTCA  1980
      euValThrProGluGlnAlaIleSerAsnGluValLeuLysHisLysAsnGlyValPheT

1981  CCGCCACCGATAACTGGGCTATCGATCAGATTGAGGCGCTTGCTAAGACCGCCAGGTAAG  2040
      hrAlaThrAspAsnTrpAlaIleAspGlnIleGluAlaLeuAlaLysThrAlaArg

2041  AAGATCCCCGATTCTTTTCCTTCTTGTGCAATGGATGCTGACAACATGCTAGTGTCTCTC  2100
                        Intron#5                            ValSerL 2101  TTGTCTTTGTCAACGCCGACTCTGGTGAGGGTTACATCAATGTGGACGGAAACCTGGGTG  2160
      euValPheValAsnAlaAspSerGlyGluGlyTyrIleAsnValAspGlyAsnLeuGlyA 2161  ACCGCAGGAACCTGACCCTGTGGAGGAACCGCGATAATGTGATCAAGGCTGCTGCTAGCA  2220
      spArgArgAsnLeuThrLeuTrpArgAsnArgAspAsnValIleLysAlaAlaAlaSerA 2281  ACCACAACCCCAATGTTACCGCTATCCTCTGGGGTGGTTTGCCCGGTCAGGAGTCTGGCA  2340
      snHisAsnProAsnValThrAlaIleLeuTrpGlyGlyLeuProGlyGlnGluSerGlyA 2341  ACTCTCTTGCCGACGTCCTCTATGGCCGTGTCAACCCCGGTGCCAAGTCGCCCTTTACCT  2400
      snSerLeuAlaAspValLeuTyrGlyArgValAsnProGlyAlaLysSerProPheThrT 2401  GGGGCAAGACTCGTGAGGCCTACCAAGACTACTTGGTCACCGAGCCCAACAACGGCAACG  2460
      rpGlyLysThrArgGluAlaTyrGlnAspTyrLeuValThrGluProAsnAsnGlyAsnG 2461  GAGCCCCTCAGGAAGACTTTGTCGAGGGCGTCTTCATTGACTACCGTGGATTTGACAAGC  2520
      lyAlaProGlnGluAspPheValGluGlyValPheIleAspTyrArgGlyPheAspLysA 2521  GCAACGAGACCCCGATCTACGAGTTCGGCTATGGTCTGAGCTACGCCACTTTCAACTACT  2580
      rgAsnGluThrProIleTyrGluPheGlyTyrGlyLeuSerTyrAlaThrPheAsnTyrS 2581  CGAACCTTGAGGTGCAGGTGCTGAGCGCCCCTGCATACGAGCCTGCTTCGGGTGAGACCG  2640
      erAsnLeuGluValGlnValLeuSerAlaProAlaTyrGluProAlaSerGlyGluThrG 2701  TGCAGAGAATTACCAAGTTCATCTACCCCTGGCTCAACGGTACCGATCTCGAGGCATCTT  2760
      luGlnArgIleThrLysPheIleTyrProTrpLeuAsnGlyThrAspLeuGluAlaSerS 2761  CCGGGGATGCTAGCTACGGGCAGGACTCCTCCGACTATCTTCCCGAGGGAGCCACCGATG  2820
      erGlyAspAlaSerTyrGlyGlnAspSerSerAspTyrLeuProGluGlyAlaThrAspG
```

Fig. 5a (continued)

```
2821 GCTCTGCGCAACCGATCCTGCCTGCCGGTGGCGGTCCTGGCGGCAACCCTCGCCTGTACG 2880
     lySerAlaGlnProIleLeuProAlaGlyGlyGlyProGlyGlyAsnProArgLeuTyrA

2881 ACGAGCTCATCCGCGTGTCAGTGACCATCAAGAACACCGGCAAGGTTGCTGGTGATGAAG 2940
     spGluLeuIleArgValSerValThrIleLysAsnThrGlyLysValAlaGlyAspGluV

2941 TTCCCCAACTGGTAAGTAAACATGAGGTCCGAACGAGGTTGAACAAAGCTAATCAGTCGC 3000
     alProGlnLeu              Intron#6

3001 AGTATGTTTCCCTTGGCGGTCCCAATGAGCCCAAGATCGTGCTGCGTCAATTCGAGCGCA 3060
         TyrValSerLeuGlyGlyProAsnGluProLysIleValLeuArgGlnPheGluArgI

3061 TCACGCTGCAGCCGTCGGAGGAGACGAAGTGGAGCACGACTCTGACGCGCCGTGACCTTG 3120
     leThrLeuGlnProSerGluGluThrLysTrpSerThrThrLeuThrArgArgAspLeuA

3121 CAAACTGGAATGTTGAGAAGCAGGACTGGGAGATTACGTCGTATCCCAAGATGGTGTTTG 3180
     laAsnTrpAsnValGluLysGlnAspTrpGluIleThrSerTyrProLysMetValPheV

3181 TCGGAAGCTCCTCGCGGAAGCTGCCGCTCCGGGCGTCTCTGCCTACTGTTCACTAAATAG 3240
     alGlySerSerSerArgLysLeuProLeuArgAlaSerLeuProThrValHis***

3241 CTCTCAAATGGTATACCATGATGGCCGTGGTATATGAATTAATGATTTATGCCAACAGCA 3300
3301 AGACCACTGTAGATGTAGATGTAGAATGAGTATTGCGTAGTAGCGTGTAGATGATGATAC 3360
3361 AAGCGATCCGACACATGGTAGGAAGAGTGGCGCTAGTTGGGGCGGAAACCAAGCGACGTC 3420
3421 ATCCGCTGCCGACTTCGCCAGTCTTTCTTCTTTTCCTCTTCAGCCTTCTTCCTCCGCTTA 3480
3481 ATCCAGCAACCATTGCCAATTGCCTCTACAACAACTAATTGCCATAATACTCTACTCCTA 3540
3541 TTCAATATATACACCACAATCTCGACATAATCACACAAGCCTGAACACACGAGCAACCAT 3600
3601 GCCCTCTCCCGATCCTCCAGCCCCAGCGATACGACCCTTCCAACCACCCATAACAGCGCT 3660
3661 CCTCATCTACCCAGCGACCCTAATCGTGGGATCACTCTTCTCCGTCCTCTCTCCCACCGC 3720
3721 ACAAGGCACACGCGACGACGGCTCCAGCACCCTCCACCCACACGTCGAGCCCCTAGCCCC 3780
3781 GTCCATCGCGTCAGACCTCAACCTCTCCTTTCCTCCGCCGCGCCCCGTCAACTACTTCGC 3840
3841 TCGCAAAGACAACATCTTCAATCTATATTCGTCAAAGTCGGC 3885
```

Fig. 5a (continued)

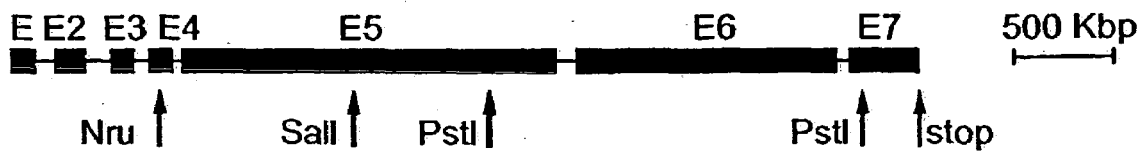

Fig. 5b

Fig. 11a  35SΩ + bg11
Fig. 11b  35SΩ + Ce11 + bg11
Fig. 11c  35SΩ + Ce11 + bg11 + HDEL
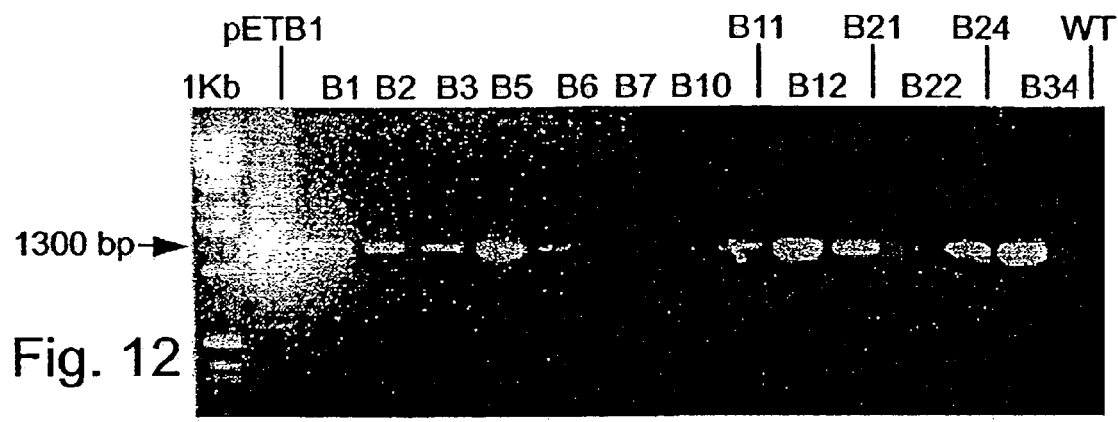
Fig. 12
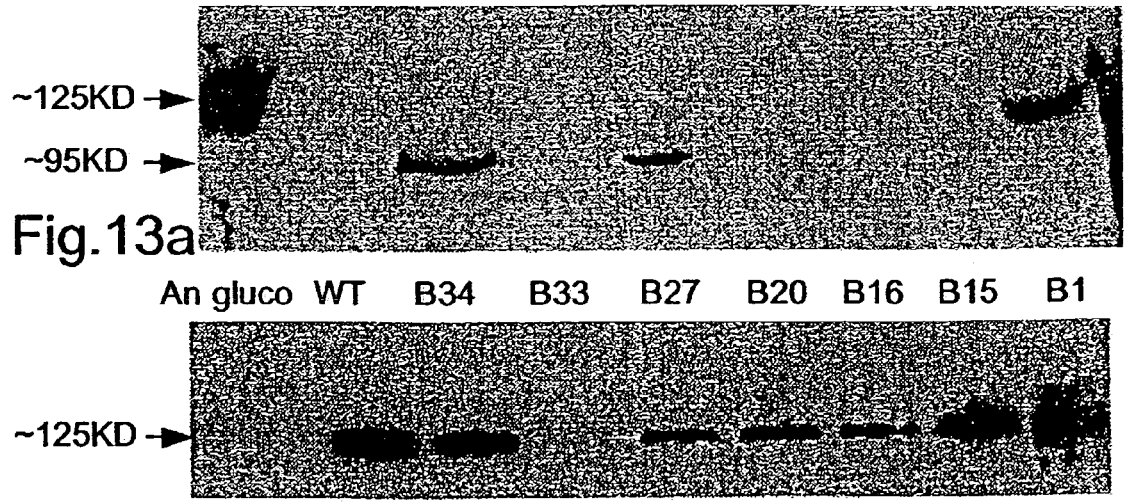
Fig. 13a
Fig. 13b WT  CB10  CB11  CBT3  CBT8 CBT15   B1   B34  An Glu

SEQUENCE LISTING

<160> NUMBER OF SEQ ID NOS: 24

<210> SEQ ID NO 1
<211> LENGTH: 2583
<212> TYPE: DNA
<213> ORGANISM: Aspergillus niger

<400> SEQUENCE: 1

```
atgaggttca ctttgatcga ggcggtggct ctgactgccg tctcgctggc cagcgctgat      60
gaattggcct actccccacc gtattaccca tccccttggg ccaatggcca gggcgactgg     120
gcgcaggcat accagcgcgc tgttgatatt gtctcgcaaa tgacattgga tgagaaggtc     180
```

-continued

| | |
|---|---|
| aatctgacca caggaactgg atgggaattg gaactatgtg ttggtcagac tggcggtgtt | 240 |
| ccccgattgg gagttccggg aatgtgttta caggatagcc ctctgggcgt tcgcgactcc | 300 |
| gactacaact ctgctttccc tgccggcatg aacgtggctg cgacctggga caagaatctg | 360 |
| gcataccttc gcggcaaggc tatgggtcag gaatttagtg acaagggtgc cgatatccaa | 420 |
| ttgggtccag ctgccggccc tctcggtaga agtcccgacg gtggtcgtaa ctgggagggc | 480 |
| ttctccccag accctgccct aagtggtgtg ctctttgccg agaccatcaa gggtatccaa | 540 |
| gatgctggtg tggttgcgac ggctaagcac tacattgctt acgagcaaga gcatttccgt | 600 |
| caggcgcctg aagcccaagg ttttggattt aatatttccg agagtggaag tgcgaacctc | 660 |
| gatgataaga ctatgcacga gctgtacctc tggcccttcg cggatgccat ccgtgcaggt | 720 |
| gctggcgctg tgatgtgctc ctacaaccag atcaacaaca gttatggctg ccagaacagc | 780 |
| tacactctga acaagctgct caaggccgag ctgggcttcc agggctttgt catgagtgat | 840 |
| tgggctgctc accatgctgg tgtgagtggt gctttggcag gattggatat gtctatgcca | 900 |
| ggagacgtcg actacgacag tggtacgtct tactggggta caaacttgac cattagcgtg | 960 |
| ctcaacggaa cggtgcccca atggcgtgtt gatgacatgg ctgtccgcat catggccgcc | 1020 |
| tactacaagg tcggccgtga ccgtctgtgg actcctccca acttcagctc atggaccaga | 1080 |
| gatgaatacg gctacaagta ctactacgtg tcggagggac cgtacgagaa ggtcaaccag | 1140 |
| tacgtgaatg tgcaacgcaa ccacagcgaa ctgattcgcc gcattggagc ggacagcacg | 1200 |
| gtgctcctca gaacgacgg cgctctgcct ttgactggta aggagcgcct ggtcgcgctt | 1260 |
| atcggagaag atgcgggctc caacccttat ggtgccaacg gctgcagtga ccgtggatgc | 1320 |
| gacaatggaa cattggcgat gggctgggga agtggtactg ccaacttccc ataccggtg | 1380 |
| accccgagc aggccatctc aaacgaggtg cttaagcaca agaatggtgt attcaccgcc | 1440 |
| accgataact gggctatcga tcaaattgag gcgcttgcta agaccgccag tgtctctctt | 1500 |
| gtctttgtca acgccgactc tggtgagggt tacatcaatg tggacggaaa cctgggtgac | 1560 |
| cgcaggaacc tgaccctgtg gaggaacggc gataatgtga tcaaggctgc tgctagcaac | 1620 |
| tgcaacaaca caatcgttgt cattcactct gtcggaccag tcttggttaa cgagtggtac | 1680 |
| gacaaccca atgttaccgc tatcctctgg ggtggtttgc ccggtcagga gtctggcaac | 1740 |
| tctcttgccg acgtcctcta tggccgtgtc aaccccggtg ccaagtcgcc ctttacctgg | 1800 |
| ggcaagactc gtgaggccta ccaagactac ttggtcaccg agcccaacaa cggcaacgga | 1860 |
| gccccctcagg aagactttgt cgagggcgtc ttcattgact accgtggatt tgacaagcgc | 1920 |
| aacgagaccc cgatctacga gttcggctat ggtctgagct acaccacttt caactactcg | 1980 |
| aaccttgagg tgcaggtgct gagcgcccct gcatacgagc ctgcttcggg tgagaccgag | 2040 |
| gcagcgccaa ccttcggaga ggttggaaat gcgtcggatt acctctaccc cagcggattg | 2100 |
| ctgagaatta ccaagttcat ctaccccctgg ctcaacggta ccgatctcga ggcatcttcc | 2160 |
| ggggatgcta gctacgggca ggactcctcc gactatcttc ccgagggagc caccgatggc | 2220 |
| tctgcgcaac cgatcctgcc tgccggtggc ggtcctggcg caaccctcg cctgtacgac | 2280 |
| gagctcatcc gcgtgtcagt gaccatcaag aacaccggca aggttgctgg tgatgaagtt | 2340 |
| ccccaactgt atgtttccct tggcggtccc aatgagccca agatcgtgct gcgtcaattc | 2400 |
| gagcgcatca cgctgcagcc gtcggaggag acgaagtgga gcacgactct gacgcgccgt | 2460 |
| gaccttgcaa actggaatgt tgagaagcag gactgggaga ttacgtcgta tcccaagatg | 2520 |
| gtgtttgtcg gaagctcctc gcggaagctg ccgctccggg cgtctctgcc tactgttcac | 2580 |

-continued

```
taa                                                                    2583
```

<210> SEQ ID NO 2
<211> LENGTH: 860
<212> TYPE: PRT
<213> ORGANISM: Aspergillus niger

<400> SEQUENCE: 2

```
Met Arg Phe Thr Leu Ile Glu Ala Val Ala Leu Thr Ala Val Ser Leu
1               5                   10                  15

Ala Ser Ala Asp Glu Leu Ala Tyr Ser Pro Pro Tyr Tyr Pro Ser Pro
            20                  25                  30

Trp Ala Asn Gly Gln Gly Asp Trp Ala Gln Ala Tyr Gln Arg Ala Val
        35                  40                  45

Asp Ile Val Ser Gln Met Thr Leu Asp Glu Lys Val Asn Leu Thr Thr
    50                  55                  60

Gly Thr Gly Trp Glu Leu Glu Leu Cys Val Gly Gln Thr Gly Gly Val
65                  70                  75                  80

Pro Arg Leu Gly Val Pro Gly Met Cys Leu Gln Asp Ser Pro Leu Gly
                85                  90                  95

Val Arg Asp Ser Asp Tyr Asn Ser Ala Phe Pro Ala Gly Met Asn Val
            100                 105                 110

Ala Ala Thr Trp Asp Lys Asn Leu Ala Tyr Leu Arg Gly Lys Ala Met
        115                 120                 125

Gly Gln Glu Phe Ser Asp Lys Gly Ala Asp Ile Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Phe
        195                 200                 205

Gly Phe Asn Ile Ser Glu Ser Gly Ser Ala Asn Leu Asp Asp Lys Thr
    210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Ala Gly Val
        275                 280                 285

Ser Gly Ala Leu Ala Gly Leu Asp Met Ser Met Pro Gly Asp Val Asp
    290                 295                 300

Tyr Asp Ser Gly Thr Ser Tyr Trp Gly Thr Asn Leu Thr Ile Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
            340                 345                 350

Pro Asn Phe Ser Ser Trp Thr Arg Asp Glu Tyr Gly Tyr Lys Tyr Tyr
        355                 360                 365
```

-continued

```
Tyr Val Ser Glu Gly Pro Tyr Glu Lys Val Asn Gln Tyr Val Asn Val
    370                 375                 380

Gln Arg Asn His Ser Glu Leu Ile Arg Arg Ile Gly Ala Asp Ser Thr
385                 390                 395                 400

Val Leu Leu Lys Asn Asp Gly Ala Leu Pro Leu Thr Gly Lys Glu Arg
                405                 410                 415

Leu Val Ala Leu Ile Gly Glu Asp Ala Gly Ser Asn Pro Tyr Gly Ala
                420                 425                 430

Asn Gly Cys Ser Asp Arg Gly Cys Asp Asn Gly Thr Leu Ala Met Gly
            435                 440                 445

Trp Gly Ser Gly Thr Ala Asn Phe Pro Tyr Leu Val Thr Pro Glu Gln
    450                 455                 460

Ala Ile Ser Asn Glu Val Leu Lys His Lys Asn Gly Val Phe Thr Ala
465                 470                 475                 480

Thr Asp Asn Trp Ala Ile Asp Gln Ile Glu Ala Leu Ala Lys Thr Ala
                485                 490                 495

Ser Val Ser Leu Val Phe Val Asn Ala Asp Ser Gly Glu Gly Tyr Ile
                500                 505                 510

Asn Val Asp Gly Asn Leu Gly Asp Arg Arg Asn Leu Thr Leu Trp Arg
            515                 520                 525

Asn Gly Asp Asn Val Ile Lys Ala Ala Ala Ser Asn Cys Asn Asn Thr
    530                 535                 540

Ile Val Val Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
                565                 570                 575

Glu Ser Gly Asn Ser Leu Ala Asp Val Leu Tyr Gly Arg Val Asn Pro
                580                 585                 590

Gly Ala Lys Ser Pro Phe Thr Trp Gly Lys Thr Arg Glu Ala Tyr Gln
            595                 600                 605

Asp Tyr Leu Val Thr Glu Pro Asn Asn Gly Asn Gly Ala Pro Gln Glu
    610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Glu Val Gln Val Leu Ser Ala Pro Ala Tyr
                660                 665                 670

Glu Pro Ala Ser Gly Glu Thr Glu Ala Ala Pro Thr Phe Gly Glu Val
            675                 680                 685

Gly Asn Ala Ser Asp Tyr Leu Tyr Pro Ser Gly Leu Leu Arg Ile Thr
    690                 695                 700

Lys Phe Ile Tyr Pro Trp Leu Asn Gly Thr Asp Leu Glu Ala Ser Ser
705                 710                 715                 720

Gly Asp Ala Ser Tyr Gly Gln Asp Ser Ser Asp Tyr Leu Pro Glu Gly
                725                 730                 735

Ala Thr Asp Gly Ser Ala Gln Pro Ile Leu Pro Ala Gly Gly Gly Pro
                740                 745                 750

Gly Gly Asn Pro Arg Leu Tyr Asp Glu Leu Ile Arg Val Ser Val Thr
            755                 760                 765

Ile Lys Asn Thr Gly Lys Val Ala Gly Asp Glu Val Pro Gln Leu Tyr
    770                 775                 780
```

```
Val Ser Leu Gly Gly Pro Asn Glu Pro Lys Ile Val Leu Arg Gln Phe
785                 790                 795                 800

Glu Arg Ile Thr Leu Gln Pro Ser Glu Glu Thr Lys Trp Ser Thr Thr
            805                 810                 815

Leu Thr Arg Arg Asp Leu Ala Asn Trp Asn Val Glu Lys Gln Asp Trp
        820                 825                 830

Glu Ile Thr Ser Tyr Pro Lys Met Val Phe Val Gly Ser Ser Ser Arg
            835                 840                 845

Lys Leu Pro Leu Arg Ala Ser Leu Pro Thr Val His
        850                 855                 860

<210> SEQ ID NO 3
<211> LENGTH: 3885
<212> TYPE: DNA
<213> ORGANISM: Aspergillus niger

<400> SEQUENCE: 3
tccattcgcc catgcttagc gtgtcttttc tttgaacact gcatgcggga ctgtgaattg     60
catgagtggg tagctttgcg gagacagctg cactggcata catcatcgtt gggttcctca    120
attcgcatgc cgtggcggac ggtcactttg tggcgctcaa actatttaat atggcccagc    180
tccccttttct ctcgctgttt tcgtttctgt cctccctaaa cctccagtct ctccattgga    240
caggtgttgc acgttgctc acctggtttg ttttgctccc cctttgggcg accttgccat    300
catgaggttc actttgatcg aggcggtggc tctgactgcc gtctcgctgg ccagcgctgt    360
acgtgccgtt actttgtcct gagaattgca attgtgctta attagattca tttgtttgtt    420
tcatcatcgc tgacaatggt cttttcatag gatgaattgg cctactcccc accgtattac    480
ccatccccctt gggccaatgg ccagggcgac tgggcgcagg cataccagcg cgctgttgat    540
attgtctcgc aaatgacatt ggatgagaag gtcaatctga ccacaggaac tgggtagggc    600
ttacatggcg caatctgtat gctccggcta caaacttcta catgggaatt ggaactatgt    660
gttggtcaga ctggcggtgt tccccggtag gtttgaaaat attgtcgaga caggggacat    720
tattgattaa cggtgacaga ttgggagttc cggaatgtg tttacaggat agccctctgg    780
gcgttcgcga ctgtaagcca tctgctgttg ttaggcttcg atgctcttac tgacacggcg    840
cagccgacta caactctgct ttccctgccg gcatgaacgt ggctgcaacc tgggacaaga    900
atctggcata ccttcgcggc aaggctatgg gtcaggaatt tagtgacaag ggtgccgata    960
tccaattggg tccagctgcc ggccctctcg gtagaagtcc cgacggtggt cgtaactggg   1020
agggcttctc cccagaccct gccctaagtg gtgtgctctt tgccgagacc atcaagggta   1080
tccaagatgc tggtgtggtt gcgacggcta agcactacat tgcttacgag caagagcatt   1140
tccgtcaggc gcctgaagcc caaggttttg gatttaatat ttccgagagt ggaagtgcga   1200
acctcgatga taagactatg cacgagctgt acctctggcc cttcgcggat gccatccgtg   1260
caggtgctgg cgctgtgatg tgctcctaca accagatcaa caacagttat ggctgccaga   1320
acagctacac tctgaacaag ctgctcaagg ccgagctggg cttccaggc tttgtcatga   1380
gtgattggc tgctcaccat gctggtgtga gtggtgcttt ggcaggattg gatatgtcta   1440
tgccaggaga cgtcgactac gacagtggta cgtcttactg gggtacaaac ttgaccatta   1500
gcgtgctcaa cggaacggtg ccccaatggc gtgttgatga catggctgtc cgcatcatgg   1560
ccgcctacta caaggtcggc cgtgaccgtc tgtggactcc tcccaacttc agctcatgga   1620
ccagagatga atacggctac aagtactact acgtgtcgga gggaccgtac gagaaggtca   1680
```

-continued

```
accagtacgt gaatgtgcaa cgcaaccaca gcgaactgat tcgccgcatt ggagcggaca    1740
gcacggtgct cctcaagaac gacggcgctc tgcctttgac tggtaaggag cgcctggtcg    1800
cgcttatcgg agaagatgcg ggctccaacc cttatggtgc caacggctgc agtgaccgtg    1860
gatgcgacaa tggaacattg gcgatgggct ggggaagtgg tactgccaac ttcccatacc    1920
tggtgacccc cgagcaggcc atctcaaacg aggtgcttaa gcacaagaat ggtgtattca    1980
ccgccaccga taactgggct atcgatcaaa ttgaggcgct tgctaagacc gccaggtaag    2040
aagatccccg attcttttcc ttcttgtgca atggatgctg acaacatgct agtgtctctc    2100
ttgtctttgt caacgccgac tctggtgagg gttacatcaa tgtggacgga aacctgggtg    2160
accgcaggaa cctgaccctg tggaggaacc gcgataatgt gatcaaggct gctgctagca    2220
actgcaacaa cacaatcgtt gtcattcact ctgtcggacc agtcttggtt aacgagtggt    2280
acgacaaccc caatgttacc gctatcctct ggggtggttt gcccggtcag gagtctggca    2340
actctcttgc cgacgtcctc tatggccgtg tcaaccccgg tgccaagtcg ccctttacct    2400
ggggcaagac tcgtgaggcc taccaagact acttggtcac cgagcccaac aacggcaacg    2460
gagcccctca ggaagacttt gtcgagggcg tcttcattga ctaccgtgga tttgacaagc    2520
gcaacgagac cccgatctac gagttcggct atggtctgag ctacaccact ttcaactact    2580
cgaaccttga ggtgcaggtg ctgagcgccc tgcatacga gcctgcttcg ggtgagaccg    2640
aggcagcgcc aaccttcgga gaggttggaa atgcgtcgga ttacctctac cccagcggat    2700
tgctgagaat taccaagttc atctacccct ggctcaacgg taccgatctc gaggcatctt    2760
ccggggatgc tagctacggg caggactcct ccgactatct tcccgaggga gccaccgatg    2820
gctctgcgca accgatcctg cctgccggtg gcggtcctgg cggcaaccct cgcctgtacg    2880
acgagctcat ccgcgtgtca gtgaccatca agaacaccgg caaggttgct ggtgatgaag    2940
ttccccaact ggtaagtaaa catgaggtcc gaacgaggtt gaacaaagct aatcagtcgc    3000
agtatgtttc ccttggcggt cccaatgagc ccaagatcgt gctgcgtcaa ttcgagcgca    3060
tcacgctgca gccgtcggag gagacgaagt ggagcacgac tctgacgcgc cgtgaccttg    3120
caaactggaa tgttgagaag caggactggg agattacgtc gtatcccaag atggtgtttg    3180
tcggaagctc ctcgcggaag ctgccgctcc gggcgtctct gcctactgtt cactaaatag    3240
ctctcaaatg gtataccatg atggccgtgg tatatgaatt aatgatttat gccaacagca    3300
agaccactgt agatgtagat gtagaatgag tattgcgtag tagcgtgtag atgatgatac    3360
aagcgatccg acacatggta ggaagagtgg cgctagttgg ggcggaaacc aagcgacgtc    3420
atccgctgcc gacttcgcca gtctttcttc ttttcctctt cagccttctt cctccgctta    3480
atccagcaac cattgccaat tgcctctaca acaactaatt gccataatac tctactccta    3540
ttcaatatat acaccacaat ctcgacataa tcacacaagc ctgaacacac gagcaaccat    3600
gccctctccc gatcctccag ccccagcgat acgacccttc caaccaccca taacagcgct    3660
cctcatctac ccagcgaccc taatcgtggg atcactcttc tccgtcctct ctcccaccgc    3720
acaaggcaca cgcgacgacg gctccagcac cctccaccca cacgtcgagc ccctagcccc    3780
gtccatcgcg tcagacctca acctctcctt tcctccgccg cgcccgtca actacttcgc    3840 tcgcaaagac aacatcttca atctatattc gtcaaagtcg gctgg              3885
```

<210> SEQ ID NO 4
<211> LENGTH: 6
<212> TYPE: PRT
<213> ORGANISM: Aspergillus niger

```
<400> SEQUENCE: 4

Ser Pro Pro Tyr Tyr Pro
1               5

<210> SEQ ID NO 5
<211> LENGTH: 16
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (2)..()
<223> OTHER INFORMATION: any nucleotide
<220> FEATURE:
<221> NAME/KEY: misc_feature
<222> LOCATION: (5)..()
<223> OTHER INFORMATION: any nucleotide
<220> FEATURE:
<221> NAME/KEY: misc_feature
<222> LOCATION: (8)..()
<223> OTHER INFORMATION: any nucleotide

<400> SEQUENCE: 5
snccnccnta ytaycc                                                16

<210> SEQ ID NO 6
<211> LENGTH: 8
<212> TYPE: PRT
<213> ORGANISM: Aspergillus niger

<400> SEQUENCE: 6

Gln Pro Ile Leu Pro Ala Gly Gly
1               5

<210> SEQ ID NO 7
<211> LENGTH: 21
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: modified_base
<222> LOCATION: (4)..(4)
<223> OTHER INFORMATION: i
<220> FEATURE:
<221> NAME/KEY: misc_feature
<222> LOCATION: (7)..()
<223> OTHER INFORMATION: any nucleotide
<220> FEATURE:
<221> NAME/KEY: misc_feature
<222> LOCATION: (10)..()
<223> OTHER INFORMATION: any nucleotide
<220> FEATURE:
<221> NAME/KEY: misc_feature
<222> LOCATION: (16)..()
<223> OTHER INFORMATION: any nucleotide

<400> SEQUENCE: 7
tccngcnggn ardatnggyt g                                          21

<210> SEQ ID NO 8
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 8
```

-continued aaaccatggc tgatgaattg gcatactccc cacc    34

<210> SEQ ID NO 9
<211> LENGTH: 33
<212> TYPE: DNA
<213> ORGANISM: Artificial sequence
<220> FEATURE:
<223> OTHER INFORMATION: synthetic oligonucleotide

<400> SEQUENCE: 9
aaaggatcct tagtgaacag taggcagaga cgc    33

<210> SEQ ID NO 10
<211> LENGTH: 20
<212> TYPE: PRT
<213> ORGANISM: Artificial sequence
<220> FEATURE:
<223> OTHER INFORMATION: Staphylococcus aureus V8 protease cleavage
      product of BGL1 protein

<400> SEQUENCE: 10

Asp Glu Leu Ala Tyr Ser Pro Pro Tyr Tyr Pro Ser Pro Trp Ala Asn
1               5                   10                  15

Gly Gln Gly Asp
            20

<210> SEQ ID NO 11
<211> LENGTH: 25
<212> TYPE: PRT
<213> ORGANISM: Artificial sequence
<220> FEATURE:
<223> OTHER INFORMATION: Staphylococcus aureus V8 protease cleavage
      product of BGL1 protein

<400> SEQUENCE: 11

Val Leu Lys His Lys Asn Gly Val Phe Thr Ala Thr Asp Asn Trp Ala
1               5                   10                  15

Ile Asp Gln Ile Glu Ala Leu Ala Lys
            20                  25

<210> SEQ ID NO 12
<211> LENGTH: 21
<212> TYPE: PRT
<213> ORGANISM: Artificial sequence
<220> FEATURE:
<223> OTHER INFORMATION: Staphylococcus aureus V8 protease cleavage
      product of BGL1 protein

<400> SEQUENCE: 12

Gly Ala Thr Asp Gly Ser Ala Gln Pro Ile Leu Pro Ala Gly Gly Gly
1               5                   10                  15

Pro Gly Gly Asn Pro
            20

<210> SEQ ID NO 13
<211> LENGTH: 3212
<212> TYPE: DNA
<213> ORGANISM: Artificial sequence
<220> FEATURE:
<223> OTHER INFORMATION: Sequence of recombinant construct expressing
      BGL1 protein

<400> SEQUENCE: 13
gaattcccga tcctatctgt cacttcatca aaggacagt agaaaaggaa ggtggcacta    60
caaatgccat cattgcgata aggaaaggc tatcgttcaa gatgcctctg ccgacagtgg   120

-continued

| | | | |
|---|---|---|---|
| tcccaaagat ggaccccac ccacgaggag catcgtggaa aaagaagacg ttccaaccac | 180 |
| gtcttcaaag caagtggatt gatgtgatat ctccactgac gtaagggatg acgcacaatc | 240 |
| ccactatcct tcgcaagacc cttcctctat ataaggaagt tcatttcatt tggagaggac | 300 |
| aggcttcttg agatccttca acaattacca acaacaacaa acaacaaaca acattacaat | 360 |
| tactatttac aattacagtc gaccatggct gatgaattgg cctactcccc accgtattac | 420 |
| ccatcccctt gggccaatgg ccagggcgac tgggcgcagg cataccagcg cgctgttgat | 480 |
| attgtctcgc aaatgacatt ggatgagaag gtcaatctga ccacaggaac tggatgggaa | 540 |
| ttggaactat gtgttggtca gactggcggt gttccccgat gggagttcc gggaatgtgt | 600 |
| ttacaggata gccctctggg cgttcgcgac tccgactaca actctgcttt ccctgccggc | 660 |
| atgaacgtgg ctgcgacctg gacaagaat ctggcatacc ttcgcggcaa ggctatgggt | 720 |
| caggaattta gtgacaaggg tgccgatatc caattgggtc cagctgccgg ccctctcggt | 780 |
| agaagtcccg acggtggtcg taactgggag ggcttctccc cagaccctgc cctaagtggt | 840 |
| gtgctctttg ccgagaccat caagggtatc caagatgctg gtgtggttgc gacggctaag | 900 |
| cactacattg cttacgagca agagcatttc cgtcaggcgc tgaagcccca aggttttgga | 960 |
| tttaatattt ccgagagtgg aagtgcgaac ctcgatgata agactatgca cgagctgtac | 1020 |
| ctctggcct tcgcggatgc catccgtgca ggtgctggcg ctgtgatgtg ctcctacaac | 1080 |
| cagatcaaca acagttatgg ctgccagaac agctacactc tgaacaagct gctcaaggcc | 1140 |
| gagctgggct tccagggctt tgtcatgagt gattgggctc tcaccatgc tggtgtgagt | 1200 |
| ggtgctttgg caggattgga tatgtctatg ccaggagacg tcgactacga cagtggtacg | 1260 |
| tcttactggg gtacaaactt gaccattagc gtgctcaacg gaacggtgcc ccaatggcgt | 1320 |
| gttgatgaca tggctgtccg catcatggcc gcctactaca aggtcggccg tgaccgtctg | 1380 |
| tggactcctc ccaacttcag ctcatggacc agagatgaat acggctacaa gtactactac | 1440 |
| gtgtcggagg gaccgtacga gaaggtcaac cagtacgtga atgtgcaacg caaccacagc | 1500 |
| gaactgattc gccgcattgg agcggacagc acggtgctcc tcaagaacga cggcgctctg | 1560 |
| cctttgactg gtaaggagcg cctggtcgcg cttatcggag aagatgcggg ctccaaccct | 1620 |
| tatggtgcca acgctgcag tgaccgtgga tgcgacaatg gaacattggc gatgggctgg | 1680 |
| ggaagtggta ctgccaactt cccatacctg gtgaccccg agcaggccat ctcaaacgag | 1740 |
| gtgcttaagc acaagaatgg tgtattcacc gccaccgata ctgggctat cgatcaaatt | 1800 |
| gaggcgcttg ctaagaccgc cagtgtctct cttgtctttg tcaacgccga ctctggtgag | 1860 |
| ggttacatca atgtggacgg aaacctgggt gaccgcagga acctgaccct gtggaggaac | 1920 |
| ggcgataatg tgatcaaggc tgctgctagc aactgcaaca acacaatcgt tgtcattcac | 1980 |
| tctgtcggac cagtcttggt taacgagtgg tacgacaacc ccaatgttac cgctatcctc | 2040 |
| tggggtggtt tgcccggtca ggagtctggc aactctcttg ccgacgtcct ctatggccgt | 2100 |
| gtcaaccccg gtgccaagtc gccctttacc tggggcaaga ctcgtgaggc ctaccaagac | 2160 |
| tacttggtca ccgagcccaa caacggcaac ggagcccctc aggaagactt tgtcgagggc | 2220 |
| gtcttcattg actaccgtgg atttgacaag cgcaacgaga cccgatcta cgagttcggc | 2280 |
| tatggtctga gctacaccac tttcaactac tcgaaccttg aggtgcaggt gctgagcgcc | 2340 |
| cctgcatacg agcctgcttc gggtgagacc gaggcagcgc caaccttcgg agaggttgga | 2400 |
| aatgcgtcgg attacctcta ccccagcgga ttgctgagaa ttaccaagtt catctacccc | 2460 |

```
tggctcaacg gtaccgatct cgaggcatct tccggggatg ctagctacgg gcaggactcc    2520
tccgactatc ttcccgaggg agccaccgat ggctctgcgc aaccgatcct gcctgccggt    2580
ggcggtcctg gcggcaaccc tcgcctgtac gacgagctca tccgcgtgtc agtgaccatc    2640
aagaacaccg gcaaggttgc tggtgatgaa gttccccaac tgtatgtttc ccttggcggt    2700
cccaatgagc ccaagatcgt gctgcgtcaa ttcgagcgca tcacgctgca gccgtcggag    2760
gagacgaagt ggagcacgac tctgacgcgc cgtgaccttg caaactggaa tgttgagaag    2820
caggactggg agattacgtc gtatcccaag atggtgtttg tcggaagctc ctcgcggaag    2880
ctgccgctcc gggcgtctct gcctactgtt cactaacccg gcgagctcg aattgatcgt    2940 tcaaacattt ggcaataaag tttcttaaga ttgaatcctg ttgccggtct tgcgatgatt    3000
atcatataat ttctgttgaa ttacgttaag catgtaataa ttaaacatgt aatgcatgac    3060
gttatttatg agatggggtt tttatgatta agagtccccg caattataca ttttaatacg    3120
cgatagaaaa acaaaatata gcgcccaaac taaggataaa attattcgcg ccgcgggggg    3180
gcattctatg gttactagat ctctagaatt cc                                  3212
```

<210> SEQ ID NO 14
<211> LENGTH: 841
<212> TYPE: PRT
<213> ORGANISM: Artificial sequence
<220> FEATURE:
<223> OTHER INFORMATION: Sequence of recombinant BGL1 protein

<400> SEQUENCE: 14

```
Asp Glu Leu Ala Tyr Ser Pro Pro Tyr Tyr Pro Ser Pro Trp Ala Asn
1               5                   10                  15

Gly Gln Gly Asp Trp Ala Gln Ala Tyr Gln Arg Ala Val Asp Ile Val
            20                  25                  30

Ser Gln Met Thr Leu Asp Glu Lys Val Asn Leu Thr Thr Gly Thr Gly
        35                  40                  45

Trp Glu Leu Glu Leu Cys Val Gly Gln Thr Gly Gly Val Pro Arg Leu
    50                  55                  60

Gly Val Pro Gly Met Cys Leu Gln Asp Ser Pro Leu Gly Val Arg Asp
65                  70                  75                  80

Ser Asp Tyr Asn Ser Ala Phe Pro Ala Gly Met Asn Val Ala Ala Thr
                85                  90                  95

Trp Asp Lys Asn Leu Ala Tyr Leu Arg Gly Lys Ala Met Gly Gln Glu
            100                 105                 110

Phe Ser Asp Lys Gly Ala Asp Ile Gln Leu Gly Pro Ala Ala Gly Pro
        115                 120                 125

Leu Gly Arg Ser Pro Asp Gly Gly Arg Asn Trp Glu Gly Phe Ser Pro
    130                 135                 140

Asp Pro Ala Leu Ser Gly Val Leu Phe Ala Glu Thr Ile Lys Gly Ile
145                 150                 155                 160

Gln Asp Ala Gly Val Val Ala Thr Ala Lys His Tyr Ile Ala Tyr Glu
                165                 170                 175

Gln Glu His Phe Arg Gln Ala Pro Glu Ala Gln Gly Phe Gly Phe Asn
            180                 185                 190

Ile Ser Glu Ser Gly Ser Ala Asn Leu Asp Asp Lys Thr Met His Glu
        195                 200                 205

Leu Tyr Leu Trp Pro Phe Ala Asp Ala Ile Arg Ala Gly Ala Gly Ala
    210                 215                 220

Val Met Cys Ser Tyr Asn Gln Ile Asn Asn Ser Tyr Gly Cys Gln Asn
```

-continued

```
            225                 230                 235                 240
Ser Tyr Thr Leu Asn Lys Leu Lys Ala Glu Leu Gly Phe Gln Gly
                245                 250                 255
Phe Val Met Ser Asp Trp Ala His His Ala Gly Val Ser Gly Ala
            260                 265                 270
Leu Ala Gly Leu Asp Met Ser Met Pro Gly Asp Val Asp Tyr Asp Ser
            275                 280                 285
Gly Thr Ser Tyr Trp Gly Thr Asn Leu Thr Ile Ser Val Leu Asn Gly
        290                 295                 300
Thr Val Pro Gln Trp Arg Val Asp Asp Met Ala Val Arg Ile Met Ala
305                 310                 315                 320
Ala Tyr Tyr Lys Val Gly Arg Asp Arg Leu Trp Thr Pro Asn Phe
                325                 330                 335
Ser Ser Trp Thr Arg Asp Glu Tyr Gly Tyr Lys Tyr Tyr Val Ser
                340                 345                 350
Glu Gly Pro Tyr Glu Lys Val Asn Gln Tyr Val Asn Val Gln Arg Asn
                355                 360                 365
His Ser Glu Leu Ile Arg Arg Ile Gly Ala Asp Ser Thr Val Leu Leu
        370                 375                 380
Lys Asn Asp Gly Ala Leu Pro Leu Thr Gly Lys Glu Arg Leu Val Ala
385                 390                 395                 400
Leu Ile Gly Glu Asp Ala Gly Ser Asn Pro Tyr Gly Ala Asn Gly Cys
                405                 410                 415
Ser Asp Arg Gly Cys Asp Asn Gly Thr Leu Ala Met Gly Trp Gly Ser
                420                 425                 430
Gly Thr Ala Asn Phe Pro Tyr Leu Val Thr Pro Glu Gln Ala Ile Ser
            435                 440                 445
Asn Glu Val Leu Lys His Lys Asn Gly Val Phe Thr Ala Thr Asp Asn
        450                 455                 460
Trp Ala Ile Asp Gln Ile Glu Ala Leu Ala Lys Thr Ala Ser Val Ser
465                 470                 475                 480
Leu Val Phe Val Asn Ala Asp Ser Gly Glu Gly Tyr Ile Asn Val Asp
                485                 490                 495
Gly Asn Leu Gly Asp Arg Arg Asn Leu Thr Leu Trp Arg Asn Gly Asp
                500                 505                 510
Asn Val Ile Lys Ala Ala Ala Ser Asn Cys Asn Asn Thr Ile Val Val
            515                 520                 525
Ile His Ser Val Gly Pro Val Leu Val Asn Glu Trp Tyr Asp Asn Pro
        530                 535                 540
Asn Val Thr Ala Ile Leu Trp Gly Gly Leu Pro Gly Gln Glu Ser Gly
545                 550                 555                 560
Asn Ser Leu Ala Asp Val Leu Tyr Gly Arg Val Asn Pro Gly Ala Lys
                565                 570                 575
Ser Pro Phe Thr Trp Gly Lys Thr Arg Glu Ala Tyr Gln Asp Tyr Leu
            580                 585                 590
Val Thr Glu Pro Asn Asn Gly Asn Gly Ala Pro Gln Glu Asp Phe Val
            595                 600                 605
Glu Gly Val Phe Ile Asp Tyr Arg Gly Phe Asp Lys Arg Asn Glu Thr
        610                 615                 620
Pro Ile Tyr Glu Phe Gly Tyr Gly Leu Ser Tyr Thr Thr Phe Asn Tyr
625                 630                 635                 640
Ser Asn Leu Glu Val Gln Val Leu Ser Ala Pro Ala Tyr Glu Pro Ala
                645                 650                 655
```

Ser Gly Glu Thr Glu Ala Ala Pro Thr Phe Gly Glu Val Gly Asn Ala
            660                 665                 670

Ser Asp Tyr Leu Tyr Pro Ser Gly Leu Leu Arg Ile Thr Lys Phe Ile
        675                 680                 685

Tyr Pro Trp Leu Asn Gly Thr Asp Leu Glu Ala Ser Ser Gly Asp Ala
        690                 695                 700

Ser Tyr Gly Gln Asp Ser Ser Asp Tyr Leu Pro Glu Gly Ala Thr Asp
705                 710                 715                 720

Gly Ser Ala Gln Pro Ile Leu Pro Ala Gly Gly Pro Gly Asn
            725                 730                 735

Pro Arg Leu Tyr Asp Glu Leu Ile Arg Val Ser Val Thr Ile Lys Asn
            740                 745                 750

Thr Gly Lys Val Ala Gly Asp Glu Val Pro Gln Leu Tyr Val Ser Leu
            755                 760                 765

Gly Gly Pro Asn Glu Pro Lys Ile Val Leu Arg Gln Phe Glu Arg Ile
        770                 775                 780

Thr Leu Gln Pro Ser Glu Glu Thr Lys Trp Ser Thr Thr Leu Thr Arg
785                 790                 795                 800

Arg Asp Leu Ala Asn Trp Asn Val Glu Lys Gln Asp Trp Glu Ile Thr
                805                 810                 815

Ser Tyr Pro Lys Met Val Phe Val Gly Ser Ser Arg Lys Leu Pro
            820                 825                 830

Leu Arg Ala Ser Leu Pro Thr Val His
        835                 840

<210> SEQ ID NO 15
<211> LENGTH: 3329
<212> TYPE: DNA
<213> ORGANISM: Artificial sequence
<220> FEATURE:
<223> OTHER INFORMATION: Sequence of recombinant construct expressing
      BGL1 protein fused to Cell signal peptide

<400> SEQUENCE: 15
gaattcccga tcctatctgt cacttcatca aaaggacagt agaaaaggaa ggtggcacta    60
caaatgccat cattgcgata aaggaaaggc tatcgttcaa gatgcctctg ccgacagtgg   120
tcccaaagat ggaccccac ccacgaggag catcgtggaa aagaagacg ttccaaccac    180 gtcttcaaag caagtggatt gatgtgatat ctccactgac gtaagggatg acgcacaatc   240
ccactatcct tcgcaagacc cttcctctat ataaggaagt tcatttcatt tggagaggac   300
aggcttcttg agatccttca acaattacca acaacaacaa acaacaaaca acattacaat   360
tactatttac aattacagtc gagggatct atggcgcgaa atccctaat tttcccggtg    420 attttgctcg ccgttcttct cttctctccg ccgatttact ccgccggtca cgattaccgc   480
gacgctctcc gtaaatctag catggctgat gaattggcct actccccacc gtattaccca   540
tccccttggg ccaatggcca gggcgactgg gcgcaggcat accagcgcgc tgttgatatt   600
gtctcgcaaa tgacattgga tgagaaggtc aatctgacca caggaactgg atgggaattg   660
gaactatgtg ttggtcagac tggcggtgtt ccccgattgg gagttccggg aatgtgttta   720
caggatagcc ctctgggcgt tcgcgactcc gactacaact ctgctttccc tgccggcatg   780
aacgtggctg cgacctggga caagaatctg gcataccttc gcggcaaggc tatgggtcag   840
gaatttagtg acaagggtgc cgatatccaa ttgggtccag ctgccggccc tctcggtaga   900
agtcccgacg gtggtcgtaa ctgggaggc ttctccccag accctgccct aagtggtgtg   960

```
ctctttgccg agaccatcaa gggtatccaa gatgctggtg tggttgcgac ggctaagcac    1020
tacattgctt acgagcaaga gcatttccgt caggcgcctg aagcccaagg ttttggattt    1080
aatatttccg agagtggaag tgcgaacctc gatgataaga ctatgcacga gctgtacctc    1140
tggcccttcg cggatgccat ccgtgcaggt gctggcgctg tgatgtgctc ctacaaccag    1200
atcaacaaca gttatggctg ccagaacagc tacactctga acaagctgct caaggccgag    1260
ctgggcttcc agggctttgt catgagtgat tgggctgctc accatgctgg tgtgagtggt    1320
gctttggcag gattggatat gtctatgcca ggagacgtcg actacgacag tggtacgtct    1380
tactggggta caaacttgac cattagcgtg ctcaacgaaa cggtgcccca atggcgtgtt    1440
gatgacatgg ctgtccgcat catggccgcc tactacaagg tcggccgtga ccgtctgtgg    1500
actcctccca acttcagctc atggaccaga gatgaatacg ctacaagta ctactacgtg     1560 tcggagggac cgtacgagaa ggtcaaccag tacgtgaatg tgcaacgcaa ccacagcgaa    1620
ctgattcgcc gcattggagc ggacagcacg gtgctcctca gaacgacgg cgctctgcct     1680 ttgactggta aggagcgcct ggtcgcgctt atcggagaag atgcgggctc caacccttat    1740
ggtgccaacg gctgcagtga ccgtggatgc gacaatggaa cattggcgat gggctgggga    1800
agtggtactg ccaacttccc atacctggtg accccgagc aggccatctc aaacgaggtg     1860
cttaagcaca agaatggtgt attcaccgcc accgataact gggctatcga tcaaattgag    1920
gcgcttgcta agaccgccag tgtctctctt gtctttgtca cgccgactc tggtgagggt     1980 tacatcaatg tggacggaaa cctgggtgac cgcaggaacc tgaccctgtg gaggaacggc    2040
gataatgtga tcaaggctgc tgctagcaac tgcaacaaca caatcgttgt cattcactct    2100
gtcggaccag tcttggttaa cgagtggtac gacaacccca atgttaccgc tatcctctgg    2160
ggtggtttgc ccggtcagga gtctggcaac tctcttgccg acgtcctcta tggccgtgtc    2220
aaccccggtg ccaagtcgcc ctttacctgg ggcaagactc gtgaggccta ccaagactac    2280
ttggtcaccg agcccaacaa cggcaacgga gcccctcagg aagactttgt cgagggcgtc    2340
ttcattgact accgtggatt tgacaagcgc aacgagaccc cgatctacga gttcggctat    2400
ggtctgagct acaccacttt caactactcg aaccttgagg tgcaggtgct gagcgcccct    2460
gcatacgagc ctgcttcggg tgagaccgag gcagcgccaa ccttcggaga ggttggaaat    2520
gcgtcggatt acctctaccc cagcggattg ctgagaatta ccaagttcat ctacccctgg    2580
ctcaacggta ccgatctcga ggcatcttcc ggggatgcta gctacgggca ggactcctcc    2640
gactatcttc ccgagggagc caccgatggc tctgcgcaac cgatcctgcc tgccggtggc    2700
ggtcctggcg gcaaccctcg cctgtacgac gagctcatcc gcgtgtcagt gaccatcaag    2760
aacaccggca aggttgctgg tgatgaagtt ccccaactgt atgtttccct tggcggtccc    2820
aatgagccca agatcgtgct gcgtcaattc gagcgcatca cgctgcagcc gtcggaggag    2880
acgaagtgga gcacgactct gacgcgccgt gaccttgcaa actggaatgt tgagaagcag    2940
gactgggaga ttacgtcgta tcccaagatg gtgtttgtcg gaagctcctc gcggaagctg    3000
ccgctccggg cgtctctgcc tactgttcac taacccgggc gagctcgaat tgatcgttca    3060
aacatttggc aataaagttt cttaagattg aatcctgttg ccggtcttgc gatgattatc    3120
atataatttc tgttgaatta cgttaagcat gtaataatta acatgtaat gcatgacgtt    3180 atttatgaga tggggttttt atgattaaga gtccccgcaa ttatacattt taatacgcga    3240
tagaaaaaca aaatatagcg cccaaactaa ggataaaatt attcgcgccg cggggggggca    3300
```
ttctatggtt actagatctc tagaattcc                                    3329

<210> SEQ ID NO 16
<211> LENGTH: 880
<212> TYPE: PRT
<213> ORGANISM: Artificial sequence
<220> FEATURE:
<223> OTHER INFORMATION: Sequence of recombinant BGL1 protein fused to
      Cel1 signal peptide

<400> SEQUENCE: 16

```
Met Ala Arg Lys Ser Leu Ile Phe Pro Val Ile Leu Ala Val Leu
1               5                   10                  15

Leu Phe Ser Pro Pro Ile Tyr Ser Ala Gly His Asp Tyr Arg Asp Ala
                20                  25                  30

Leu Arg Lys Ser Ser Met Ala Asp Glu Leu Ala Tyr Ser Pro Pro Tyr
                35                  40                  45

Tyr Pro Ser Pro Trp Ala Asn Gly Gln Gly Asp Trp Ala Gln Ala Tyr
            50                  55                  60

Gln Arg Ala Val Asp Ile Val Ser Gln Met Thr Leu Asp Glu Lys Val
65                  70                  75                  80

Asn Leu Thr Thr Gly Thr Gly Trp Glu Leu Glu Leu Cys Val Gly Gln
                85                  90                  95

Thr Gly Gly Val Pro Arg Leu Gly Val Pro Gly Met Cys Leu Gln Asp
                100                 105                 110

Ser Pro Leu Gly Val Arg Asp Ser Asp Tyr Asn Ser Ala Phe Pro Ala
                115                 120                 125

Gly Met Asn Val Ala Ala Thr Trp Asp Lys Asn Leu Ala Tyr Leu Arg
            130                 135                 140

Gly Lys Ala Met Gly Gln Glu Phe Ser Asp Lys Gly Ala Asp Ile Gln
145                 150                 155                 160

Leu Gly Pro Ala Ala Gly Pro Leu Gly Arg Ser Pro Asp Gly Gly Arg
                165                 170                 175

Asn Trp Glu Gly Phe Ser Pro Asp Pro Ala Leu Ser Gly Val Leu Phe
                180                 185                 190

Ala Glu Thr Ile Lys Gly Ile Gln Asp Ala Gly Val Val Ala Thr Ala
            195                 200                 205

Lys His Tyr Ile Ala Tyr Glu Gln Glu His Phe Arg Gln Ala Pro Glu
    210                 215                 220

Ala Gln Gly Phe Gly Phe Asn Ile Ser Glu Ser Gly Ser Ala Asn Leu
225                 230                 235                 240

Asp Asp Lys Thr Met His Glu Leu Tyr Leu Trp Pro Phe Ala Asp Ala
                245                 250                 255

Ile Arg Ala Gly Ala Gly Ala Val Met Cys Ser Tyr Asn Gln Ile Asn
            260                 265                 270

Asn Ser Tyr Gly Cys Gln Asn Ser Tyr Thr Leu Asn Lys Leu Leu Lys
    275                 280                 285

Ala Glu Leu Gly Phe Gln Gly Phe Val Met Ser Asp Trp Ala Ala His
    290                 295                 300

His Ala Gly Val Ser Gly Ala Leu Ala Gly Leu Asp Met Ser Met Pro
305                 310                 315                 320

Gly Asp Val Asp Tyr Asp Ser Gly Thr Ser Tyr Trp Gly Thr Asn Leu
                325                 330                 335

Thr Ile Ser Val Leu Asn Gly Thr Val Pro Gln Trp Arg Val Asp Asp
            340                 345                 350
```

```
Met Ala Val Arg Ile Met Ala Ala Tyr Tyr Lys Val Gly Arg Asp Arg
            355                 360                 365
Leu Trp Thr Pro Pro Asn Phe Ser Ser Trp Thr Arg Asp Glu Tyr Gly
        370                 375                 380
Tyr Lys Tyr Tyr Tyr Val Ser Glu Gly Pro Tyr Glu Lys Val Asn Gln
385                 390                 395                 400
Tyr Val Asn Val Gln Arg Asn His Ser Glu Leu Ile Arg Arg Ile Gly
                405                 410                 415
Ala Asp Ser Thr Val Leu Leu Lys Asn Asp Gly Ala Leu Pro Leu Thr
            420                 425                 430
Gly Lys Glu Arg Leu Val Ala Leu Ile Gly Glu Asp Ala Gly Ser Asn
        435                 440                 445
Pro Tyr Gly Ala Asn Gly Cys Ser Asp Arg Gly Cys Asp Asn Gly Thr
    450                 455                 460
Leu Ala Met Gly Trp Gly Ser Gly Thr Ala Asn Phe Pro Tyr Leu Val
465                 470                 475                 480
Thr Pro Glu Gln Ala Ile Ser Asn Glu Val Leu Lys His Lys Asn Gly
                485                 490                 495
Val Phe Thr Ala Thr Asp Asn Trp Ala Ile Asp Gln Ile Glu Ala Leu
            500                 505                 510
Ala Lys Thr Ala Ser Val Ser Leu Val Phe Val Asn Ala Asp Ser Gly
        515                 520                 525
Glu Gly Tyr Ile Asn Val Asp Gly Asn Leu Gly Asp Arg Arg Asn Leu
    530                 535                 540
Thr Leu Trp Arg Asn Gly Asp Asn Val Ile Lys Ala Ala Ala Ser Asn
545                 550                 555                 560
Cys Asn Asn Thr Ile Val Val Ile His Ser Val Gly Pro Val Leu Val
                565                 570                 575
Asn Glu Trp Tyr Asp Asn Pro Asn Val Thr Ala Ile Leu Trp Gly Gly
            580                 585                 590
Leu Pro Gly Gln Glu Ser Gly Asn Ser Leu Ala Asp Val Leu Tyr Gly
        595                 600                 605
Arg Val Asn Pro Gly Ala Lys Ser Pro Phe Thr Trp Gly Lys Thr Arg
    610                 615                 620
Glu Ala Tyr Gln Asp Tyr Leu Val Thr Glu Pro Asn Asn Gly Asn Gly
625                 630                 635                 640
Ala Pro Gln Glu Asp Phe Val Glu Gly Val Phe Ile Asp Tyr Arg Gly
                645                 650                 655
Phe Asp Lys Arg Asn Glu Thr Pro Ile Tyr Glu Phe Gly Tyr Gly Leu
            660                 665                 670
Ser Tyr Thr Thr Phe Asn Tyr Ser Asn Leu Glu Val Gln Val Leu Ser
        675                 680                 685
Ala Pro Ala Tyr Glu Pro Ala Ser Gly Glu Thr Glu Ala Ala Pro Thr
    690                 695                 700
Phe Gly Glu Val Gly Asn Ala Ser Asp Tyr Leu Tyr Pro Ser Gly Leu
705                 710                 715                 720
Leu Arg Ile Thr Lys Phe Ile Tyr Pro Trp Leu Asn Gly Thr Asp Leu
                725                 730                 735
Glu Ala Ser Ser Gly Asp Ala Ser Tyr Gly Gln Asp Ser Ser Asp Tyr
            740                 745                 750
Leu Pro Glu Gly Ala Thr Asp Gly Ser Ala Gln Pro Ile Leu Pro Ala
        755                 760                 765
Gly Gly Gly Pro Gly Gly Asn Pro Arg Leu Tyr Asp Glu Leu Ile Arg
```

```
                770                  775                  780
Val Ser Val Thr Ile Lys Asn Thr Gly Lys Val Ala Gly Asp Glu Val
785                  790                  795                  800

Pro Gln Leu Tyr Val Ser Leu Gly Gly Pro Asn Glu Pro Lys Ile Val
                805                  810                  815

Leu Arg Gln Phe Glu Arg Ile Thr Leu Gln Pro Ser Glu Thr Lys
            820                  825                  830

Trp Ser Thr Thr Leu Thr Arg Arg Asp Leu Ala Asn Trp Asn Val Glu
            835                  840                  845

Lys Gln Asp Trp Glu Ile Thr Ser Tyr Pro Lys Met Val Phe Val Gly
        850                  855                  860

Ser Ser Ser Arg Lys Leu Pro Leu Arg Ala Ser Leu Pro Thr Val His
865                  870                  875                  880

<210> SEQ ID NO 17
<211> LENGTH: 4
<212> TYPE: PRT
<213> ORGANISM: Artificial sequence
<220> FEATURE:
<223> OTHER INFORMATION: ER retainig signal peptide

<400> SEQUENCE: 17

His Asp Glu Leu
1

<210> SEQ ID NO 18
<211> LENGTH: 3288
<212> TYPE: DNA
<213> ORGANISM: Artificial sequence
<220> FEATURE:
<223> OTHER INFORMATION: Sequence of recombinant construct expressing
      BGL1 protein fused to Cel1 and ER retaining signal peptides

<400> SEQUENCE: 18
gaattcccga tcctatctgt cacttcatca aaaggacagt agaaaaggaa ggtggcacta      60
caaatgccat cattgcgata aaggaaaggc tatcgttcaa gatgcctctg ccgacagtgg     120
tcccaaagat ggaccccac ccacgaggag catcgtggaa aagaagacg ttccaaccac       180 gtcttcaaag caagtggatt gatgtgatat ctccactgac gtaagggatg acgcacaatc    240
ccactatcct tcgcaagacc cttcctctat ataaggaagt tcatttcatt tggagaggac    300
aggcttcttg agatccttca acaattacca caacaacaa acaacaaaca acattacaat     360
tactatttac aattacagtc gagggatct atggcgcgaa atccctaat tttcccggtg     420 attttgctcg ccgttcttct cttctctccg ccgatttact ccgccggtca cgattaccgc     480
gacgctctcc gtaaatctag catggctgat gaattggcct actccccacc gtattaccca    540
tccccttggg ccaatggcca gggcgactgg gcgcaggcat accagcgcgc tgttgatatt    600
gtctcgcaaa tgacattgga tgagaaggtc aatctgacca caggaactgg atgggaattg    660
gaactatgtg ttggtcagac tggcggtgtt ccccgattgg gagttccggg aatgtgttta    720
caggatagcc ctctgggcgt tcgcgactcc gactacaact ctgctttccc tgccggcatg    780
aacgtggctg cgacctggga caagaatctg gcataccttc gcggcaaggc tatgggtcag    840
gaatttagtg acaagggtgc cgatatccaa ttgggtccag ctgccggccc tctcggtaga    900
agtcccgacg gtggtcgtaa ctgggagggc ttctccccag accctgccct aagtggtgtg    960 ctcttttgccg agaccatcaa gggtatccaa gatgctggtg tggttgcgac ggctaagcac    1020
tacattgctt acgagcaaga gcatttccgt caggcgcctg aagcccaagg ttttggattt    1080
```

-continued

```
aatatttccg agagtggaag tgcgaacctc gatgataaga ctatgcacga gctgtacctc    1140
tggcccttcg cggatgccat ccgtgcaggt gctggcgctg tgatgtgctc ctacaaccag    1200
atcaacaaca gttatggctg ccagaacagc tacactctga acaagctgct caaggccgag    1260
ctgggcttcc agggctttgt catgagtgat tgggctgctc accatgctgg tgtgagtggt    1320
gctttggcag gattggatat gtctatgcca ggagacgtcg actacgacag tggtacgtct    1380
tactggggta caaacttgac cattagcgtg ctcaacgaaa cggtgcccca atggcgtgtt    1440
gatgacatgg ctgtccgcat catggccgcc tactacaagg tcggccgtga ccgtctgtgg    1500
actcctccca acttcagctc atggaccaga gatgaatacg ctacaagta ctactacgtg    1560 tcggagggac cgtacgagaa ggtcaaccag tacgtgaatg tgcaacgcaa ccacagcgaa    1620
ctgattcgcc gcattggagc ggacagcacg gtgctcctca agaacgacgg cgctctgcct    1680
ttgactggta aggagcgcct ggtcgcgctt atcggagaag atgcgggctc caacccttat    1740
ggtgccaacg gctgcagtga ccgtggatgc gacaatggaa cattggcgat gggctgggga    1800
agtggtactg ccaacttccc atacctggtg accccgagc aggccatctc aaacgaggtg    1860
cttaagcaca agaatggtgt attcaccgcc accgataact gggctatcga tcaaattgag    1920
gcgcttgcta agaccgccag tgtctctctt gtctttgtca acgccgactc tggtgagggt    1980
tacatcaatg tggacggaaa cctgggtgac cgcaggaacc tgaccctgtg gaggaacggc    2040
gataatgtga tcaaggctgc tgctagcaac tgcaacaaca caatcgttgt cattcactct    2100
gtcggaccag tcttggttaa cgagtggtac gacaaccca atgttaccgc tatcctctgg    2160
ggtggtttgc ccggtcagga gtctggcaac tctcttgccg acgtcctcta tggccgtgtc    2220
aaccccggtg ccaagtcgcc ctttacctgg ggcaagactc gtgaggccta ccaagactac    2280
ttggtcaccg agcccaacaa cggcaacgga gccctcagg aagactttgt cgagggcgtc    2340
ttcattgact accgtggatt tgacaagcgc aacgagaccc cgatctacga gttcggctat    2400
ggtctgagct acaccacttt caactactcg aaccttgagg tgcaggtgct gagcgcccct    2460
gcatacgagc ctgcttcggg tgagaccgag gcagcgccaa ccttcggaga ggttggaaat    2520
gcgtcggatt acctctaccc cagcggattg ctgagaatta ccaagttcat ctaccctgg    2580 ctcaacggta ccgatctcga ggcatcttcc ggggatgcta gctacgggca ggactcctcc    2640
gactatcttc ccgagggagc caccgatggc tctgcgcaac cgatcctgcc tgccggtggc    2700
ggtcctggcg gcaaccctcg cctgtacgac gagctcatcc gcgtgtcagt gaccatcaag    2760
aacaccggca aggttgctgg tgatgaagtt ccccaactgt atgtttccct tggcggtccc    2820
aatgagccca gatcgtgct gcgtcaattc gagcgcatca cgctgcagcc gtcggaggag    2880
acgaagtgga gcacgactct gacgcgccgt gaccttgcaa actggaatgt tgagaagcag    2940
gactgggaga ttcgtcgta tcccaagatg gtgtttgtcg aagctcctc gcggaagctg    3000 ccgctccggg cgtctctgcc tactgttcat gatgaacttt aacccgggcg agctcgaatt    3060
gatcgttcaa acatttggca ataaagtttc ttaagattga gttaagcatg taataattaa    3120
acatgtaatg catgacgtta tttatgagat ggggttttta tgattaagag tccccgcaat    3180
tatacatttt aatacgcgat agaaaaacaa aatatagcgc ccaaactaag gataaaatta    3240
ttcgcgccgc gggggggcat tctatggtta ctagatctct agaattcc    3288
```

<210> SEQ ID NO 19
<211> LENGTH: 883
<212> TYPE: PRT

```
<213> ORGANISM: Artificial sequence
<220> FEATURE:
<223> OTHER INFORMATION: Sequence of recombinant BGL1 protein fused to
      Cel1 and ER retaining signal peptides

<400> SEQUENCE: 19
```

| | | | | | | | | | | | | | | |
|---|---|---|---|---|---|---|---|---|---|---|---|---|---|---|
| Met | Ala | Arg | Lys | Ser | Leu | Ile | Phe | Pro | Val | Ile | Leu | Ala | Val | Leu |
| 1 | | | | 5 | | | | | 10 | | | | | 15 |
| Leu | Phe | Ser | Pro | Pro | Ile | Tyr | Ser | Ala | Gly | His | Asp | Tyr | Arg | Asp | Ala |
| | | | 20 | | | | | 25 | | | | | 30 | | |
| Leu | Arg | Lys | Ser | Ser | Met | Ala | Asp | Glu | Leu | Ala | Tyr | Ser | Pro | Pro | Tyr |
| | | 35 | | | | | 40 | | | | | 45 | | | |
| Tyr | Pro | Ser | Pro | Trp | Ala | Asn | Gly | Gln | Gly | Asp | Trp | Ala | Gln | Ala | Tyr |
| | 50 | | | | | 55 | | | | | 60 | | | | |
| Gln | Arg | Ala | Val | Asp | Ile | Val | Ser | Gln | Met | Thr | Leu | Asp | Glu | Lys | Val |
| 65 | | | | | 70 | | | | | 75 | | | | | 80 |
| Asn | Leu | Thr | Thr | Gly | Thr | Gly | Trp | Glu | Leu | Glu | Leu | Cys | Val | Gly | Gln |
| | | | | 85 | | | | | 90 | | | | | 95 | |
| Thr | Gly | Gly | Val | Pro | Arg | Leu | Gly | Val | Pro | Gly | Met | Cys | Leu | Gln | Asp |
| | | | 100 | | | | | 105 | | | | | 110 | | |
| Ser | Pro | Leu | Gly | Val | Arg | Asp | Ser | Asp | Tyr | Asn | Ser | Ala | Phe | Pro | Ala |
| | | | 115 | | | | | 120 | | | | | 125 | | |
| Gly | Met | Asn | Val | Ala | Ala | Thr | Trp | Asp | Lys | Asn | Leu | Ala | Tyr | Leu | Arg |
| | | 130 | | | | | 135 | | | | | 140 | | | |
| Gly | Lys | Ala | Met | Gly | Gln | Glu | Phe | Ser | Asp | Lys | Gly | Ala | Asp | Ile | Gln |
| 145 | | | | | 150 | | | | | 155 | | | | | 160 |
| Leu | Gly | Pro | Ala | Ala | Gly | Pro | Leu | Gly | Arg | Ser | Pro | Asp | Gly | Gly | Arg |
| | | | | 165 | | | | | 170 | | | | | 175 | |
| Asn | Trp | Glu | Gly | Phe | Ser | Pro | Asp | Pro | Ala | Leu | Ser | Gly | Val | Leu | Phe |
| | | | | 180 | | | | | 185 | | | | | 190 | |
| Ala | Glu | Thr | Ile | Lys | Gly | Ile | Gln | Asp | Ala | Gly | Val | Val | Ala | Thr | Ala |
| | | | 195 | | | | | 200 | | | | | 205 | | |
| Lys | His | Tyr | Ile | Ala | Tyr | Glu | Gln | Glu | His | Phe | Arg | Gln | Ala | Pro | Glu |
| | | 210 | | | | | 215 | | | | | 220 | | | |
| Ala | Gln | Gly | Phe | Gly | Phe | Asn | Ile | Ser | Glu | Ser | Gly | Ser | Ala | Asn | Leu |
| 225 | | | | | 230 | | | | | 235 | | | | | 240 |
| Asp | Asp | Lys | Thr | Met | His | Glu | Leu | Tyr | Leu | Trp | Pro | Phe | Ala | Asp | Ala |
| | | | | 245 | | | | | 250 | | | | | 255 | |
| Ile | Arg | Ala | Gly | Ala | Gly | Ala | Val | Met | Cys | Ser | Tyr | Asn | Gln | Ile | Asn |
| | | | | 260 | | | | | 265 | | | | | 270 | |
| Asn | Ser | Tyr | Gly | Cys | Gln | Asn | Ser | Tyr | Thr | Leu | Asn | Lys | Leu | Leu | Lys |
| | | | 275 | | | | | 280 | | | | | 285 | | |
| Ala | Glu | Leu | Gly | Phe | Gln | Gly | Phe | Val | Met | Ser | Asp | Trp | Ala | Ala | His |
| | | | 290 | | | | | 295 | | | | | 300 | | |
| His | Ala | Gly | Val | Ser | Gly | Ala | Leu | Ala | Gly | Leu | Asp | Met | Ser | Met | Pro |
| 305 | | | | | 310 | | | | | 315 | | | | | 320 |
| Gly | Asp | Val | Asp | Tyr | Asp | Ser | Gly | Thr | Ser | Tyr | Trp | Gly | Thr | Asn | Leu |
| | | | | 325 | | | | | 330 | | | | | 335 | |
| Thr | Ile | Ser | Val | Leu | Asn | Gly | Thr | Val | Pro | Gln | Trp | Arg | Val | Asp | Asp |
| | | | 340 | | | | | 345 | | | | | 350 | | |
| Met | Ala | Val | Arg | Ile | Met | Ala | Ala | Tyr | Tyr | Lys | Val | Gly | Arg | Asp | Arg |
| | | | 355 | | | | | 360 | | | | | 365 | | |
| Leu | Trp | Thr | Pro | Pro | Asn | Phe | Ser | Ser | Trp | Thr | Arg | Asp | Glu | Tyr | Gly |
| | | 370 | | | | | 375 | | | | | 380 | | | |

-continued

```
Tyr Lys Tyr Tyr Tyr Val Ser Glu Gly Pro Tyr Glu Lys Val Asn Gln
385                 390                 395                 400

Tyr Val Asn Val Gln Arg Asn His Ser Glu Leu Ile Arg Arg Ile Gly
            405                 410                 415

Ala Asp Ser Thr Val Leu Leu Lys Asn Asp Gly Ala Leu Pro Leu Thr
        420                 425                 430

Gly Lys Glu Arg Leu Val Ala Leu Ile Gly Glu Asp Ala Gly Ser Asn
            435                 440                 445

Pro Tyr Gly Ala Asn Gly Cys Ser Asp Arg Gly Cys Asp Asn Gly Thr
        450                 455                 460

Leu Ala Met Gly Trp Gly Ser Gly Thr Ala Asn Phe Pro Tyr Leu Val
465                 470                 475                 480

Thr Pro Glu Gln Ala Ile Ser Asn Glu Val Leu Lys His Lys Asn Gly
            485                 490                 495

Val Phe Thr Ala Thr Asp Asn Trp Ala Ile Asp Gln Ile Glu Ala Leu
        500                 505                 510

Ala Lys Thr Ala Ser Val Ser Leu Val Phe Val Asn Ala Asp Ser Gly
            515                 520                 525

Glu Gly Tyr Ile Asn Val Asp Gly Asn Leu Gly Asp Arg Arg Asn Leu
        530                 535                 540

Thr Leu Trp Arg Asn Gly Asp Asn Val Ile Lys Ala Ala Ala Ser Asn
545                 550                 555                 560

Cys Asn Asn Thr Ile Val Val Ile His Ser Val Gly Pro Val Leu Val
            565                 570                 575

Asn Glu Trp Tyr Asp Asn Pro Asn Val Thr Ala Ile Leu Trp Gly Gly
        580                 585                 590

Leu Pro Gly Gln Glu Ser Gly Asn Ser Leu Ala Asp Val Leu Tyr Gly
            595                 600                 605

Arg Val Asn Pro Gly Ala Lys Ser Pro Phe Thr Trp Gly Lys Thr Arg
        610                 615                 620

Glu Ala Tyr Gln Asp Tyr Leu Val Thr Glu Pro Asn Asn Gly Asn Gly
625                 630                 635                 640

Ala Pro Gln Glu Asp Phe Val Glu Gly Val Phe Ile Asp Tyr Arg Gly
            645                 650                 655

Phe Asp Lys Arg Asn Glu Thr Pro Ile Tyr Glu Phe Gly Tyr Gly Leu
        660                 665                 670

Ser Tyr Thr Thr Phe Asn Tyr Ser Asn Leu Glu Val Gln Val Leu Ser
            675                 680                 685

Ala Pro Ala Tyr Glu Pro Ala Ser Gly Glu Thr Glu Ala Ala Pro Thr
690                 695                 700

Phe Gly Glu Val Gly Asn Ala Ser Asp Tyr Leu Tyr Pro Ser Gly Leu
705                 710                 715                 720

Leu Arg Ile Thr Lys Phe Ile Tyr Pro Trp Leu Asn Gly Thr Asp Leu
            725                 730                 735

Glu Ala Ser Ser Gly Asp Ala Ser Tyr Gly Gln Asp Ser Ser Asp Tyr
        740                 745                 750

Leu Pro Glu Gly Ala Thr Asp Gly Ser Ala Gln Pro Ile Leu Pro Ala
            755                 760                 765

Gly Gly Gly Pro Gly Gly Asn Pro Arg Leu Tyr Asp Glu Leu Ile Arg
        770                 775                 780

Val Ser Val Thr Ile Lys Asn Thr Gly Lys Val Ala Gly Asp Glu Val
785                 790                 795                 800

Pro Gln Leu Tyr Val Ser Leu Gly Gly Pro Asn Glu Pro Lys Ile Val
```

-continued

```
                805                 810                 815
Leu Arg Gln Phe Glu Arg Ile Thr Leu Gln Pro Ser Glu Glu Thr Lys
            820                 825                 830

Trp Ser Thr Thr Leu Thr Arg Arg Asp Leu Ala Asn Trp Asn Val Glu
            835                 840                 845

Lys Gln Asp Trp Glu Ile Thr Ser Tyr Pro Lys Met Val Phe Val Gly
        850                 855                 860

Ser Ser Ser Arg Lys Leu Pro Leu Arg Ala Ser Leu Pro Thr Val His
865                 870                 875                 880

Asp Glu Leu

<210> SEQ ID NO 20
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 20
cagtgaccgt ggatgcgaca atg                                              23

<210> SEQ ID NO 21
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 21
agagacggat gacaagtact acttgaaatt gggcccaaaa                             40

<210> SEQ ID NO 22
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 22
cagtgaccgt ggatgcgaca atg                                              23

<210> SEQ ID NO 23
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 23
aaaggatcct tagtgaacag taggcagaga cgc                                   33

<210> SEQ ID NO 24
<211> LENGTH: 4
<212> TYPE: PRT
<213> ORGANISM: Artificial sequence
<220> FEATURE:
<223> OTHER INFORMATION: ER retaining signal peptide

<400> SEQUENCE: 24

Lys Asp Glu Leu
1
```

METHOD OF PRODUCING RECOMBINANT *ASPERGILLUS NIGER* β-GLUCOSIDASE AND AN AROMA SPREADING PLANT

RELATED APPLICATIONS

This application is a National Phase of PCT Patent Application No. PCT/IL00/00758, filed on Nov. 15, 2000, which is a continuation of U.S. patent application Ser. No. 09/443,338, filed on Nov. 19, 1999 now abandoned. The contents of the above applications are all incorporated by reference.

FIELD AND BACKGROUND OF THE INVENTION

The present invention relates to a polypeptide having β-glucosidase enzymatic activity, to a polynucleotide encoding the polypeptide, to nucleic acid constructs carrying the polynucleotide, to transformed or infected cells, such as yeast cells, and organisms expressing the polynucleotide and to various uses of the polypeptide, the polynucleotide, cells and/or organisms, including, but not limited to, producing a recombinant polypeptide having β-glucosidase enzymatic activity, increasing the level of aroma compounds in alcoholic beverages, as well as other fermentation products of plant material, hydrolyzing cellobiose and thus increasing the level of fermentable glucose, to increase production of alcohol, such as ethanol from plant material, increasing the aroma released from a plant or a plant product, and hydrolysis or transglycosylation of glycosides.

Abbreviations used herein include: BGL1—*Aspergillus niger* B1 β-glucosidase; bgl1—a cDNA encoding same; 2FGlcF—2-deoxy-2-fluoro β-glucosyl fluoride; DNP—2,4-dinitrophenol; DNPGlc—2,4-dinitrophenyl β-D-glucopyranoside; pNP—p-nitrophenol; pNPGlc—p-nitrophenyl β-D-glucopyranoside; MUGlc—4-methylumbeliferyl-β-D-glucopyranoside; YNB—yeast nitrogen base without amino acids; and X-glu—5-bromo-4-chloro-3-indolyl β-D-glucopyranoside.

β-Glucosidases (EC 3.2.1.21; β-D-glucoside glucohydrolase) play a number of different important roles in biology, including the degradation of cellulosic biomass by fungi and bacteria, degradation of glycolipids in mammalian lysosomes and the cleavage of glucosylated flavonoids in plants. These enzymes are therefore of considerable industrial interest, not only as constituents of cellulose-degrading systems, but also in the food industry (2, 3).

*Aspergillus* species are known as a useful source of β-glucosidases (4-6), and *Aspergillus niger* is by far the most efficient producer of β-glucosidase among the microorganisms investigated (4). Shoseyov et al. (7) have previously described a β-glucosidase from *Aspergillus niger* B1 (CMI CC 324626) which is active at low pHs, as well as in the presence of high ethanol concentrations. This enzyme effectively hydrolyzes flavor-compound glycosides in certain low-pH products, such as wine and passion fruit juice, thereby enhancing their flavor (8-12), and is particularly attractive for use in the food industry, as *A. niger* is considered non-toxic (3). In addition, β-glucosidase was found useful in enzymatic synthesis of glycosides (13-15). Other *A. niger* β-glucosidases have also been purified (16-18), however, differences in their properties have been reported, including ranges of molecular weights (116-137 kDa), isoelectric points (pI values of 3.8-4) and pH optima (3.4-4.5). Indeed, at least two β-glucosidases, with distinct substrate specificities, have been identified in commercial *A. niger* β-glucosidase preparations (19). Attempts to clear this confusion by cloning and expression of a functional *A. niger* β-glucosidase gene in *S. cerevisiae* has been previously reported (20), however the protein was not characterized, and the sequence was not published.

Glycosidases have been assigned to families on the basis of sequence similarities, there now being some 77 different such families defined containing over 2,000 different enzymes (21, see also the CAZy (Carbohydrate Active EnZymes) website, at the Architecture of Fonction de Macromolecules Biologiques of the Centre National de la Recherche Scientifique website. With the exception of the glucosylceramidases (Family 30), all simple β-glucosidases belong to either Family 1 or 3. Family 1 contains enzymes from bacteria, plants and mammals, including also 6-phospho-glucosidases and thioglucosidases. Furthermore, most Family 1 enzymes also have significant galactosidase activity. Family 3 contains β-glucosidases and hexosaminidases of fungal, bacterial and plant origin. Enzymes of both families hydrolyze their substrates with net retention of anomeric configuration, presumably via a two-step, double-displacement mechanism, involving two key active site carboxylic acid residues (for reviews of mechanism, see 22-24). In the first step, one of the carboxylic acids (the nucleophile) attacks at the substrate anomeric center, while the other (the acid/base catalyst) protonates the glycosidic oxygen, thereby assisting the departure of the aglycone. This results in the formation of a covalent α-glycosyl-enzyme intermediate. In a second step this intermediate is hydrolyzed by general base-catalyzed attack of water at the anomeric center of the glycosyl-enzyme, to release the β-glucose product and regenerate free enzyme. Both the formation and the hydrolysis of this intermediate proceed via transition states with substantial oxocarbenium ion character.

Given that Family 3 contains fungal enzymes of similar mass, including those from other *Aspergillus* sp., it is likely that the *Aspergillus niger* β-glucosidase would be a member of this family. Mechanistic information on this family is relatively sparse: the best characterized being the glycosylated 170 kDa β-glucosidase from *Aspergillus wentii*. By labeling the active site with conduritol B-epoxide, this enzyme was shown to carry out hydrolysis, with net retention of anomeric configuration. This study has demonstrated that the labeled aspartic acid residue was the same as that derivatized by the slow substrate D-glucal (1, 25). Furthermore, it was shown that the 2-deoxyglucosyl-enzyme, trapped by use of D-glucal, was kinetically identical to that formed during the hydrolysis of PNP-2-deoxy-β-D-glucopyranoside (26). Further detailed kinetic analysis of the enzyme was performed by Legler et al. (27), including measurement of Hammett relationships, kinetic isotope effects and studies of the binding of potent reversible inhibitors, such as gluconolactone and nojirimycin.

While reducing the present invention to practice, the β-glucosidase protein was isolated from *Aspergillus niger*, purified, cloned, sequenced, expressed in yeast host cells and its enzymatic function characterized. In addition, the protein as well as signal peptide fused thereto and optionally an endoplasmic reticulum retaining peptide fused thereto were expressed in transgenic plants and the release of aroma substances therefrom following homogenization monitored. The enzyme encoded by the isolated gene, as described above, is of known usefulness in plant and/or plant products, as well as in biotechnological processes, including the food industry. Several unexpected advantages were uncovered, including, but not limited to, pH and temperature stability of the β-glucosidase from *Aspergillus niger*, requirement for a signal peptide for obtaining catalytic activity when expressed in plants. Advantage for an endoplasmic retaining peptide or for a lack thereof when expressed in plants, depending on the application.

SUMMARY OF THE INVENTION

According to one aspect of the present invention there is provided an isolated nucleic acid comprising a genomic, complementary or composite polynucleotide preferably being derived from *Aspergillus niger*, encoding a polypeptide having a β-glucosidase catalytic activity and preferably further encoding, in frame, a signal peptide and an endoplasmic reticulum retaining peptide.

According to another aspect of the present invention there is provided a recombinant protein comprising a polypeptide having a β-glucosidase catalytic activity, the polypeptide is preferably derived from *Aspergillus niger* and it preferably fused to a signal peptide and optionally also to an endoplasmic reticulum retaining peptide.

According to yet another aspect of the present invention there is provided a nucleic acid construct comprising the isolated nucleic acid described herein.

According to still another aspect of the present invention there is provided host cell or an organism, such as a plant, comprising the nucleic acid or nucleic acid construct described herein.

According to further features in preferred embodiments of the invention described below, the polynucleotide is as set forth in SEQ ID NOs:1, 3 or a portion thereof.

According to still further features in the described preferred embodiments, the nucleic acid construct further comprising at least one cis acting control element for regulating expression of the polynucleotide.

According to still further features in the described preferred embodiments, the host cell is selected from the group consisting of a prokaryotic cell and a eukaryotic cell.

According to still further features in the described preferred embodiments the prokaryotic cell is *E. coli*.

According to still further features in the described preferred embodiments the eukaryotic cell is selected from the group consisting of a yeast cell, a fungous cell, a plant cell and an animal cell.

According to still further features in the described preferred embodiments the polypeptide is as set forth in SEQ ID NO: 2 or a portion thereof having the β-glucosidase catalytic activity.

According to an additional aspect of the present invention there is provided a method of producing recombinant β-glucosidase, the method comprising the step of introducing, in an expressible form, a nucleic acid construct into a host cell, the nucleic acid construct including a genomic, complementary or composite polynucleotide preferably derived from *Aspergillus niger*, encoding a polypeptide having a β-glucosidase catalytic activity and preferably further encoding, in frame, a signal peptide and an endoplasmic reticulum retaining peptide.

According to further features in preferred embodiments of the invention described below, the method further comprising the step of extracting the polypeptide having the β-glucosidase catalytic activity.

According to yet an additional aspect of the present invention there is provided a method of producing a recombinant β-glucosidase overexpressing cell, the method comprising the step of introducing, in an overexpressible form, a nucleic acid construct into a host cell, the nucleic acid construct including a genomic, complementary or composite polynucleotide preferably derived from *Aspergillus niger*, encoding a polypeptide having a β-glucosidase catalytic activity and preferably further encoding, in frame, a signal peptide and an endoplasmic reticulum retaining peptide.

According to still an additional aspect of the present invention there is provided a method of increasing a level of at least one fermentation substance in a fermentation product, the method comprising the step of fermenting a glucose containing fermentation starting material by a yeast cell overexpressing a nucleic acid construct including a genomic, complementary or composite polynucleotide being preferably derived from *Aspergillus niger*, encoding a polypeptide having a β-glucosidase catalytic activity and preferably further encoding, in frame, a signal peptide and an endoplasmic reticulum retaining peptide, thereby increasing the level of the at least one fermentation substance in the fermentation product.

According to a further aspect of the present invention there is provided a method of increasing a level of at least one fermentation substance in a fermentation product, the method comprising the step of fermenting a plant derived glucose containing fermentation starting material by a yeast cell, the plant overexpressing a nucleic acid construct including a genomic, complementary or composite polynucleotide preferably derived from *Aspergillus niger*, encoding a polypeptide having a β-glucosidase catalytic activity and preferably further encoding, in frame, a signal peptide and an endoplasmic reticulum retaining peptide, thereby increasing the level of the at least one fermentation substance in the fermentation product.

According to a further aspect of the present invention there is provided a method of increasing a level of at least one aroma substance in a plant derived product, the method comprising the step of incubating a glucose containing plant starting material with a yeast cell overexpressing a nucleic acid construct including a genomic, complementary or composite polynucleotide preferably derived from *Aspergillus niger*, encoding a polypeptide having a β-glucosidase catalytic activity and preferably further encoding, in frame, a signal peptide and an endoplasmic reticulum retaining peptide, thereby increasing the level of the at least one aroma substance in the plant derived product.

According to yet a further aspect of the present invention there is provided a method of increasing a level of at least one aroma substance in a plant derived product, the method comprising the step of incubating a glucose containing plant starting material with a yeast cell, said plant overexpressing a nucleic acid construct including a genomic, complementary or composite polynucleotide preferably derived from *Aspergillus niger*, encoding a polypeptide having a β-glucosidase catalytic activity and preferably further encoding, in frame, a signal peptide and an endoplasmic reticulum retaining peptide, thereby increasing the level of the at least one aroma substance in the plant derived product.

According to still further features in the described preferred embodiments the plant derived product is a fermentation product, such as, but not limited to, an alcoholic beverage.

According to still a further aspect of the present invention there is provided a method of increasing a level of free glucose in a glucose containing fermentation starting material, the method comprising the step of fermenting the glucose containing fermentation starting material by a cell overexpressing a nucleic acid construct including a genomic, complementary or composite polynucleotide preferably derived from *Aspergillus niger*, encoding a polypeptide having a β-glucosidase catalytic activity and preferably further encoding, in frame, a signal peptide and an endoplasmic reticulum retaining peptide, thereby increasing the level of the free glucose in the glucose containing fermentation starting material.

According to another aspect of the present invention there is provided a method of increasing a level of free glucose in a plant derived glucose containing fermentation starting material, the method comprising the step of fermenting the plant derived glucose containing fermentation starting material by a cell, the plant overexpressing a nucleic acid construct including a genomic, complementary or composite polynucleotide preferably derived from *Aspergillus niger*, encoding a polypeptide having a β-glucosidase catalytic activity and preferably further encoding, in frame, a signal peptide and an endoplasmic reticulum retaining peptide, thereby increasing the level of the free glucose in the plant.

According to yet another aspect of the present invention there is provided a method of increasing a level of free glucose in a plant, the method comprising the step of overexpressing in the plant a nucleic acid construct including a genomic, complementary or composite polynucleotide preferably derived from *Aspergillus niger*, encoding a polypeptide having a β-glucosidase catalytic activity and preferably further encoding, in frame, a signal peptide and an endoplasmic reticulum retaining peptide, thereby increasing the level of the free glucose in the plant.

According to still another aspect of the present invention there is provided a method of producing an alcohol, the method comprising the step of fermenting a glucose containing fermentation starting material by a cell overexpressing a nucleic acid construct including a genomic, complementary or composite polynucleotide preferably derived from *Aspergillus niger*, encoding a polypeptide having a β-glucosidase catalytic activity and preferably further encoding, in frame, a signal peptide and an endoplasmic reticulum retaining peptide, and extracting the alcohol therefrom.

According to an additional aspect of the present invention there is provided a method of producing an alcohol, the method comprising the step of fermenting a plant derived glucose containing fermentation starting material by a cell, the plant overexpressing a nucleic acid construct including a genomic, complementary or composite polynucleotide preferably derived from *Aspergillus niger*, encoding a polypeptide having a β-glucosidase catalytic activity and preferably further encoding, in frame, a signal peptide and an endoplasmic reticulum retaining peptide, and extracting the alcohol therefrom.

According to an additional aspect of the present invention there is provided a method of producing an aroma sp reading plant, the method comprising the step of overexpressing in the plant a nucleic acid construct including a genomic, complementary or composite polynucleotide preferably derived from *Aspergillus niger*, encoding a polypeptide having a β-glucosidase catalytic activity and preferably further encoding, in frame, a signal peptide and an endoplasmic reticulum retaining peptide, thereby increasing aroma spread from the plant.

According to further features in preferred embodiments of the invention described below, overexpressing the nucleic acid construct is performed in a tissue specific manner.

According to still further features in the described preferred embodiments overexpressing the nucleic acid construct is limited to at least one tissue selected from the group consisting of flower, fruit, seed, root, stem, pollen and leaves.

The present invention successfully addresses the shortcomings of the presently known configurations by providing a polypeptide having β-glucosidase enzymatic activity, a polynucleotide encoding the polypeptide, a nucleic acid constructs carrying the polynucleotide, transformed or infected cells, such as yeast cells, and organisms expressing the polynucleotide and various uses of the polypeptide, the polynucleotide, cells and/or organisms, including, but not limited to, producing a recombinant polypeptide having β-glucosidase enzymatic activity, increasing the level of aroma compounds in alcoholic beverages, as well as other fermentation products of plant material, hydrolyzing cellobiose and thus increasing the level of fermentable and/or free glucose, to increase production of a fermentation product, such as ethanol from plant material, increasing the aroma released from a plant or a plant product, and hydrolysis or transglycosylation of glycosides.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a-E. coli expression vector containing bgl1 cDNA, inserted into the NcoI/BamHI sites of pET3d. FIG. 1b—*S. cerevisiae* expression vector containing bgl1 cDNA, inserted into the HindIII/BamHI sites of pYES2-bgl1 plasmid. FIG. 1c—*P. pastoris* expression vector containing bgl1 cDNA, inserted into the EcoRI/BamHI sites of pHIL-S1.

FIG. 5a demonstrates the DNA (SEQ ID NO: 3) and amino acid (SEQ ID NO: 2) sequences of bgl1. Amino acid sequences determined by Edman degradation are underlined. DNA sequences of introns are underlined. Signal peptide is indicated by italic letters.

FIG. 5b. demonstrates bgl1 gene organization. Exons (E1-7) are indicated by filled boxes, introns by solid lines, restriction sites and the stop codon by arrows.

FIGS. 11a-c show schematic depictions of expression cassettes used for expression of A. niger β-glucosidase in tobacco plants. FIG. 11a—a cassette encoding BGL1 without a signal peptide (see, SEQ ID NO:13 for the nucleotide sequence and SEQ ID NO:14 for the amino acid sequence); FIG. 11b—a cassette encoding a BGL1 fused to a Cel1 signal peptide for secretion into the apoplast (see, SEQ ID NO:15 for the nucleotide sequence and SEQ ID NO:16 for the amino acid sequence); and FIG. 11c—a cassette encoding a BGL1 fused to Cel1 signal peptide as in FIG. 11b and in addition to HDEL (SEQ ID NO:17) ER-retaining peptide at the C-terminus for accumulation in the ER (see, SEQ ID NO:18 for the nucleotide sequence and SEQ ID NO:19 for the amino acid sequence).

FIG. 12 demonstrate PCR amplification results of bgl1 cDNA indicating the presence of bgl1 cDNA in transgenic plants. CB10 and CB11-transgenic plants transformed with bgl1 and Cel1 signal peptide without HDEL, SEQ ID NO:17 ER retaining peptide. CBT3, CBT8 and CBT15—different transgenic lines transformed with bgl1, Cel1 signal peptide and HDEL, SEQ ID NO:17. B1—a transgenic plants transformed with bgl1. 1 kb—1 kb DNA marker. WT—wild type non transgenic plant. pETB1—bgl1 plasmid DNA.

FIGS. 13a-b show Western blot analyses of transgenic plants containing BGL1 without signal peptide (13a), and BGL1 with Cel1 signal peptide (13b), with and without HDEL, SEQ ID NO:17 ER retaining peptide. An gluco— purified A. niger beta-glucosidase. WT—nontransgenic control plant. B1, B15, B16, B20, B27, B33 and B34—different transgenic lines transformed with bgl1. CBT1, CBT 3, CBT 7 and CBT 8—different transgenic lines transformed with bgl1, Cel1 signal peptide and HDEL, SEQ ID NO:17. CB10 and CB12—transgenic plants transformed with bgl1 and Cel1 signal peptide without HDEL, SEQ ID NO:17 ER retaining peptide.

DESCRIPTION OF THE PREFERRED EMBODIMENTS

Figure 1C:
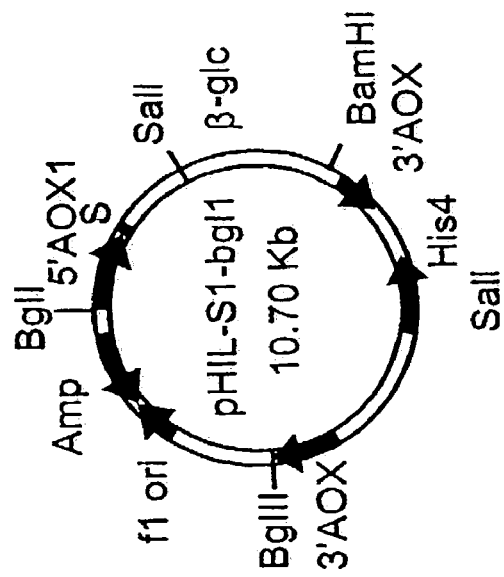
FIGS. 1a-c demonstrate plasmid maps employed as expression vectors for bgl1 cDNA.

The present invention is of a polypeptide having β-glucosidase enzymatic activity, a polynucleotide encoding the polypeptide, a nucleic acid constructs carrying the polynucleotide, transformed or infected cells, such as yeast cells, and organisms expressing the polynucleotide and various uses of the polypeptide, the polynucleotide, cells and/or organisms, including, but not limited to, producing a recombinant polypeptide having the β-glucosidase enzymatic activity, increasing the level of aroma compounds in alcoholic beverages, as well as other fermentation products of plant material, hydrolyzing cellobiose and thus increasing the level of fermentable glucose, increasing the production of alcohol, such as ethanol from plant material, increasing the aroma released from a plant or a plant product, and hydrolysis or transglycosylation of glycosides.

The principles and operation of the present invention may be better understood with reference to the drawings and accompanying descriptions.

Before explaining at least one embodiment of the invention in detail, it is to be understood that the invention is not limited in its application to the details of the components set forth in the following description or exemplified in the examples that follow. The invention is capable of other embodiments or of being practiced or carried out in various ways. Also, it is to be understood that the phraseology and terminology employed herein is for the purpose of description and should not be regarded as limiting.

According to one aspect of the present invention there is provided an isolated nucleic acid comprising a genomic, complementary or composite polynucleotide encoding a polypeptide having a β-glucosidase catalytic activity. Preferably the polynucleotide is derived from Aspergillus niger, however other sources are applicable. These include all isolated polynucleotides encoding polypeptide having β-glucosidase catalytic activity. Such polynucleotides and polypeptides identified by their GenBank Accession Nos. are listed in Table 1 below, all of which can be used while implementing the present invention.

TABLE 1

Accession numbers of cDNA and their encoded beta-glucosidases (EC.3.2.1.21)

| Organism | SWISS-PROT | EMBL |
|---|---|---|
| Acetobacter xylinus | O24749 | AB003689; AB010645 |
| Agrobacterium sp. | P12614 | M19033; AAA22085.1 |
| Agrobacterium tumefaciens | P27034 | M59852; AAA22082.1 |
| Arabidopsis thaliana | O82772, O24433, O23656 | AF082157; AF082158; AC009327; U72153; U72155 AC020665; AC066691 |
| Aspergillus aculeatus | P48825 | D64088, BAA10968.1 |
| Aspergillus kawachi | P87076 | AB003470 |
| Aspergillus niger B1 | | AJ132386; CAB75696.1 |
| Aspergillus niger AMS1 | Q9P456 | AF268911 |
| Avena sativa | Q38786, Q9ZP27 | X78433; AF082991 |
| Azospirillum irakense | | AF090429; AAF21798.1 |
| Bacillus circulans | Q03506 | M96979; AAA22266.1 |
| Bacillus sp. GL1 | Q9ZNN7 | AB009411; BAA36161.1; AB009410 |
| Bacillus polymyxa | P22073, P22505 | M60210; M60211 |
| Bacillus subtilis | P40740 | Z34526; CAA84287.1 |
| Bacillus subtilis | P42403 | D30762; BAA06429.1 |
| Bacteroides fragilis | O31356 | AF006658; AAB62870.1 |
| Bifidobacterium breve | P94248, O08487 | D84489; D88311 |
| Botryotinia fuckeliana | | AJ130890; CAB61489.1 |
| Brassica napus | Q42618 | X82577 |
| Brassica nigra | O24434 | U72154 |
| Butyrivibrio fibrisolvens | P16084 | M31120; AAA23008.1 |
| Caldocellum saccharolyticum | P10482 | X12575; CAA31087.1 |
| Caldicellulosiruptor sp. 14B | Q9ZEN0 | AJ131346 |
| Candida wickerhamii | Q12601 | U13672 |
| Cavia porcellus | P97265 | U50545 |
| Cellulomonas biazotea | O51843 | AF005277; AAC38196.1 |
| Cellulomonas fimi | Q46043 | M94865 |
| Cellvibrio gilvus | P96316 | D14068; BAA03152.1 |
| Chryseobacterium meningosepticum | O30713 | AF015915 |
| Clostridium stercorarium | O08331 | Z94045 |
| Clostridium thermocellum | P26208 | X60268; CAA42814.1 |
| Clostridium thermocellum | P14002 | X15644; CAA33665.1 |
| Coccidioides immitis | O14424 | U87805; AF022893 |
| Costus speciosus | Q42707 | D83177 |
| Dalbergia cochinchinensis | Q9SPK3 | AF163097 |
| Dictyostelium discoideum | Q23892 | L21014 |
| Digitalis lanata | Q9ZPB6 | AJ133406 |
| Erwinia chrysanthemi | Q46684 | U08606; AAA80156.1 |
| Erwinia herbicola | Q59437 | X79911; CAA56282.1 |
| Escherichia coli | P33363 | U15049; AAB38487.1 |
| Escherichia coli K12/MG1655 | E65074, Q46829 | U28375; AE000373 |
| Glycine max | | AF000378; AAD09291.1 |
| Hansenula anomala | P06835 | X02903; CAA26662.1 |
| Homo sapiens | | AJ278964; CAC08178.1 |
| Hordeum vulgare | Q40025 | L41869 |
| Humicola grisea var. thermoidea | O93784 | AB003109 |
| Kluyveromyces marxianus | P07337 | X05918; CAA29353.1 |
| Lactobacillus plantarum | O86291 | Y15954; AJ250202; CAB71149.1 |
| Manihot esculenta | Q40283 | X94986 |
| Microbispora bispora | P38645 | M97265; AAA25311.1 |
| Nicotiana tabacum | O82151 | AB017502; BAA33065.1 |
| Orpinomyces sp. PC-2 | | AF016864; AAD45834.1 |
| Oryza sativa | Q42975 | U28047 |
| Paenibacillus polymyxa | P22073 | M60210; AAA22263.1 |
| Paenibacillus polymyxa | P22505 | M60211; AAA22264.1 |
| Phaeosphaeria avenaria | | AJ276675; CAB82861.1 |
| Phanerochaete chrysosporium | O74203 | AF036872; AF036873 |
| Pichia anomala (Candida pelliculosa) | P06835 | X02903 |
| Pinus contorta | | AF072736; AAC696.1 |
| Polygonum tinctorium | | AB003089; BAA78708.1 |
| Prunus avium | Q43014 | U39228 |
| Prunus serotina | Q43073, Q40984 | U50201; U26025 |
| Prevotella albensis M384 | | AJ276021; CAC07184.1 |
| Prevotella ruminicola | Q59716 | U35425 |
| Pyrococcus furiosus | Q51723 | AF013169; U37557 |
| Ruminococcus albus | P15885 O66050 | X15415; CAA33461.1 U92808 |
| Saccharomycopsis fibuligera | P22506 | M22475; AAA34314.1 |
| Saccharomycopsis fibuligera | P22507 | M22476; AAA34315.1 |
| Saccharopolyspora erythraea | O70021 | Y14327 |
| Salmonella typhimurium | Q56078 | D86507; BAA13102.1 |
| Schizophyllum commune | P29091 | M27313; AAA33925.1 |
| Schizosaccharomyces pombe | | AL355920; CAB91163.1 |
| Secale cereale | | AF293849; AAG00614.1 |
| Septoria lycopersici | Q99324 | U24701; U35462 |
| Sorghum bicolor | Q41290 | U33817 |
| Spodoptera frugiperda | O61594 | AF052729 |
| Streptomyces coelicolor A3(2) | | AL121596; CAB56653.1 |
| Streptomyces reticuli | Q9X9R4 | AJ009797 |
| Streptomyces rochei A2 | Q55000 | X74291 |
| Streptomyces sp. QM-B814 | Q59976 | Z29625 |
| Thermoanaerobacter brockii | P96090, Q60026 | Z56279; Z56279 |
| Thermobifida fusca ER1 | | AF086819; AAF37727.1 |
| Thermococcus sp. | O08324 | Z70242 |
| Thermotoga maritima | Q08638 | X74163; CAA52276.1 |
| Thermotoga neapolitana | O33843, Q60038 | Z97212; Z77856; CAB10165.1 |
| Thermus sp. Z-1 | Q9RA58 | AB034947 |
| Thermus thermophilus | Q9X9D4 | Y16753 |
| Trichoderma reesei (Hypocrea Jecorina) | Q12715, O93785 | U09580; AAA18473.1, AB003110 |
| Trifolium repens | P26204 | X56734; CAA40058.1 |
| Trifolium repens | P26205 | X56733; CAA40057.1 |
| Tropaeolum majus | O82074 | AJ006501; CAA07070.1 |
| Zea mays | P49235, Q41761 | X74217, U25157; CAA52293.1 U33816, U44087, U44773 |
| Unidentified bacterium | Q60055 | U12011 |

As used herein in the specification and in the claims section that follows, the term "isolated" refers to a biological component (such as a nucleic acid or protein or organelle) that has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

As used herein and in the claims section that follows the terms and phrases "polynucleotide" and "polynucleotide sequence" are used interchangeably and refer to a nucleotide sequence which can be DNA or RNA of, for example, genomic or synthetic origin, which may be single- or double-stranded, and which may represent the sense or antisense strand. Similarly, the terms "polypeptide" and "polypeptide sequence" are interchangeably used herein and refer to an amino acid sequence of any length.

As used herein in the specification and in the claims section that follows, the phrase "complementary polynucleotide sequence" includes sequences, which originally result from reverse transcription of messenger RNA using a reverse transcriptase or any other RNA dependent DNA polymerase. Such sequences can be subsequently amplified in vivo or in vitro using a DNA dependent DNA polymerase.

As used herein in the specification and in the claims section that follows, the phrase "genomic polynucleotide sequence" includes sequences which originally derive from a chromosome and reflect a contiguous portion of a chromosome.

As used herein in the specification and in the claims section that follows, the phrase "composite polynucleotide sequence" includes sequences which are at least partially complementary and at least partially genomic. A composite sequence can include some exonal sequences required to encode the polypeptide having the β-glucosidase catalytic activity, as well as some intronic sequences interposing therebetween. The intronic sequences can be of any source, including of other genes, and typically will include conserved splicing signal sequences. Such intronic sequences may further include cis acting expression regulatory elements, as hereinbelow described.

As used herein in the specification and in the claims section that follows, the phrase "having a β-glucosidase catalytic activity" refers to a polypeptide sequence, protein or fragments thereof capable of serving as catalysts to a chemical reaction involving hydrolysis of the O-glycosidic bond of glucosides, the result of which is the release of a β-D-glucose residue(s), or an aglycon, in addition to the β-D-glucose residue. Specifically, hydrolysis by retaining enzymes is performed while maintaining the β-configuration of the anomeric center of the carbohydrate. A wide specificity for β-glucosides exists, thus, some examples also hydrolyze one or more of the following: β-D-galactosides, α-L-arabinosides, β-D-xylosides, and β-D-fucosides.

As used herein the term "catalyst" refers to a substance that accelerates a chemical reaction, but is not consumed or changed permanently thereby.

As used herein the term "glucoside" refers to a compound of at least two monomers, at least one of which is a glucose, including a glycoside bond. Examples of glucosides include, but are not limited to, glucose containing backbones, such as the diglucose cellobiose, and the glucose polymer, cellulose.

According to preferred embodiments, the polynucleotide according to this aspect of the present invention encodes a polypeptide as set forth in SEQ ID NO:2 or a portion thereof which retains β-glucosidase catalytic activity.

Alternatively or additionally, the polynucleotide according to this aspect of the present invention is as set forth in SEQ ID NO: 1, 3 or a portion thereof, the portion encodes a polypeptide retaining β-glucosidase catalytic activity.

In a broader aspect the polynucleotides according to the present invention encode a polypeptide which is at least 75%, at least 80%, at least 85%, at least 90%, at least 95% or more, say 95%-100% homologous to SEQ ID NO:2 as determined using the BestFit software of the Wisconsin sequence analysis package, utilizing the Smith and Waterman algorithm, where gap creation penalty equals 8 and gap extension penalty equals 2.

According to preferred embodiments, the polynucleotides according to the broader aspect of the present invention encodes a polypeptide as set forth in SEQ ID NOs:1 or 3 or a portion thereof which retains activity.

Alternatively or additionally, the polynucleotides according to this broader aspect of the present invention are hybridizable with SEQ ID NOs: 1 or 3.

Hybridization for long nucleic acids (e.g., above 200 bp in length) is effected according to preferred embodiments of the present invention by stringent or moderate hybridization, wherein stringent hybridization is effected by a hybridization solution containing 10% dextrane sulfate, 1 M NaCl, 1% SDS and 5×10$^6$ cpm $^{32}$P labeled probe, at 65° C., with a final wash solution of 0.2×SSC and 0.1% SDS and final wash at 65° C.; whereas moderate hybridization is effected by a hybridization solution containing 10% dextrane sulfate, 1 M NaCl, 1% SDS and 5×10$^6$ cpm $^{32}$P labeled probe, at 65° C., with a final wash solution of 1×SSC and 0.1% SDS and final wash at 50° C.

Yet alternatively or additionally, the polynucleotides according to this broad aspect of the present invention is preferably at least 70%, at least 75%, at least 80%, at least 85%, at least 90%, at least 95% or more, say 95%-100%, identical with SEQ ID NOs: 1 or 3 as determined using the BestFit software of the Wisconsin sequence analysis package, utilizing the Smith and Waterman algorithm, where gap weight equals 50, length weight equals 3, average match equals 10 and average mismatch equals −9.

Thus, this broad aspect of the present invention encompasses (i) polynucleotides as set forth in SEQ ID NOs:1 or 3; (ii) fragments thereof; (iii) sequences hybridizable therewith; (iv) sequences homologous thereto; (v) sequences encoding similar polypeptides with different codon usage; (vi) altered sequences characterized by mutations, such as deletion, insertion or substitution of one or more nucleotides, either naturally occurring or man induced, either randomly or in a targeted fashion.

According to another aspect of the present invention there is provided a nucleic acid construct comprising the isolated nucleic acid described herein.

According to a preferred embodiment, the nucleic acid construct according to this aspect of the present invention further comprising at least one cis acting control (regulatory) element for regulating the expression of the isolated nucleic acid. Such cis acting regulatory elements include, for example, promoters, which are known to be sequence elements required for transcription, as they serve to bind DNA dependent RNA polymerase, which transcribes sequences present downstream thereof. Further details relating to various regulatory elements are described hereinbelow.

While the isolated nucleic acid described herein is an essential element of the invention, it is modular and can be used in different contexts. The promoter of choice that is used in conjunction with this invention is of secondary importance, and will comprise any suitable promoter. It will be appreciated by one skilled in the art, however, that it is necessary to make sure that the transcription start site(s) will be located upstream of an open reading frame. In a preferred embodiment of the present invention, the promoter that is selected comprises an element that is active in the particular host cells of interest. These elements may be selected from transcriptional regulators that activate the transcription of genes essential for the survival of these cells in conditions of stress or starvation, including the heat shock proteins.

A construct according to the present invention preferably further includes an appropriate selectable marker. In a more preferred embodiment according to the present invention the construct further includes an origin of replication. In another most preferred embodiment according to the present invention the construct is a shuttle vector, which can propagate both in *E. coli* (wherein the construct comprises an appropriate selectable marker and origin of replication) and be compatible for propagation in cells, or integration in the genome, of an organism of choice, such as a plant. The construct according to this aspect of the present invention can be, for example, a plasmid, a bacmid, a phagemid, a cosmid, a phage, a virus or an artificial chromosome.

According to an additional aspect of the present invention there is provided a recombinant protein comprising a polypeptide having a glucosidase catalytic activity. The polypeptide is preferably derived from an *Aspergillus niger* and preferably includes a signal peptide and optionally an endoplasmic reticulum retaining peptide.

According to preferred embodiments, the polypeptide according to this aspect of the present invention is as set forth in SEQ ID NO:2 or a portion thereof which retains β-glucosidase catalytic activity.

SEQ ID NO:2 of *A. niger* β-glucosidase is similar to the amino acid sequence of the β-glucosidase of *A. kawachii*. However, while the former is highly stable at wide range of temperatures and pH treatments, the latter is relatively unstable, and thus has certain disadvantages, rendering its use for the purpose of the present invention as is further detailed and described hereinunder, unfeasible and/or much less attractive.

Recently, Iwashita and coworkers have published the sequence of a β-glucosidase (GenBank/EMBL AB003470) obtained from *Aspergillus kawachii* strain: IFO4308. Sequence comparison between *Aspergillus kawachii* β-glucosidase and *A. niger* β-glucosidase revealed that the two share 98% homology.

Enzymes of the two *Aspergillus* sp. contain seven cysteine residues and identical number of glycosylation sites, while differing in their degree of glycosylation (35).

The physical and kinetic properties of three β-glucosidases from *Aspergillus kawachii* were described (35), and the three were shown to be products of the same gene, differing solely by the degree of glycosylation. The three purified *A. kawachii* β-glucosidases were readily inactivated, even at moderate pH and temperature conditions. In sharp distinction, while examining the stability of the recombinant *A. niger* β-glucosidase according to the present invention under conditions identical to those described by Iwashita et al. and as described hereinbelow in the Examples section, revealed that the enzyme is highly stable, retaining majority of the enzymatic activity even after 1 hour incubation at 60° C. (68% activity, as defined by percent activity of an enzyme kept at 4° C.).

Thus, despite the similarity between the *A. kawachii* and *A. niger* β-glucosidases, the *A. niger* enzyme unexpectedly exhibits significantly higher thermal and pH stability.

According to yet another aspect of the present invention there is provided a host cell comprising a nucleic acid construct as described herein. The term "host cell" refers to a recipient of a heterologous nucleic acid, which host cell can be either a prokaryotic cell, such as *E. coli*, or a eukaryotic cell, such as a yeast cell, a filamentous fungus cell, a plant cell or an animal cell. Examples for a yeast cell include, but not limited to, *Pichia* sp. such as *P. pastoris*, and *Saccharomyces* sp. such as *S. cervisiae*.

As used herein and in the claims section which follows, the term "heterologous" when used in context of a nucleic acid sequence or a protein found within a plant, plant derived tissue or plant cells, or alternatively, within a eukaryotic cell, such as yeast, or a prokaryotic cell such as bacteria, refers to nucleic acid or amino acid sequences typically not native to the plant, plant derived tissue or plant cells, or alternatively, to the eukaryotic cell, such as yeast, or the prokaryotic cell, such as bacteria. Interchangeably, nucleic acid or amino acid sequences typically not native to the plant, plant derived tissue or plant cells, or alternatively, to the eukaryotic cell, such as yeast, or the prokaryotic cell, such as bacteria, are referred to by "recombinant nucleic acid" and "recombinant protein", respectively. Thus, a recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

As used herein in the specification and in the claims section that follows, the term "eukaryotic cell" refers to a cell containing a diploid genome through at least a portion of its life cycle, having membrane-bound nucleus with chromosomes made of DNA, with cell division involving a form of mitosis in which spindles are involved. Possession of a eukaryote type of cell characterizes the four kingdoms, Protoctista, Fungi, Plantae and Animalia.

As used herein in the specification and in the claims section that follows, the term "prokaryotic cell" refers to various bacteria and blue-green algae, characterized by the absence of the nuclear organization, mitotic capacities and complex organelles that typify the eukaryote superkingdom. Examples of prokaryotic cell according to the present invention are bacteria, such as, but not limited to, *E. coli*.

According to still another aspect of the present invention there is provided an organism comprising a nucleic acid construct as described herein, such as, but not limited to, a plant. Such an organism is said to be transformed or virally infected.

As used herein the term "transformed" and its conjugations such as transformation, transforming and transform, all relate to the process of introducing heterologous nucleic acid sequences into a cell or an organism, which nucleic acid sequences are propagatable to the offspring. The term thus reads on, for example, "genetically modified", "transgenic" and "transfected", which may be used herein to further describe and/or claim the present invention. The term relates both to introduction of a heterologous nucleic acid sequence into the genome of an organism and/or into the genome of a nucleic acid containing organelle thereof, such as into a genome of chloroplast or a mitochondrion.

As used herein the phrase "viral infected" includes infection by a virus carrying a heterologous nucleic acid sequence. Such infection typically results in transient expression of the nucleic acid sequence, which nucleic acid sequence is typically not integrated into a genome and therefore not propagatable to offspring, unless further infection of such offspring is experienced.

There are various methods of introducing foreign genes into both monocotyledonous and dicotyledenous plants (Potrykus, I., Annu. Rev. Plant. Physiol., Plant. Mol. Biol. (1991) 42:205-225; Shimamoto et al., Nature (1989) 338: 274-276). The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure, which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledenous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation, which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the protein. The new generation plants, which are produced, are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Sequences suitable for permitting integration of the heterologous sequence into the plant genome are recommended. These might include transposon sequences and the like for homologous recombination as well as Ti sequences which permit random insertion of a heterologous expression cassette into a plant genome.

Suitable prokaryote selectable markers include resistance toward antibiotics such as ampicillin or tetracycline. Other DNA sequences encoding additional functions may also be present in the vector, as is known in the art.

The constructs of the subject invention will include an expression cassette for expression of the protein of interest. Usually, there will be only one expression cassette, although two or more are feasible. The recombinant expression cassette will contain in addition to the heterologous sequence one or more of the following sequence elements, a promoter region, plant 5' untranslated sequences which can include regulatory elements, initiation codon depending upon whether or not the structural gene comes equipped with one, and a transcription and translation termination sequence. Unique restriction enzyme sites at the 5' and 3' ends of the cassette allow for easy insertion into a pre-existing vector.

As used herein, the phrase "regulatory element" refers to a nucleotide sequence which are typically included within an expression cassette and function in regulating (i.e., enhancing or depressing) the expression of a coding sequence therefrom. This regulation can be effected either at the transcription or the translation stages. Examples of regulatory elements include, but are not limited to, enhancers, suppressers and transcription terminators.

As used herein the term "promoter" refers to a nucleotide sequence, which can direct gene expression in cells. Such a promoter can be derived from a plant, a plant virus, or from any other living organism including bacteria and animals.

A plant promoter can be a constitutive promoter, such as, but not limited to, CaMV35S and CaMV19S promoters, FMV34S promoter, sugarcane bacilliform badnavirus promoter, CsVMV promoter, *Arabidopsis* ACT2/ACT8 actin promoter, *Arabidopsis* ubiquitin UBQ1 promoter, barley leaf thionin BTH6 promoter, and rice actin promoter.

The promoter can alternatively be a tissue specific promoter. Examples of plant tissue specific promoters include, without being limited to, bean phaseolin storage protein promoter, DLEC promoter, PHSβ promoter, zein stprotein promoter, conglutin gamma promoter from soybean, AT2S1 gene promoter, ACT11 actin promoter from *Arabidopsis*, napA promoter from *Brassica napus*, potato patatin gene promoter and the Tob promoter.

The promoter may also be a promoter which is active in a specific developmental stage of a plant's life cycle, for example, a promoter active in late embryogenesis, such as: the LEA promoter; Endosperm-specific expression promoter (the seed storage prolamin from rice is expressed in tobacco seed at the developmental stage about 20 days after flowering) or the promoter controlling the FbL2A gene during fiber wall synthesis stages.

In case of a tissue-specific promoter, it ensures that the heterologous protein is expressed only in the desired tissue, for example, only in the flower, the fruit, the root, the seed, etc.

Both the tissue-specific and the non-specific promoters may be constitutive, i.e., may cause continuous expression of the heterologous protein.

The promoter may also be an inducible promoter, i.e., a promoter which is activated by the presence of an inducing agent, and only upon said activation, causes expression of the heterologous protein. An inducing agent can be for example, light, chemicals, drought, high salinity, osmotic shock, oxidant conditions or in case of pathogenicity and include, without being limited to, the light-inducible promoter derived from the pea rbcS gene, the promoter from the alfalfa rbcS gene, the promoters DRE, MYC and MYB active in drought; the promoters INT, INPS, prxEa, Ha hsp17.7G4 and RD21 active in high salinity and osmotic stress, the promoters hsr303J and str246C active in pathogenic stress, the copper-controllable gene expression system and the steroid-inducible gene system Alternatively, an inducing agent may be an endogenous agent which is normally present in only certain tissues of the plant, or is produced only at certain time periods of the plant's life cycle, such as ethylene or steroids. By using such an endogenous tissue-specific inducing agent, it is possible to control the expression from such inducible promoters only in those specific tissues. By using an inducing agent produced only during a specific period of the life cycle, it is possible to control the expression from an inducible promoter to the specific phase in the life-cycle in which the inducing agent is produced.

Bacterial and yeast derived promoters are well known in the art.

Viruses are a unique class of infectious agents whose distinctive features are their simple organization and their mechanism of replication. In fact, a complete viral particle, or virion, may be regarded mainly as a block of genetic material (either DNA or RNA) capable of autonomous replication, surrounded by a protein coat and sometimes by an additional membranous envelope such as in the case of alpha viruses. The coat protects the virus from the environment and serves as a vehicle for transmission from one host cell to another.

Viruses that have been shown to be useful for the transformation of plant hosts include CaV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral foreign genes in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, the constructions can be made to the virus itself. Alternatively, the virus can first be cloned into a bacterial plasmid for ease of constructing the desired viral vector with the foreign DNA. The virus n then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression of non-viral foreign genes in plants is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) in the host to produce the desired protein.

In many instances it is desired to target the expression of a recombinant protein. Such targeting can be into a cellular organelle or outside of the cell. This can be effected, as is well known in the art, by appropriate signal peptides, which are fused to the polypeptide to be targeted, typically at the N terminus.

Thus, as used herein and in the claims section which follows, the phrase "signal peptide" refers to a stretch of amino acids which is effective in targeting a protein expressed in a cell into a target location. Different signal peptides, which are known in the art, are effective in secreting a protein from bacteria, yeast, plant and animal cells.

It should be noted in this respect that signal peptides serve the function of translocation of produced protein across the endoplasmic reticulum membrane. Similarly, transmembrane segments halt translocation and provide anchoring of the protein to the plasma membrane, see, Johnson et al. The Plant Cell (1990) 2:525-532; Sauer et al EMBO J. (1990) 9:3045-3050; Mueckler et al. Science (1985) 229:941-945. Mitochondrial, nuclear, chloroplast, or vacuolar signals target expressed protein correctly into the corresponding organelle through the secretory pathway, see, Von Heijne, Eur. J. Biochem. (1983) 133:17-21; Yon Heijne, J. Mol. Biol. (1986) 189:239-242; Iturriaga et al. The Plant Cell (1989) 1:381-390; McKnight et al., Nucl. Acid Res. (1990) 18:4939-4943; Matsuoka and Nakamura, Proc. Natl. Acad. Sci. USA (1991) 88:834-838. A recent book by Cunningham and Porter (Recombinant proteins from plants, Eds. C. Cunningham and A. J. R. Porter, 1998 Humana Press Totowa, N.J.) describe methods for the production of recombinant proteins in plants and methods for targeting the proteins to different compartments in the plant cell. In particular, two chapters therein (14 and 15) describe different methods to introduce targeting sequences that results in accumulation of recombinant proteins in compartments such as ER, vacuole, plastid, nucleus and cytoplasm. The book by Cunningham and Porter is incorporated herein by reference. Presently, the preferred site of accumulation of the fusion protein according to the present invention is the ER using signal peptide such as Cel 1 or the rice amylase signal peptide at the N-terminus and an ER retaining peptide (HDEL, SEQ ID NO:17; or KDEL, SEQ ID NO:24) at the C-terminus.

According to an additional aspect of the present invention there is provided a method of producing recombinant β-glucosidase. The method according to this aspect of the present invention is effected by introducing, in an expressible or overexpressible form, a nucleic acid construct into a host cell. The nucleic acid construct includes a genomic, complementary or composite polynucleotide preferably derived from *Aspergillus niger* and encoding a polypeptide having a β-glucosidase catalytic activity. The polynucleotide preferably further encodes a signal peptide in frame with the polypeptide. Still preferably, the polynucleotide further encodes an endoplasmic reticulum retaining peptide in frame with the polypeptide.

As used herein the term "introducing" refers both to transforming and to virally infecting, as these terms are further defined hereinabove. As used herein the terms "expressible form" and "overexpressible form" refers to a recombinant form which includes the required regulatory elements to effect expression or over expression of a coding region, all as is further detailed hereinabove.

According to a preferred embodiment of this aspect of the present invention, after sufficient expression has been detected, the polypeptide having the β-glucosidase catalytic activity is extracted from the expressing host cell.

Thus host cells, expressing the polypeptide according to the present invention, provide an immediate, easy and indefinite source of the polypeptide.

Any number of well-known liquid or solid culture media may be used for appropriately culturing host cells of the present invention, although growth on liquid media is preferred as the secretion of the polypeptide into the media results in simplification of polypeptide recovery. As is further detailed hereinabove, such secretion can be effected by the incorporation of a suitable signal peptide. The β-glucosidase may be isolated or separated or purified from host cell preparations using techniques well known in the art, such as, but not limited to, centrifugation filtration, chromatography, electrophoresis and dialysis. Further concentration and/or purification of the β-glucosidase may be effected by use of conventional techniques, including, but not limited to, ultrafiltration, further dialysis, ion-exchange chromatography, HPLC, size-exclusion chromatography, cellobiose-sepharose affinity chromatography, and electrophoresis, such as polyacrylamide-gel-electrophoresis (PAGE). Using these techniques, β-glucosidase may be recovered in pure or substantially pure form.

According to an additional aspect of the present invention there is provided a method of increasing a level of at least one fermentation substance in a fermentation product. The method according to this aspect of the present invention is effected by fermenting a glucose containing fermentation starting material by a yeast cell overexpressing a nucleic acid construct which includes a genomic, complementary or composite polynucleotide preferably derived from *Aspergillus niger* and which encodes a polypeptide having a glucosidase catalytic activity, thereby increasing the level of the at least one fermentation substance in the fermentation product. The polynucleotide preferably further encodes a signal peptide in frame with the polypeptide. Still preferably, the polynucleotide further encodes an endoplasmic reticulum retaining peptide in frame with the polypeptide.

According an alternative aspect of the present invention there is provided a method of increasing a level of at least one fermentation substance in a fermentation product. The method according to this aspect of the present invention is effected by fermenting a plant derived glucose containing fermentation starting material by a yeast cell, the plant overexpressing a nucleic acid construct which includes a genomic, complementary or composite polynucleotide preferably derived from *Aspergillus niger* and which encodes a polypeptide having a β-glucosidase catalytic activity, thereby increasing the level of the at least one fermentation substance in the fermentation product. The polynucleotide preferably further encodes a signal peptide in frame with the polypeptide. Still preferably, the polynucleotide further encodes an endoplasmic reticulum retaining peptide in frame with the polypeptide.

As used herein in the specification and in the claims section that follows, the term "fermentation" refers to a chemical change induced in a complex organic compound by the action of an enzyme, whereby the substance is split into simpler compounds. Specifically, the term "fermentation" includes the anaerobic dissimilation of substrates with the production of energy and reduced compounds, the final products thereof are organic acids, alcohols, such as ethanol, isopropanol, butanol, etc., and $CO_2$. Such products, are typically secreted and each of which is referred to herein as a "fermentation substance", i.e., any known fermentation resultant of either microbial or yeast fermentation.

As used herein in the specification and in the claims section that follows, the phrase "fermentation product" refers to the resultant material of a fermentation process. Examples include, but are not limited to, alcohol containing fermentation medium and alcoholic beverages, such a, but not limited to, fruit-based alcohol-containing beverages, wines and beers.

When used in conjunction with, for example, a β-glucanase, the β-glucosidase is effective for hydrolyzing a variety of cellulose containing materials to glucose. The glucose produced by enzymatic hydrolysis of the cellulose and other glucose containing saccharides, may be recovered and stored, or it may be subsequently fermented to ethanol using conventional techniques. Many processes for the fermentation of glucose generated from cellulose are well known, and are suitable for use herein. Briefly, the hydrolyzate containing the glucose from the enzymatic reaction is contacted with an appropriate microorganism under conditions effective for the fermentation of the glucose to ethanol. This fermentation may be separate from and follow the enzymatic hydrolysis of the cellulose (sequentially processed), or the hydrolysis and fermentation may be concurrent and conducted in the same vessel (simultaneously processed). Details of the various fermentation techniques, conditions, and suitable microorganisms have been described, for example, by Wyman (1994, Bioresource Technol., 50:3-16) or Olsson and Hahn-Hagerdal (1996, Enzyme Microbial Technol., 18:312-331), the content of each of which is incorporated herein by reference. Following the completion of a fermentation, the alcohol may be recovered by extraction, and optionally purified e.g., by distillation.

Thus, according to still another aspect of the present invention there is provided a method of producing an alcohol. The method according to this aspect of the present invention is effected by fermenting a glucose containing fermentation starting material by a cell overexpressing a nucleic acid construct including a genomic, complementary or composite polynucleotide preferably derived from *Aspergillus niger*, encoding a polypeptide having a β-glucosidase catalytic activity, and extracting the alcohol therefrom. The polynucleotide preferably further encodes a signal peptide in frame with the polypeptide. Still preferably, the polynucleotide further encodes an endoplasmic reticulum retaining peptide in frame with the polypeptide.

According to an additional aspect of the present invention there is provided a method of producing an alcohol. The method according to this aspect of the present invention is effected by fermenting a plant derived glucose containing fermentation starting material by a cell, the plant overexpressing a nucleic acid construct including a genomic, complementary or composite polynucleotide preferably derived from *Aspergillus niger*, encoding a polypeptide having a β-glucosidase catalytic activity, and extracting the alcohol therefrom. The polynucleotide preferably further encodes a signal peptide in frame with the polypeptide. Still preferably, the polynucleotide further encodes an endoplasmic reticulum retaining peptide in frame with the polypeptide.

Plants contain aroma and flavor compounds of glycosidic nature, their inherent aroma property can be released by degrading enzymes, turning a non-volatile aroma compound into its volatile form. Thus, for example, α-L-arabinofuranosidases, assist in the liberation of aroma compounds from substrates such as juices or wines, as described by Gunata et al. (European Patent Application No. 332.281, 1989; and "purification and some properties of an alpha-L-arabinofuranosidase from *A. niger* action on grape monoterpenyl arabinofuranosylglucosides. J. Agric. Food Chem. 38: 772-776, 1990). This outcome is achieved, for example, in a two step process wherein the first step comprises the use of an α-L-arabinofuranosidase, to catalyze the release of arabinose residues from monoterpenyl α-L-arabinofuranosylglucosides contained in, for example, the fruit or vegetable juice via the cleavage of the (1→6) linkage between a terminal arabinofuranosyl unit and the intermediate glucose of a monoterpenyl α-L-arabinofuranosylglucoside. The α-L-arabinofuranosidase is preferably in a purified form so as to avoid the undesirable degradation of other components of the juice which may be detrimental to its ultimate quality. In the second step, β-glucosidase is required to yield the free terpenol from the resulting desarabinosylated monoterpenyl glucoside. If desired, both reaction steps may be performed in the same reaction vessel without the need to isolate the intermediate product (Gunata et al. (1989), supra). Thus, β-glucosidase is an essential contributor when the liberation of these aroma compounds for improving the flavor of the juice or wine is desired. Moreover, in the case of wine, the control of the liberation of aroma compounds provides wines with a more consistent flavor, thus reducing or eliminating the undesirable effect of "poor vintage years" Additional information is contained in: "Cloning and expression of DNA molecules encoding arabinan degrading enzyme of fungal origin", U.S. Pat. No. 5,863,783; Y. Gueguen, et al. "A Very Efficient β-Glucosidase Catalyst for the Hydrolysis of Flavor Precursors of Wines and Fruit Juices", J. Agric. Food Chem. 44:2336-2340, 1996, each of which is incorporated herein by reference.

Thus, according to a further aspect of the present invention there is provided a method of increasing a level of at least one aroma substance in a plant derived product, such as, but not limited to, an alcoholic beverage. The method according to this aspect of the present invention is effected by incubating a glucose containing plant starting material with a yeast cell overexpressing a nucleic acid construct including a genomic, complementary or composite polynucleotide preferably derived from *Aspergillus niger* which encodes a polypeptide having a β-glucosidase catalytic activity, thereby increasing the level of the at least one aroma substance in the plant derived product. The polynucleotide preferably further encodes a signal peptide in frame with the polypeptide. Still preferably, the polynucleotide further encodes an endoplasmic reticulum retaining peptide in frame with the polypeptide.

While reducing the present invention to practice it was discovered that in order to obtain activity of a β-glucosidase in a transgenic plant, the expression construct should include a signal peptide. In addition, it was found that retaining the enzyme in the endoplasmic reticulum results in higher release of aroma compounds following homogenization and incubation. It is assumed that compartmentalization of the enzyme in for example the ER prevents it from interacting with its substrates which are mainly outside the cells, limiting such interaction following homogenization. Indeed, directing the enzyme to the apoplast resulted in increased release of aroma in vivo. Thus, depending on the specific application, one can chose weather to include in the construct an endoplasmic reticulum retaining peptide or not.

According to yet a further aspect of the present invention there is provided a method of increasing a level of at least one aroma substance in a plant derived product, such as, but not limited to, an alcoholic beverage. The method according to this aspect of the present invention is effected by incubating a glucose containing plant starting material with a yeast cell, said plant overexpressing a nucleic acid construct including a genomic, complementary or composite polynucleotide preferably derived from *Aspergillus niger* which encodes a polypeptide having a β-glucosidase catalytic activity, thereby increasing the level of the at least one aroma substance in the plant derived product. The polynucleotide preferably further encodes a signal peptide in frame with the polypeptide. Still preferably, the polynucleotide further encodes an endoplasmic reticulum retaining peptide in frame with the polypeptide.

As used herein in the specification and in the claims section that follows, the phrase "glucose containing starting material" refers to any source of energy, in the form of glucose containing compounds, other than free glucose, including, but not limited to, crushed, minced, diced or extracted plant material, plant, or portions thereof, such as fruits, examples thereof are tropical fruits and grapes.

According to an additional aspect of the present invention there is provided a method of producing an aroma spreading plant. As used herein in the specification and in the claims section that follows, the phrase "aroma spreading plant" refers to substantially any part of a plant, in which volatile compounds are generated by the catalytic activity of the β-glucosidase polypeptide of the present invention, release of volatile compounds therefrom is perceived by the olfactory system of an organism, such as a human.

The method according to this aspect of the present invention is effected by overexpressing in the plant a nucleic acid construct including a genomic, complementary or composite polynucleotide derived from *Aspergillus niger*, which encodes a polypeptide having a β-glucosidase catalytic activity, thereby increasing aroma spread from the plant. Such overexpression is preferably performed in a tissue specific manner by, for example, employing a tissue specific promoter, as hereinabove described, to thereby overexpress a heterologous protein in a selected portion of the plant. The tissue in which such overexpression is effected is selected according to the availability of glucose containing non-volatile aroma substrates therein. Thus, such an overexpression will cause the release of a volatile and aroma constituent of the substrate. Thus, according to preferred embodiments overexpressing the nucleic acid construct is limited to at least one tissue, such as a flower, a fruit, a seed, a root, a stem, pollen and leaves.

According to still a further aspect of the present invention there is provided a method of increasing a level of free glucose in a glucose containing fermentation starting material. The method according to this aspect of the present invention is effected by fermenting the glucose containing fermentation starting material by a cell overexpressing a nucleic acid construct including a genomic, complementary or composite polynucleotide preferably derived from *Aspergillus niger*, which encodes a polypeptide having a β-glucosidase catalytic activity, thereby increasing the level of the free glucose in the glucose containing fermentation starting material. The polynucleotide preferably further encodes a signal peptide in frame with the polypeptide. Still preferably, the polynucleotide further encodes an endoplasmic reticulum retaining peptide in frame with the polypeptide.

According to another aspect of the present invention there is provided a method of increasing a level of free glucose in a plant derived glucose containing fermentation starting material. The method according to this aspect of the present invention is effected by fermenting the plant derived glucose containing fermentation starting material by a cell, the plant overexpressing a nucleic acid construct including a genomic, complementary or composite polynucleotide preferably derived from *Aspergillus niger*, which encodes a polypeptide having a β-glucosidase catalytic activity, thereby increasing the level of the free glucose in the plant. The polynucleotide preferably further encodes a signal peptide in frame with the polypeptide. Still preferably, the polynucleotide further encodes an endoplasmic reticulum retaining peptide in frame with the polypeptide.

As used herein in the specification and in the claims section that follows, the term "free glucose" refers to glucose residues in the form of a monosaccharide, the levels of which are increased by the catalytic activity of β-glucosidase.

As used herein in the specification and in the claims section that follows, the phrase "glucose containing fermentation starting material" refers to any source of energy, in the form of glucose containing compounds, other than free glucose, including, but not limited to, crushed, minced, diced or extracted plant material, plant, or portions thereof, used in industrial fermentation processes.

According to yet another aspect of the present invention there is provided a method of increasing a level of extra- or intracellular free glucose in a plant. The method according to this aspect of the present invention is effected by overexpressing in the plant a nucleic acid construct including a genomic, complementary or composite polynucleotide preferably derived from *Aspergillus niger*, which encodes a polypeptide having a β-glucosidase catalytic activity, thereby increasing the level of the free glucose in the plant Thus, sweeter fruits can be produced. The polynucleotide preferably further encodes a signal peptide in frame with the polypeptide. Still preferably, the polynucleotide further encodes an endoplasmic reticulum retaining peptide in frame with the polypeptide.

Glycosidases, including β-glucosidase, catalyze reactions involving the hydrolysis of O-glycosidic bond of glycosides, and synthesize oligosaccharides when the reaction is run in reverse from the normal direction, a result achieved by, for example, site directed mutagenesis, and Km reversal. As described in the Background section hereinabove, the hydrolysis reaction mechanism of glycosidases involves two catalytic steps, the second of which involves a base catalyzed $H_2O$ attack, resulting in the regeneration of the enzyme, and the release of the saccharide residue. Thus, in addition, oligosaccharide synthesis can be achieved by adding a second saccharide to the reaction mixture, which competes with the $H_2O$ molecule, and reacts in its place with the first saccharide in, what is known as, a transglycosylation reaction. Hence, as glycosidases are generally available and easy to handle, these enzymes have the potential to catalyze the production of many different products using inexpensive substrates. For further detail see U.S. Pat. No. 5,716,812, which is incorporated herein by reference.

Thus, according to yet an additional aspect of the present invention there is provided a method of synthesizing oligosaccharides. The method according to this aspect of the present invention is effected by mixing a polypeptide having a β-glucosidase catalytic activity with first and second saccharide molecules to thereby join the first and second saccharide molecules into an oligosaccharide.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al. "Recombinant DNA", Scientific American Books, New York; Birren et al. (eds) "Genome Analysis: A Laboratory Manual Series", Vols. 14, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific liter, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Application", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

MATERIALS AND EXPERIMENTAL METHODS

Purification of *A. niger* β-Glucosidase:

A crude preparation of *A. niger* B1 (CMI CC 324626) β-glucosidase was obtained from Shaligal Ltd. (Tel-Aviv, Israel). A sample (10 ml) of the crude enzyme (140 Units/ml) was first diafiltered through a 50 kDa cut-off AMICON™ size filtration membrane (Amicon Corp., Danvers, Mass.), with 20 mM citrate buffer pH=5. The proteins were then separated on an FPLC equipped with a MONO-Q™ anion exchange RH 5/5 column (Amersham Pharmacia Biotech AB, Uppsala, Sweden), equilibrated with the same buffer. The enzyme was eluted with a linear gradient of 0 to 350 mM NaCl. Active fractions (see below, enzyme assays) were monitored and pooled (between 80-110 mM NaCl). The partially purified enzyme was dialyzed against 20 mM citrate buffer pH=3.5, applied to a RESOURCE-S™ (Amersham Biosciences Inc. Piscatawy, N.J.) cation exchange column equilibrated with the same buffer, and eluted with a gradient of 0-1 M NaCl. The purified enzyme (eluted at 155 mM NaCl) was concentrated by ultrafiltration (50 kDa cut-off membrane, Amicon).

Enzyme Assays:

β-glucosidase enzyme activity was monitored using a plate assay as follows. 4-methylumbelife β-D-glucopyranoside (MUGlc, Sigma Chemical Inc. St. Louis, Mo.) to a final concentration of 0.5 mM, was dissolved in PC buffer (50 mM phosphate, 12 mM citric acid, pH=3.4) at 45° C. The solution was mixed with 3% agar in water, previously boiled and then cooled to 45° C. The resulting solution (20 ml) was poured into a petri dish and after solidification, 10 µl enzyme samples were spotted. The plate was incubated at 50° C. for one hour, and then illuminated with long UV. An intense fluorescence was indicative of β-glucosidase activity.

Detection of β-glucosidase in polyacrylamide gels was carried out by washing the SDS-polyacrylamide gel with 1:1 isopropanol:PC buffer to remove SDS and renature the enzyme. The gel was washed once in PC buffer and incubated in a thin layer of a solution of 0.5 mM MUGlc. After incubation at 50° C. for one hour, the active protein band was visualized by UV light.

Quantitative assays were performed using pNPGlc as a substrate according to Shoseyov (7).

Determination of Thermal Stability of *A. niger* β-Glucosidase:

Recombinant enzyme (40 µg/ml) was dissolved in 20 mM citrate phosphate buffer, pH=5. Each tested sample (8 µl) was covered by 15 µl mineral oil. The activity was determined by the standard pNPGlc assay (7).

Deglycosylation of *A. niger* β-Glucosidase by N-Glycosidase-F:

A N-glycosidase-F (Boehringer Mannheim, Mannheim, Germany) reaction mixture, containing 0.125 µg pure β-glucosidase (previously denatured by boiling for 3 minutes in 1% SDS and 5% β-mercaptoethanol), 0.2 units of the N-glycosidase-F, sodium phosphate buffer (50 mM, pH=7.5), EDTA (25 mM), 1% Triton X-100 and 0.02% sodium azide, in a total volume of 12.5 µl, was incubated for 4 hours at 37° C. Reaction was stopped by addition of PAGE sample application buffer followed by 3 minutes of boiling.

Proteolysis and N-Terminal Sequences of *A. niger* B1 β-Glucosidase:

Partial enzymatic proteolysis with *Staphylococcus aureus* V8 protease was carried out as described by Cleveland (28). Briefly, FPLC-purified β-glucosidase (5 µg), was concentrated by acetone precipitation. The protein was separated on a preparative 10% SDS-PAGE. The gel was stained with coomassie blue, destained and rinsed with cold water, and the β-glucosidase protein band was excised. The resulting gel slice was applied to a second SDS-PAGE gel (15% acrylamide) and overlaid with *Staphylococcus* aurous V8 protease. Digestion was carried out within the stacking gel by turning off the current for 30 min. As the bromophenol blue dye neared the bottom of the stacking gel, the current was restored. The electrophoresed cleavage products were electroblotted to PVDF membranes. The native protein was transferred to PVDF in parallel. The N-terminal sequence of the native protein and two of the numerous cleavage products were analyzed by Edman degradation using a gas-phase protein sequencer (Applied Biosystems model 475A microsequencer).

Cloning of bgl1 cDNA and Genomic Gene:

Total RNA isolation: Total RNA was isolated from *Aspergillus niger* B1 as follows: *A. niger* B1 was grown in liquid culture consisting of mineral media $(NH_4)_2SO_4.3H_2O$ (0.5 g/l), $KH_2PO_4$ (0.2 g/l), $MgSO_4$ (0.2 g/l), $CaCl_2.H_2O$ (0.1 g/l), $FeSO_4.6H_2O$ (0.001 g/l), $ZnSO_4.7H_2O$ (0.001 g/l), and 2 mM citric acid, at pH=3.5 with 1% w/v bran as a carbon source. The medium was autoclaved, cooled and inoculated with *A. niger* B1 ($10^6$ spores/ml). Baffled flasks were used with constant shaking (200 RPM) at 37° C. The appearance of β-glucosidase activity was monitored by placing 5 µl of growth medium on 1% agar plates containing 0.5 mM MUGlc, as described above. Activity was detected following 15 hours incubation. The mycelium was harvested following 24 hours growth period, and the medium removed by filtering through GFA™ glass microfibre (Whatman Inter. Ltd., Maidstone, England). The mycelium was then frozen with liquid nitrogen and ground to fine powder with mortar and pestle. Total RNA was produced from this powder by the Guanidine thiocyanate (TRIREAGENT™) method (Molecular Research Center, Inc.).

RNA reverse-transcription reaction: cDNA was obtained by reverse transcribing total RNA (10 µg) using Stratagene RT-PCR kit (Stratagene, La Jolla, Calif.). The reaction mixture (50 µl) additionally consisted of: Oligo dT18 (1 µl), RNase Block Ribonuclease Inhibitor (20 units), 1× buffer (50 mM Tris-HCl, pH=8.3, 75 mM KCl, 10 mM DTT, 3 mM $MgCl_2$), dNTPs (500 µM each) and reverse transcriptase (300 units). Total RNA was initially denatured at 70° C., allowed to cool to room temperature (for primers annealing), and added to the reaction mixture. The reaction mixture was incubated for 1 hour at 37° C., followed by heating (95° C., 5 minutes) and stored at −70° C. until further use.

DNA amplification: Degenerate primers for DNA amplification reaction by PCR methods were synthesized, based on part of the amino acid N-terminal sequence and an internal sequence, as determined by the Edman degradation, following V8 proteolysis (hereinbelow, experimental results). The partial sequence from β-glucosidase N-terminal derived amino acid sequence was Ser-Pro-Pro-Tyr-Tyr-Pro (SEQ ID NO:4), yielding the following primer: 5'-(C/G)(A/C/G/T)CC(A/C/G/T) CC(A/C/G/T)TA(C/T)TA(C/T)CC-3' (SEQ ID NO:5). The partial sequence from E2 internal cleavage product amino acid sequence was Gln-Pro-Ile-Leu-Pro-Ata-Gly-Gly (SEQ ID NO:6), yielding the following primer: 5'-TCCIGC(T/G/C/A)GG(TG/C/A)A(G/A) (T/G/A)AT(T/G/C/A)GG(TIC)TG-3' (SEQ ID NO: 7).

DNA amplification reaction mixture (25 µl) contained: reverse transcriptase reaction product (1 µl), 10×PCR buffer (2.5 µl, Promega Corp., Madison, Wis.), dNTPs (250 µM each), $MgCl_2$ (2.0 mM), degenerate primers (250 pmol each), DNA polymerase (3 units, Stratagene, La Jolla, Calif.) and overlaid with mineral oil (25 µl). The reaction was performed in an automated heating block (Programmable thermal controller—MJ Research, Inc.). PCR cycling conditions were 30 seconds denaturing at 94° C., 60 seconds annealing at 50° C., and 150 seconds elongation at 72° C., repeated 36 times. The resulting amplified product was electrophoresed on a 1.2% (w/v) agarose/TBE gel, resulting in a 2.2 kb cDNA gene fragment, which was further isolated using Gel Extraction Kit (QIAGEN, Hilden, Germany) and cloned directly into the single 3'-T PCR insertion site of pGEM-T cloning vector (Promega Corp., Madison, Wis.).

Probe preparation: The 2.2 kb partial cDNA was digested with PstI to produce a 1.2 kb fragment DNA probe. A sample (25 ng) of the fragment was labeled with $[^{32}P]dCTP$, using the random sequence nanonucleotide REDIPRIME™ DNA labeling system (Amersham Pharmacia Biotech AB, Buckinghamshire, England).

Preparation of genomic DNA plasmid library: An *A. niger* B1 genomic library was constructed in the pYEAUra3 yeast/*E. coli* shuttle vector (Clontech Lab. Inc. Palo Alto, Calif.). *A. niger* B1 was grown in liquid culture as described above, the mycelium harvested following 48 hours of growth, frozen in liquid nitrogen and grounded. The mycelium ground was used to produce genomic DNA by the CTAB method of Murray and Thompson (29). The library was constructed from partially digested Sau3A genomic DNA, cloned into the BamHI site of the pYEUra3 yeast shuttle vector (Clontech Lab. Inc. Palo Alto, Calif.). pYEAUra3 yeast/*E. coli* shuttle vector was digested with BamHI and dephosphorylated with CIP to prevent self ligation. The partially digested genomic DNA was cloned into the shuttle vector with T4 ligase and used to transform TOP10 *E. coli* electro-competent cells, which were then plated on LB-agar containing ampicillin (50 µg/ml). A total of $4\times10^4$ colonies were grown on LB-agar plates, blotted to HYBOND-N™ membranes (Amersham Pharmacia Biotech AB, Buckinghamshire, England) and screened using the above described 1.2 kb probe. Positive clones were subcloned in pUC18 and sequenced (Biological Services, The Weizmann Institute of Science, Rehovot, Israel).

Figure 1B:
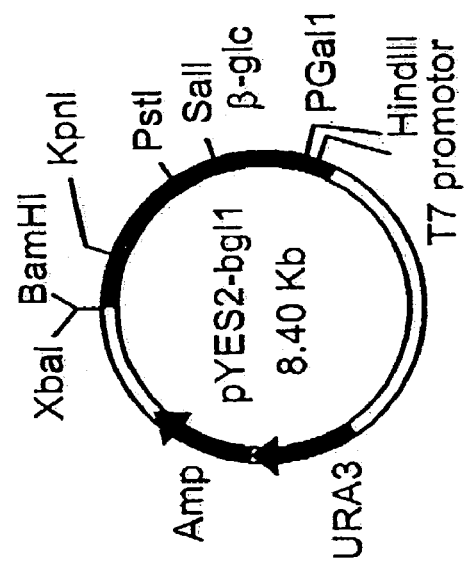
Figure 1A:
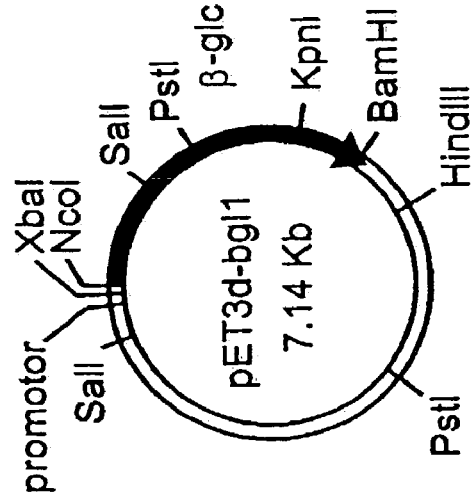

Expression of bgl1 cDNA in *E. coli*:

Two specific primers were designed according to the 5' and the 3' sequences, corresponding to the N-terminal and C-terminal region of the mature protein: sense primer: 5'-' (SEQ ID NO:8). Antisense primer: 5'-AAAGGATCCT-TAGTGAACAGTAGGCAGAGACGC-3' (SEQ ID NO:9). The isolated cDNA was digested with NcoI and BamHI and cloned into a pET3d expression vector (FIG. 1A, Novagen Inc., Madison, Wis.). Positive *E. coli* BL21(DE3) pLysS colonies, containing the bgl1 cDNA, were confirmed by enzyme restriction and sequence analysis. Recombinant BGL1 was expressed according to the manufacturer's protocol.

Expression of bgl1 cDNA in *Saccharomyces cerevisiae* and *Pichia pastoris*:

The pYES2 vector (Invitrogen Inc., San Diego, Calif.) was used to successfully clone the bgl1 cDNA gene into the HindIII/BamHI of pYES²-bgl1 plasmid (FIG. 1b), and transform *Saccharomyces cerevisiae* using the lithium acetate method (30). The BGL1 was expressed by inducing the Gall promoter according to the manufacturer's protocol. *Saccharomyces cerevisiae* strain INVSc2 (MATa, his3-D200, ura3-167) was used as the host *Pichia pastoris* strain GS115 (his4 mutant) was used as the host for shuttle and expression vector plasmid pHIL-S1 (Invitrogen Inc., San Diego, Calif.). The bgl1 cDNA was cloned into the EcoRI/BamHI sites of pHIL-S1, yielding the pHIL-S1-bgl1 expression and secretion vector (FIG. 1c). Expression in *P. pastoris* was carried out according to the manufacturer's protocol. Screening of β-glucosidase-expressing clones was facilitated by top-agar, containing 50 mg X-Glc, 30 ml methanol and 1% agar per liter. Blue color indicated a colony producing active β-glucosidase.

Western Blot Analysis:

Antibodies were produced from rabbit serum 36 days following a second injection of 100 μg purified protein and adjuvant (AniLab Biological Services, Tal-Sachar, Israel). High molecular weight ladder was from Sigma Chemical Inc. St. Louis, Mo. Western blot conditions were as described in reference 36.

Determination of the Stereochemical Course of Hydrolysis:

The method was essentially as described by Wong et al. (31). PNPGlc (10 μmols) was dissolved in 0.5 ml of 25 mM acetate buffer pH=3.5 in $D_2O$ in an NMR tube. β-Glucosidase was lyophilized and redissolved in 100 μl $D_2O$ (35 units/ml). The 1H-NMR spectrum of the substrate was recorded, enzyme added (10 μl), and spectra recorded at specified time intervals on a Bruker AMX400 at 25° C.

Inactivation and Reactivation Studies:

Pure *A. niger* β-Glucosidase enzyme (0.47 mg/ml) was incubated in the presence of various concentrations of 2-deoxy-2-fluoro-β-glucosyl fluoride (2FGlcF, 0.5-6 mM) in 30 mM citrate buffer pH=4.8 at 50° C. Residual enzyme activity was determined at different time intervals by addition of an aliquot (10 μl) of the inactivation mixture, to a solution containing citrate buffer (30 mM, pH=4.8), BSA (8 μg) and 2,4-dinitrophenyl β-D-glucopyranoside (DNPGlc, 0.625 mM, 830 μl). Release of DNP was determined spectrophotometrically by measuring the absorbance at 400 nm one minute after the addition of the substrate.

Reactivation rates were determined as follows: pure *A. niger* β-glucosidase (0.34 mg/ml) was preincubated with 2FGlcF (5 mM) for 15 min, after which the excess of the inactivator was diafiltered by 20-kDa nominal molecular mass cutoff centrifugal concentrators (Sartorius Inc., Goettingen, Germany). Samples of the purified, inactivated enzyme were incubated in the presence linamarin (0-16 mM) in citrate buffer (30 mM, pH=4.8) at 50° C. for 0, 10, 20 and 30 minutes, and the activity of each sample was determined using p-nitrophenyl β-D-glucopyranoside (pN-PGlc) as a substrate.

Expression of bgl1 cDNA in Tobacco Plants:

Genetic Constructs:

Bgl1 cDNA was cloned in pETB1 (37). pJD330 and pBINPlus (38) were used as an intermediate and binary vector, respectively. Cel1 signal sequence as well as 35S plus Ω fragment were retrieved from pB21, modified pBLUESCRIPT™ SK (39). *Nicotiana tabacum* cv. Samson was used as a model plant for gene transformation. Three gene constructs were employed (FIGS. 11a-c): (i) bgl1 without any signal peptide which served for cytoplasmic expression (FIG. 11a, plasmid pJDB1); (ii) bgl1 including a cell signal peptide at the N terminus for secretion into the apoplast (FIG. 11b, plasmid pJDCB1); and (iii) bgl1 including the cel1 signal peptide and the KDEL (SEQ ID NO:24) ER-retaining peptide at the C-terminus for accumulation in the ER (FIG. 11c, plasmid pJDCB1T).

To this end, bgl1 cDNA (2.5 kb) was released from pETB1 (37) with NcoI and BamHI and inserted into pJD330 between the 35S promoter Ω fragment and the nos terminator, eliminating the gus gene, resulting in plasmid pJDB1. Endoplasmic reticulum retaining signal tetrapeptide HDEL (SEQ ID NO:17) was synthesized and fused with bgl1 at the C-terminal in pJDB1 by a fidelity PCR reaction with the following pair of primers: Forward primer (23 mer), starting from nucleotide 1248 of bgl1 cDNA 5'-(1248)-CAGTGAC-CGTGGATGCGACAATG-(1270')-3' (SEQ ID NO:20); Reverse primer (40 mer), starting at nucleotide 2506 of bgl1 cDNA encoding also for the HDEL (SEQ ID NO:17) peptide 5'-(2506)-AGAGACGGATGACAAGTACTACT-TGAAATTGGGCCCAAAA-3' (SEQ ID NO:21). For pJDCB1T (35S Ω+Cel1+bgl1+HDEL, SEQ ID NO:17), the 35S Ω fragment of pJDB1 was replaced by a 35S Ω+Cel1 fragment digested from pB21 with BamHI and XbaI. For pJDCB1 (35S Ω+Cel1+bgl1), the fragment containing 35S Ω and Cel1 as well as part of bgl1 was cut from pJDCB1T with HindIII and NruI and ligated with the vector of pJDB1 digested with the same pair of restriction enzymes. The nucleotide sequence of all of the genetic constructs was confirmed by DNA sequencing.

Gene cassettes in the intermediate vectors of pJDB1, pJDCB1 and pJDCB1T were further isolated with HindIII and EcoRI and inserted into multiple cloning sites of the binary vector pBINPlus. Disarmed *Agrobacterium* LB4404 was transformed with pBINPlus containing bgl1 gene cassettes.

Tobacco Plant Transformation:

The young leaves of in vitro grown plantlets were excised and cut into 0.5 cm pieces and then immersed for 5 minutes in an overnight grown culture of *Agrobacterium*. After blotted with sterile Whatman filter paper, the infected leaves were co-cultured for 2 days with *Agrobacterium* on MS medium plus 2.0 mg/L of Zeatin and 0.1 mg/L of IAA as well as 0.35% (w/v) phytagel and then transferred to the same medium but with 300 mg/L kanamycin and 300 mg/L carbenicillin. Regenerates were then transferred to the rooting media, containing only MS salts, vitamins and the same antibiotics. Rooted plants were transferred to greenhouse after PCR screening.

Screening for Transgenic Plants:

DNA and protein of plants were extracted according to Nagy et al. (40). PCR verification of gene insertion into plant genome was done with the following pairs of primers, which cover the DNA fragment from position 1248 to the end of bgl1: 5'-CAGTGACCGTGGATGCGACAATG-3' (SEQ ID NO:22) and 5'-AAAGGATCCTTAGTGAACAGTAGGCA-GAGACGC-3' (SEQ ID NO:23).

Identifying Transgenic Plants Expressing BGL1 Protein and Activity:

Western blot (40) and SDS-PAGE activity gel staining (37) were employed to screen successful transgenic lines, using the purified *A. niger* BGL1 protein as positive controls and non-transgenic plant as negative control.

SPMI-GC/MS Analysis:

The effect of bgl1 on flavor compound evolution and composition was studied. Fresh leaves of transgenic plants and of wild type control plants were excised and ground in liquid nitrogen. Ice-cold extraction buffer, containing 10 mM EDTA, 4 mM DTT in 50 mM phosphate buffer, pH 4.3, was added in a ratio of 1:3 w/w. The mixture was then shaken for 0.5 hours. 0.75 ml of supernatant from each of the centrifuged mixtures was taken into a glass vial. All manipulations were at 4° C. Alter 9 hours of incubation at 37° C., the volatiles in the vial were analyzed according to Clark et al. (41) using a Saturn Varian 3800 SPMI-GC-MS apparatus, equipped with a DB-5 capillary column. The temperature of splitless injections was 250° C. and the transfer line was maintained at 280° C. Helium was used as a carrier gas. The oven was programmed as follows: 1 minute at 40° C. with gradually heating to 250° C. at a rate of 5° C./minute.

EXPERIMENTAL RESULTS

Figure 2:
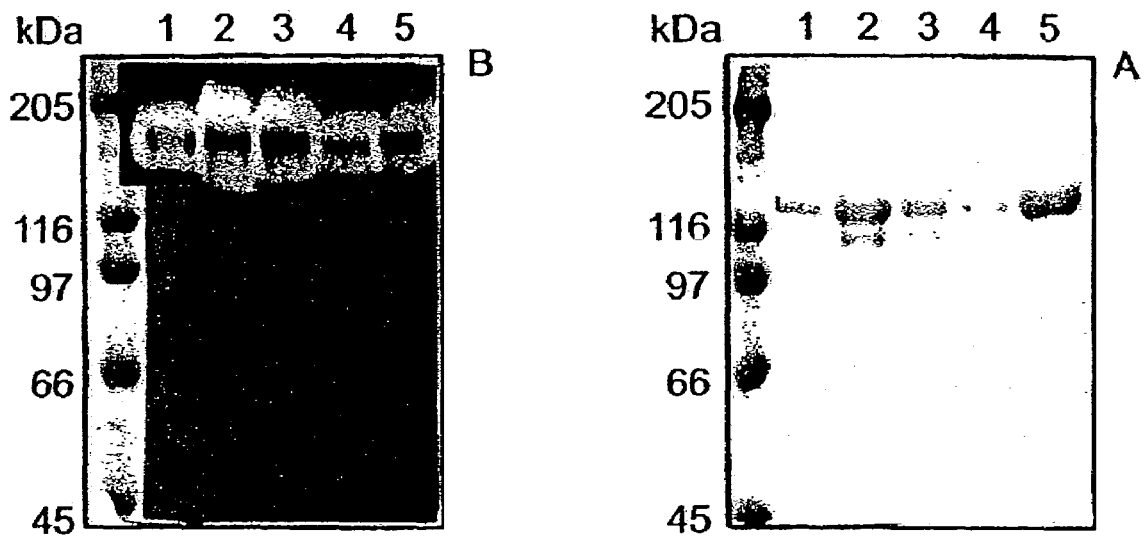
FIGS. 2a-b demonstrates SDS-PAGE analysis of active protein samples eluted from a MONO-Q™ (Amersham Biosciences Inc, Piscatawy, N.J.) anion exchange column, stained with coomassie blue (FIG. 2a), or β-glucosidase zymogram (FIG. 2b) using MUGlc as a substrate. Lanes (for both FIGS. 2a and 2b): 1—Electroeluted band of BGL1 from preparative PAGE-SDS gel stabs; 2, 3, 4, 5—acetone precipitates from MONO-Q™ (Amersham Biosciences Inc, Piscatawy, N.J.) anion exchange column separation of BGL1.
Figure 3:
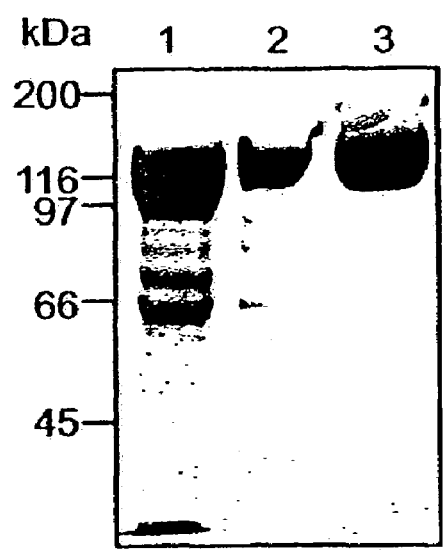
FIG. 3 demonstrates SDS-PAGE analysis of purified β-glucosidase by MONO-Q™ (Amersham Biosciences Inc, Piscatawy, N.J.) anion exchange and RESOURCE-S™ (Amersham Biosciences Inc, Piscatawy, N.J.) cation exchange columns. Lanes: 1—crude (27.5 µg protein); 2—active fraction after MONO-Q™ (Amersham Biosciences Inc, Piscatawy, N.J.) anion exchange MONO Q™ (7 µg protein); and 3—active fraction after RESOURCE-S™ (Amersham Biosciences Inc, Piscatawy, N.J.) cation exchange column (10 µg protein).
Figure 4:
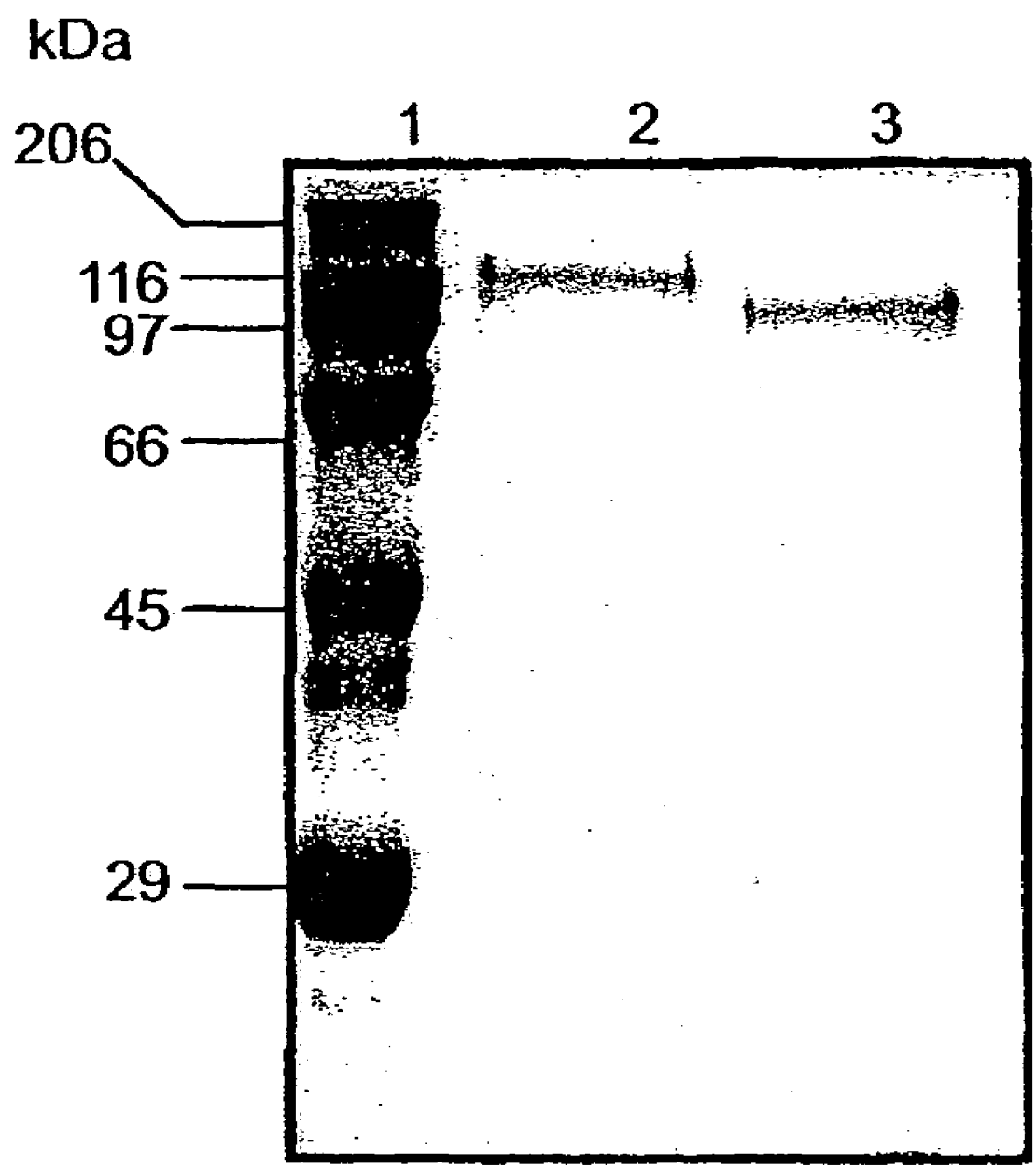
FIG. 4 demonstrates SDS-PAGE analysis of β-glucosidase deglycosylated by N-glycosidase-F. Lanes: 1—molecular weight marker; 2—native β-glucosidase; and 3—deglycosylated protein.

Purification of Wild Type *A. niger* β-glucosidase:

*A. niger* β-glucosidase enzyme preparation was purified by MONO-Q™ (Amersham Biosciences Inc, Piasctawy, N.J.) FPLC. Active protein samples eluted from the MONO-Q™ (Amersham Biosciences Inc, Piscatawy, N.J.) anion exchange column were separated on a 10% SDS-PAGE gel, stained with coomassie blue, and incubated in the presence of MUGlc to demonstrate activity of the enzyme. At this stage of purification, a discrete band, having an apparent molecular mass of approximately 160 kDa and β-glucosidase activity could be detected (FIG. 2b, lanes 1-5: 1—electroeluted band of BGL1 from preparative PAGE-SDS gel stabs; 2-5—acetone precipitates from MONO-Q™ (Amersham Biosciences Inc, Piscatawy, N.J.) anion exchange separation of BGL1). However, the apparent mass of the denatured enzyme (boiled for 10 min in the presence of β-mercaptoethanol), was shown to be 120 kDa on 10% SDS-PAGE (FIG. 2a). The enzyme was designated BGL1 was further purified to homogeneity on a RESOURCE-S™ (Amersham Biosciences Inc, Piscatawy, N.J.) cation exchange column (FIG. 3). Deglycosylation of *A. niger* β-glucosidase was performed by N-glycosidase-F. As demonstrated in FIG. 4, SDS-PAGE analysis indicated that approximately 20 kDa of the *A. niger* β-glucosidase mass can be attributed to N-linked carbohydrates.

Proteolysis and N-Terminal Sequences of BGL1:

Partial enzymatic proteolysis with *Staphylococcus aureus* V8 protease of purified BGL1 was conducted. The undigested protein and cleavage products were separated by SDS-PAGE, followed by electroblotting onto PVDF membranes and determination of the N-terminal sequence of the native protein and two of the cleavage products. Amino acid sequences obtained were as follows:

N-terminal native protein: Asp-Glu-Leu-Ala-Tyr-Ser-Pro-Pro-Tyr-Tyr-Pro-Ser-Pro-Trp-Ala-Asn-Gly-Gln-Gly-Asp (SEQ ID NO:10). Underlined portion represents SEQ ID NO:4.

Internal cleavage product—E1 polypeptide: Val-Leu-Lys-His-Lys-Asn-Gly-Val-Phe-Thr-Ala-Thr-Asp-Asn-Trp-Ala-Ile-Asp-Gln-Ile-Glu-Ala-Leu-Ala-Lys (SEQ ID NO: 11).

Internal cleavage product—E2 polypeptide: Gly-Ala-Thr-Asp-Gly-Ser-Ala-Gln-Pro-Ile-Leu-Pro-Ala-Gly-Gly-Gly-Pro-Gly-Gly-Asn-Pro (SEQ ID NO:12). Underlined portion represents SEQ ID NO:6.

FastA analysis (32) indicated that the N-terminal sequence, as well as the internal sequences, have sequence similarity with sequences of β-glucosidase from the yeast *Saccharomycopsis fibuligera* which belonging to Family 3 of the glycosyl hydrolases.

Isolation and Characterization of BGL1 cDNA and Genomic DNA:

In order to clone the *A. niger* β-glucosidase gene, degenerate primers were designed according to the sequence of digest fragments of the polypeptide. These oligonucleotides were used to amplify a cDNA fragment of the β-glucosidase gene by RT-PCR. A 1.2 kb probe was excised from the resultant 2.2 kb amplification product and was used to screen a genomic library, constructed in pYEUra3 yeast/*E. coli* shuttle vector. Positive clones were successfully subcloned and sequenced, resulting in full length bgl1 genomic sequence (SEQ ID NO:3, FIG. 5a). Amplification primers were then generated, according to the genomic DNA sequence, corresponding to the N- and C-terminal of the mature protein. RT-PCR was thereafter used for amplifying the full length β-glucosidase cDNA sequence (SEQ ID NO:1, FIG. 5a, GenBank Accession No. AJ132386). The cDNA sequence perfectly matched the DNA sequence of the combined exons. The open reading frame was found to encode a polypeptide with a predicted molecular weight of 92 kDa. The gene includes 7 exons intercepted by 6 introns (FIG. 5b). Analysis of the DNA sequence upstream to the sequence encoding for the mature protein revealed a putative leader sequence, intercepted by an 82 bp intron.

Production of rBGL1 in *E. coli*:

Recombinant BGL1 was overexpressed in *E. coli*. No apparent β-glucosidase activity could be detected in the *E. coli* extracts, however SDS-PAGE analysis revealed a relatively intense protein band expressed at the expected molecular weight Western blot analysis using rabbit polyclonal anti-native BGL1 antibodies (AniLab Biological Services, Tal-Sachar, Israel), positively identified the 90 kDa protein band (not shown). Further analysis revealed that the protein was accumulated in inclusion bodies. Several refolding experiments were conducted, however, these efforts to produce active protein from *E. coli* failed (not shown).

Figure 6:
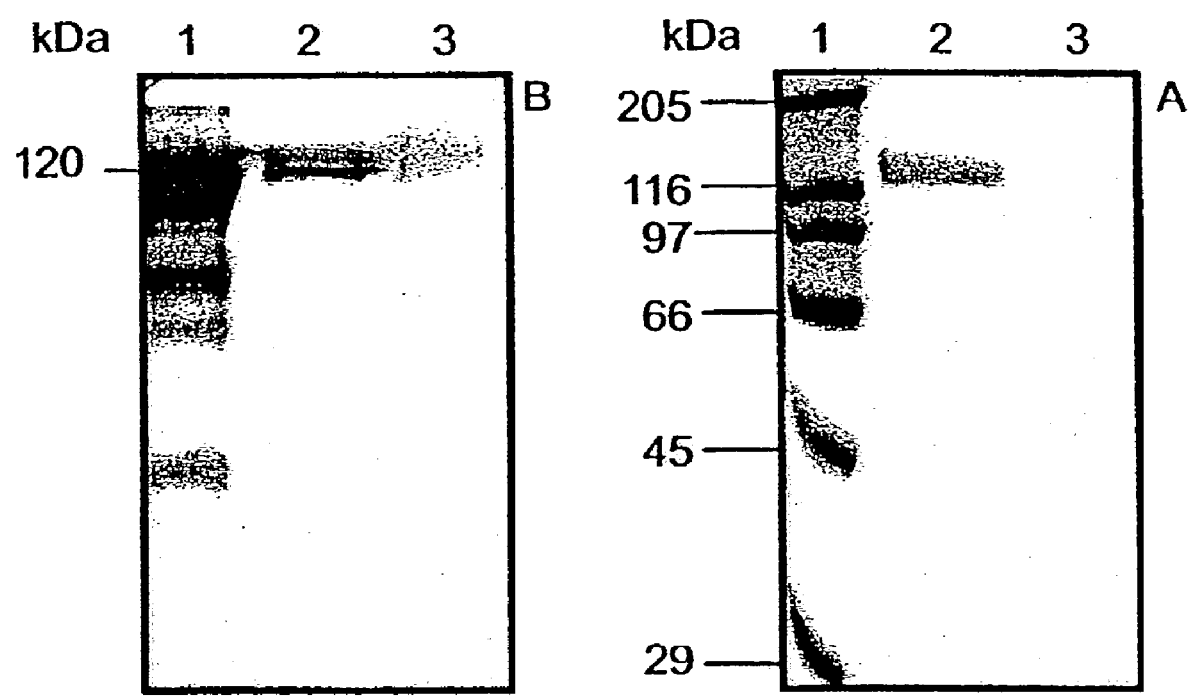
FIG. 6a demonstrates a Western blot analysis of recombinant BGL1 expressed in S. cerevisiae. Lanes: 1—native BGL1 (positive control); 2—total protein extract of S. cerevisiae expressing recombinant BGL1; 3—total protein extract of S. cerevisiae without the bgl1 expression vector (negative control).
FIG. 6b demonstrates a Western blot analysis of recombinant BGL1 secreted from P. pastoris. Lanes: 1—molecular weight marker; 2—medium supernatant of P. pastoris expressing recombinant BGL1; 3—medium supernatant of P. pastoris host without the vector (negative control).

Expression of Recombinant BGL1 in *S. cerevisiae* and *P. Pastoris*:

Recombinant BGL1 was successfully expressed both in *S. cerevisiae* and *P. pastoris*. In *S. cerevisiae* a relatively low level of expression was found. The recombinant protein was detected by a Western blot analysis (FIG. 6a). The total protein extract of *S. cerevisiae* expressing bgl1 cDNA had a β-glucosidase activity of 1.9 units/mg protein. No β-glucosidase activity was detected in control *S. cerevisiae*, transformed with vector only, under the same assay conditions. However, no protein band corresponding to recombinant BGL1 could be detected by coomassie blue staining. *P. pastoris* transformed with bgl1 secreted relatively high levels of recombinant BGL1 to the medium (about 0.5 g/l) appearing as an almost pure protein in the culture supernatant (FIG. 6b). This recombinant enzyme was highly active (124 units/mg protein) and without further purification, yielded specific activity similar to that of the pure native enzyme.

Figure 7:
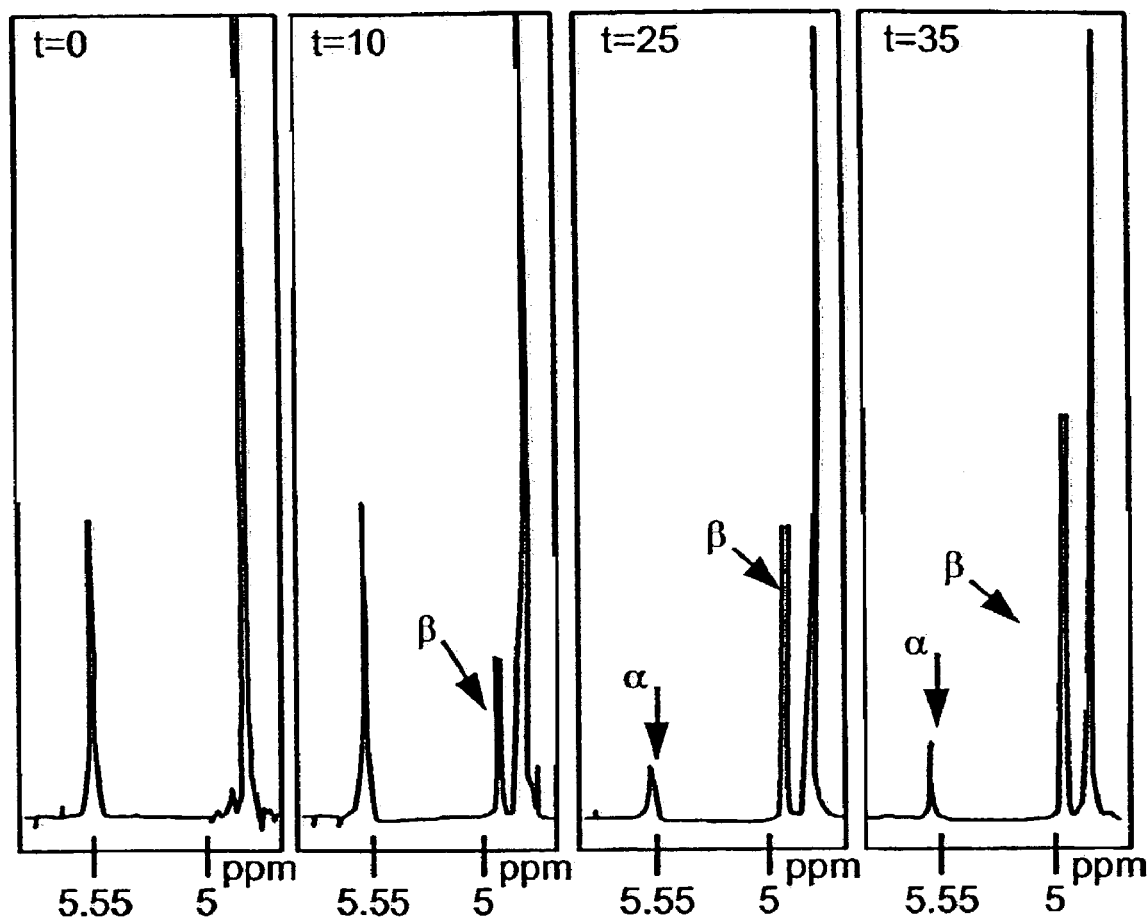
FIG. 7 demonstrates proton-NMR spectra, illustrating the stereochemical course of pNPGlc hydrolysis by A. niger β-glucosidase. Spectra are for the anomeric proton region of the substrate at different time intervals relative to addition of the enzyme.

1H-NMR Determination of Stereochemical Outcome:

1H-NMR spectra of a reaction mixture containing pNPGlc and BGL1 revealed that the beta anomer of glucose was formed first (H-1=4.95 ppm), with delayed appearance of the alpha anomer (H-1 5.59 ppm), the consequence of mutarotation (FIG. 7). BGL1 is indeed, therefore, a retaining glycosidase, as has been observed for other family members (33, 34).

Figure 8:
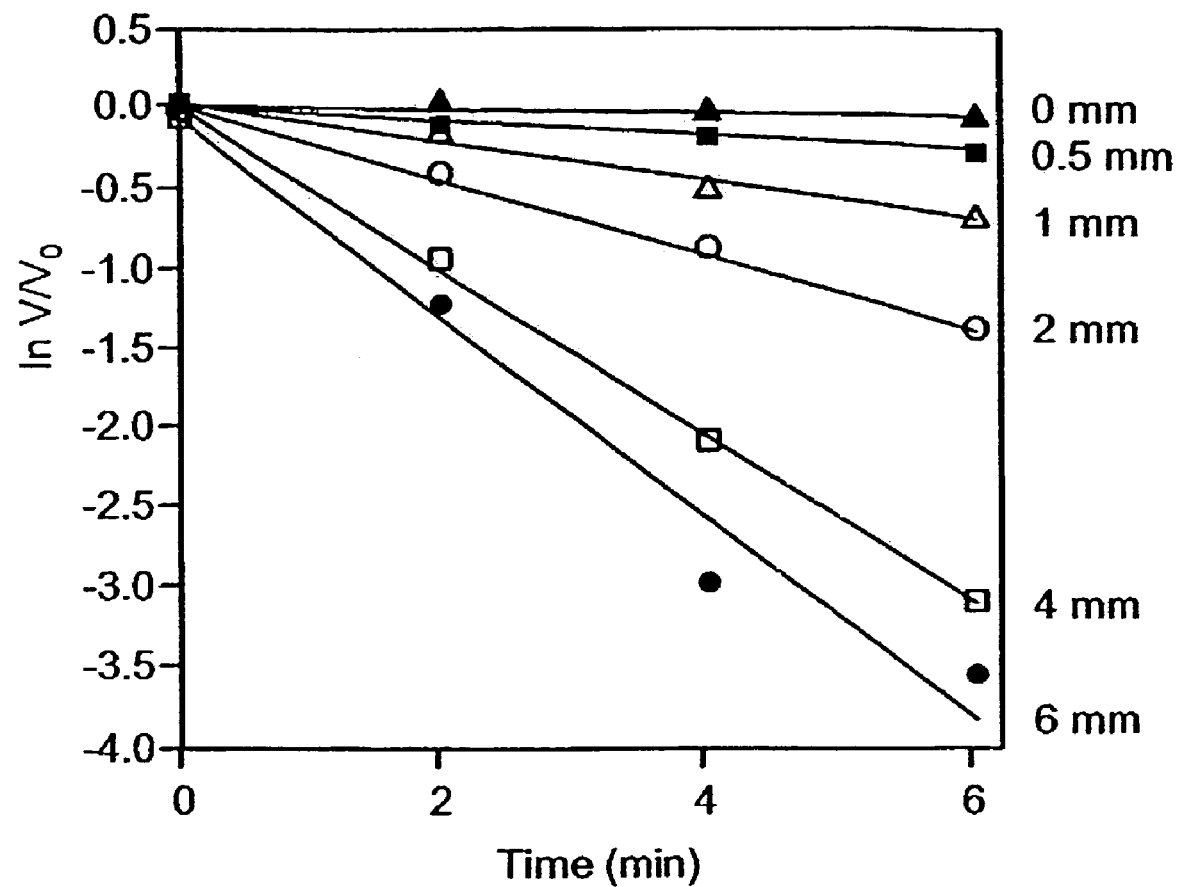
FIG. 8 demonstrates inactivation of recombinant BGL1 by 2FGlcF. Pure enzyme was incubated in the presence of various concentrations of the inactivator, and residual enzyme activity was determined at different time intervals. Residual activity is presented, semilogarithmically, versus time, in the presence of the indicated concentrations of inactivator.

Inactivation and Reactivation of *A. niger* β-Glucosidase:

Enzyme was incubated in the presence of various concentrations of 2FGlcF and residual enzyme activity was monitored at different time intervals. Enzyme activity decreased in a time-dependent manner, according to pseudo-first order kinetics, allowing the determination of pseudo-first order rate constants: $K_i$=4.5 min$^{-1}$ and $K_I$=35.4 mM, for inactivation at each inactivator concentration (0, 0.5, 1, 2, 4, and 6 mM, FIG. 8).

Figure 9:
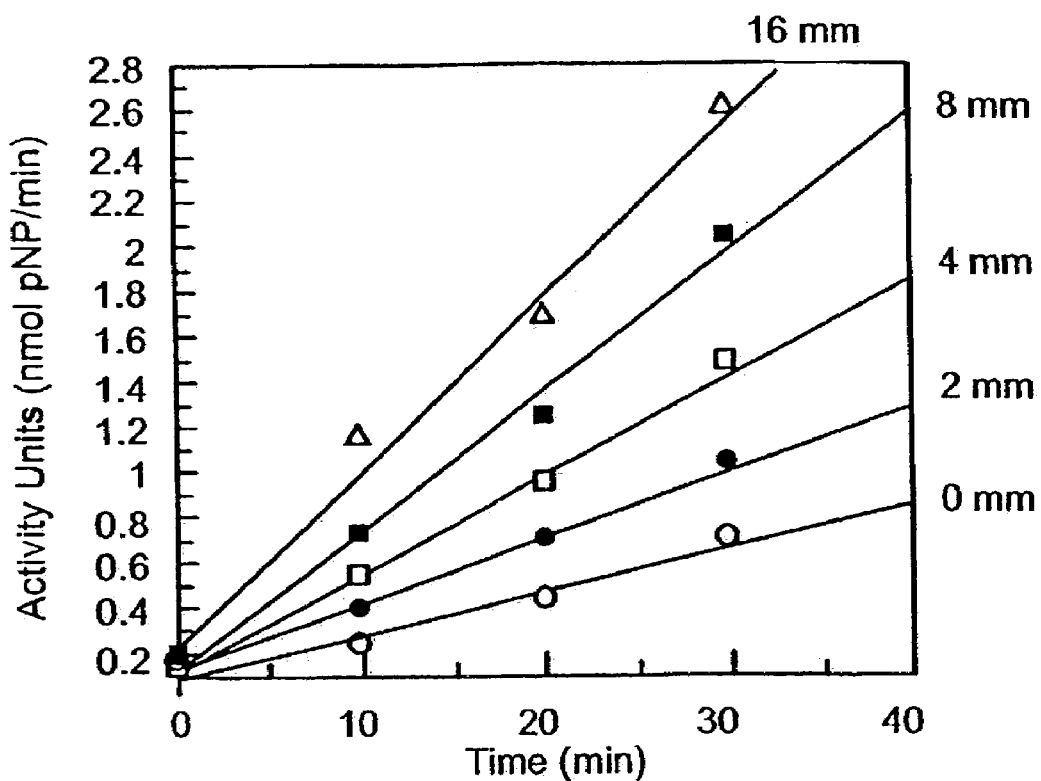
FIG. 9 demonstrates reactivation of 2-deoxy-2-fluoroglucosyl-recombinant BGL1 by linamarin. Activity is plotted versus incubation time in the presence of the indicated concentrations of linamarin.

Rates of reactivation of 2-deoxy-2-fluoroglucosyl-BGL1 were determined in the presence of different concentrations of linamarin by monitoring activity regain after 0, 10, 20 and 30 min (FIG. 9). The regain of activity followed a first order process at each linamarin concentration.

Thermal Stability of *A. niger* β-Glucosidase:

Thermal stability of the recombinant enzyme was evaluated at different temperatures, presented as percent enzymatic activity relative to an enzyme solution kept at 4° C.

Figure 10:
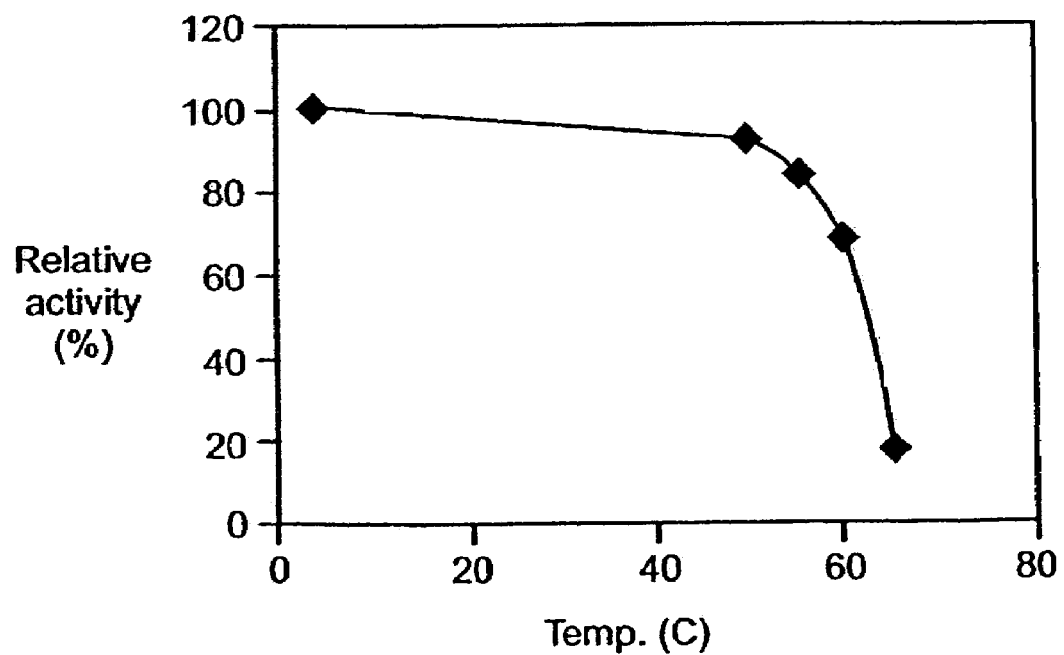
FIG. 10 demonstrates the stability of recombinant A. niger β-glucosidase at various temperatures. Activity is calculated as percent of a recombinant enzyme solution kept at 4° C.

Results obtained are summarized in Table 2 and illustrated in FIG. 10. The purified enzyme exhibits high thermal stability, as majority (above 50%) of the activity is maintained at a temperature ranging from 4-60° C.

TABLE 2

| Temp. ° C. | % activity |
|---|---|
| 4 | 100 |
| 50 | 91.5 |
| 55 | 83.5 |
| 60 | 68 |
| 65 | 17.8 |

Figure 14:
FIG. 14 show activity gel analysis of transgenic tobacco plant extracts in SDS-PAGE incubated with MUGlu. WT—non-transgenic control plant. CB10 and CB11—two independent lines of transgenic plants expressing BGL1 fused to Cel1 signal peptide (without HDEL, SEQ ID NO:17). CBT3, CBT8 and CBT15—independent lines of transgenic plants expressing BGL1 fused to Cel1 signal peptide at the N terminus and HDEL, SEQ ID NO:17 ER retaining peptide at the C terminus. B1 and B34—transgenic plant expressing BGL1 without signal peptide or HDEL, SEQ ID NO:17 ER retaining peptide and which were positive for BGL1 protein in Western blot analysis. An Glu—control A. niger native beta-glucosidase.
Figure 15:
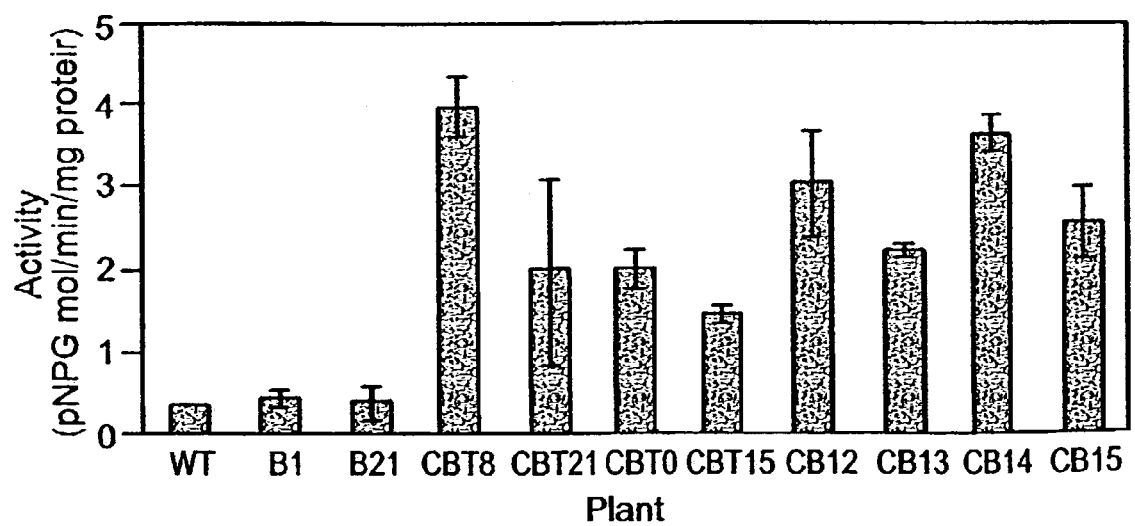
FIG. 15 demonstrates level of BGL1 activity in different transgenic plants. WT—non-transgenic control plant. B1 and B21—transgenic plants expressing BGL1 without signal peptide or HDEL, SEQ ID NO:17 ER retaining peptide and which were positive for BGL1 in Western blot analysis. CBT8, CBT21, CBT0 and CBT15—independent lines of transgenic plants expressing BGL1 fused to Cel1 signal peptide at the N terminus and HDEL, SEQ ID NO:17 ER retaining peptide at the C terminus. CB12, CB13, CB14 and CB15—four independent lines of transgenic plants expressing BGL1 fused to Cel1 signal peptide (without HDEL, SEQ ID NO:17).

Expression of BGL1 in Tobacco Plants:

Agrobacterium mediated leaf disc transformation resulted in transgenic tobacco plants as was proved by PCR (FIG. 12) for the presence of the transgene, Western blotting (FIGS. 13a-b) for presence of the protein and activity assays (FIGS. 14 and 15) for presence of protein activity. Table 3 below summarizes the results.

TABLE 3

| Gene construct | BGL1 | Cell + BGL1 + HDEL, SEQ ID NO:17 | Cell + BGL1 |
|---|---|---|---|
| Number of Regenerates | 33 | 14 | 27 |
| PCR positive | 29 | 9 | 23 |
| Western Blot positive | 4 | 9 | 18 |
| Activity gel positive | 0 | 9 | 18 |

Of the 29 PCR positive regenerates transformed with cDNA encoding BGL1, which fails to encode a signal peptide, only in 4 the BGL1 protein was detectable via Western blotting, however no BGL1 activity was measurable in any of which. The BGL1 was found smaller in molecular weight compared to wild type *A. niger* beta-glucosidase and of processed recombinant BGL1 containing a signal peptide. Its apparent size of about 95 kDa is very close to 92 kDa which is the calculated molecular weight of the un-glycosylated *A. niger* beta-glucosidase. This result coincides with the fact that a protein with no signal peptide is expected to be released from the ribosomes and remain in the cytoplast (42) un-glycosylated, as protein glycosylation is conducted in the lumen of the endoplasmic reticulum (43).

Of the 9 PCR positive regenerates transformed with a cDNA encoding the BGL1 and a Cel1 signal peptide and in addition encodes the HDEL, SEQ ID NO:17 ER retaining peptide, all plants expressed detectable amounts of BGL1 protein and activity.

Of the 23 PCR positive regenerates transformed with a cDNA which encodes the BGL1 protein and the Cel1 signal peptide but not the HDEL, SEQ ID NO:17 ER retaining peptide, 18 plants expressed detectable amounts of BGL1 protein and activity.

The Effect of BGL1 on Flavor Compound Evolution and Composition in Transgenic Tobacco Plants:

Extracts of transgenic plants (CB14 and CBT21 containing similar BGL1 activity, see FIG. 15) were incubated for 9 hours at 37° C., and flavor compounds were analyzed by SPMI-GC/MS. The results, which are summarized in Table 4 below, show that with the exception of oleyl alcohol, the concentration of different flavor compounds is increased in transgenic plants expressing active BGL1 compared with the control. Furthermore, it seems that compartmentalization of BGL1 in the ER (or for that matter, any other subcellular organelle), rather then its secretion to the apoplast, results in higher release of flavor compounds. It is likely that this is resulted from the localization many flavor compounds in the apoplast, thus, secretion of BGL1 to the apoplast cause in vivo release of flavor compounds, while compartmentalization of BGL1 in the ER results in release of flavor compounds only in the event of cell disruption and decompartmentalization.

TABLE 4

| Retention Time (minutes) | Scan | Name | CB14 | CBT 21 |
|---|---|---|---|---|
| 3.917 | 419 | Hexanal | –[a] | – |
| 4.749 | 508 | 3-methyl-pentanoic acid | – | – |
| 4.863 | 520 | 2-Hexenal | – | +[b] |
| 5.167 | 552 | ? | – | + |
| 6.564 | 702 | 1-Heptanol | – | – |
| 7.1 | 752 | ? | + | ++[d] |
| 8.085 | 865 | 2-ethyl-1-pexanol | – | + |
| 8.132 | 870 | Limonene | ++ | + |
| 8.194 | 877 | 2-methyl-phenol | – | + |
| 10.653 | 1139 | Menthol | + | + |
| 11.757 | 1258 | Nerol | – | + |
| 12.039 | 1288 | 6-Quinolinol | – | + |
| 12.1 | 1294 | 2-butyl-1-octanol | – | + |
| 13.0 | 1458 | ? | – | + |
| 13.7 | 1466 | ? | – | + |
| 14.091 | 1507 | Vitispirane | – | + |
| 14.094 | 1516 | 4-[2,6,6-trimethyl-1-cyclohexen-1-yl]3-Buten-1-one | + | ++ |
| 15.985 | 1710 | ? | – | – |
| 19.327 | 2069 | Oleyl alcohol | ––[c] | –– |

CB14 - transgenic plant containing Cel1 signal peptide + BGL1;
CBT 21 - transgenic plant containing Cel1 signal peptide + BGL1 + HDEL, SEQ ID NO:17 ER retaining peptide.
[a]"–" means no significant difference in concentration compared with wild type.
[b]"+" means significant increase compared with the wild type.
[c]"––" means significant decrease compared with the wild type.
[d]"++" means significant increase compared with a respective mark "+".
? - unknown compound.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by GenBank accession numbers mentioned in this specification are herein incorporated in their entirety by reference into the specification, to the same extent as if each individual publication, patent, patent application or sequence was specifically and individually indicated to be incorporated herein by reference. In addition, citation or identification of any reference in this application shall not be construed as an admission that such reference is available as prior art to the present invention.

REFERENCES

1. Bause, E., and Legler, G. (1974) Hoppe-Seyler's Z. Physiol. Chem. 355, 438-442.
2. Beguin, P., and Aubert, J. P. (1994) FEMS Microbiol. Rev. 13, 25-58.
3. Rombouts, F. M. and Pilnik, W. (1978), Proc. Biochem. 8, 9-13.
4. Sternberg, D., Vijayakumar, P. and Reese, E. T. (1977), Can. J. Microbiol. 23, 139-147.
5. Woodward, J. and Wiseman, A. (1982), Enz. Microbiol. Technol. 4, 73-79.

6. Kerns, G., Dalchow, E., Klappach, G. and Meyer, D. (1986), Acta. Biotechnol. 6(4), 355-359.
7. Shoseyov, O., Bravdo, B., Ikan, R. and Chet, I. (1988), Phytochem. 27(7), 1973-1976.
8. Shoseyov, O., Bravdo, B., Siegel, D., Goldman, A., Cohen, S. and Shoseyov, L. (1990), J. Agric. Food. Chem. 39, 1387-1390.
9. Dekker, R. F. H. (1986), Biotechnol. Bioengin. 26, 1438-1442.
10. Kitpreechavanich, V. M., Hayashi, M. and Nagai, S. (1986), Agric. Biol. Chem. 50, 1703-1711.
11. Yeoh, H. H., Tan, T. K. and Koh, S. K. (1986), Appl. Microbiol. Biotechnol. 25, 25-28.
12. Crouzet, J. and Chassagne, D. (1999) in Naturally Occurring Glycosides (Ikan. R., ed.) pp. 225-274, Wiley Press.
13. Prade, H., L. F. Mackenzie and S. G. Withers (1998) *Carbohyd. Res.* 305, 371-381.
14. Zarevucka M., Vacek, M., Wimmer, Z., Demnerova, K. and Mackova, M. (1998) *Chirality* 10, 676-68.
15. Yi, Q., Sarney, D. B., Khan, J. A. and Vulfson, E. N. (1998) *Biotechnol. Bioeng.* 60, 385-390.
16. McCleary, B. V. and Harrington, J. (1988), Methods Enzymology, 160, 575-583.
17. Watanabe, T., Sato, T., Yoshioka, S., Koshijima, T. and Kuwahara, M. (1992), Eur. J. Biochem. 209, 651-659.
18. Unno, T., Ide, K., Yazaki, T., Tanaka, Y., Nakakuki, T. and Okada, G. (1993), Biosci. Biotech. Biochem. 57(12), 2172-2173.
19. Le Traon, M. M. P., and Pellerin P., (1998) Enz. Micro. Technol., 22 (5) 374-382.
20. Penttila, M. E., Nevalainen, H. K. M., Raynal, A., and Knowles, J. K. C., (1984), Mol. Gen. Genet. 194, 494-499.
21. Henrissat, B., and Bairoch, A. (1996) Biochem. J. Lett. 316, 695-696
22. Sinnott, M. L. (1990) Chem. Rev. 90, 1171-1202.
23. McCarter, J., and Withers, S. G. (1994) Curr. Opin. Struct. Biol. 4, 885-892.
24. Davies, G., Sinnott, M. L., and Withers, S. G. (1998) in CBiological Catalysis (Sinnott, M. L., ed.) Vol. 1, pp. 119-208, Academic Press.
25. Legler, G., Roeser, K. R., and Illig, H. K. (1979) Eur. J. Biochem. 101, 85-92.
26. Roeser, K. R., and Legler, G. (1981) Biochem. Biophys. Acta. 657, 321-333.
27. Legler, G., Sinnott, M. L., and Withers, S. G. (1980) J. Chem. Soc., Perkin Trans. 11, 1376-1383.
28. Cleveland, D. W., Fischer, S. G., Kirschner, M. W. and Laemmli, U.K. (1977), J. Biol. Chem. 252(3), 1102-1106.
29. Murray, M. G. and Thompson, W. F. (1980), Nucl. Acids Res. 8, 4321-4325.
30. Ito, H., Fukuda, Y., Murata, K. and Kimura, A. (1983), J. Bacteriol. 153(1), 163-168.
31. Wong, A. W., He, S., Grubb, J. H., Sly, W. S. and Withers S. G. (1998), J. Biol. Chem. 273, 34057-34062.
32. Lipman, D. J. and Pearson, W. R. (1985) Science, 227, 1435-1441.
33. Legler, G. (1968) Hoppe-Zeyler's Z. Physiol. Chem. 349, 767-774.
34. Hrmova, M. and Fincher, G. B. (1996) J. Biol. Chem. 271, 5277-5286.
35. Iwashita K., Todoroki, M., Kimura, H., Shimoi, H. and Ito, K. (1998) Biosci. Biotechnol. and Biochem. 62 (10), 1938-1946.
36. Rlow E. and Lane D. (1988) Antibodies, a laboratory manual. Cold Spring Harbor Laboratory, Cold Spring Harbor, N.Y.
37. Siegel D., Marton I., Dekel M., Bravdo B. A., He S. M., Wither S. G., Shoseyov O., 2000, Cloning, expression, characterization, and nucleophile identification of family 3, *Aspergillus niger* beta-glucosidase. J. Biol. Chem. 275(7), 4973-4980.
38. Engelen F. A. V., Molthoff J. W., Conner A. J., Nap J. P., Pereira A and Stiekema W., 1995, pBINPLUS: an improved plant transformation vector based on pBIN19. Transgenic Res. 4, 288-290.
39. Shani Z., Dekel M., Tsabary G., Shoseyov., 1997, Cloning and characterization of elongation specific endo-1,4-beta-glucanase (Cel1) from *Arabidopsis thialiana*, Plant Molecular Biol. 34: 837-842.
40. Nagy F., Kay S. A. K., Chua N. H., 1989, Analysis of gene expression in transgenic plants. In Plant Molecular Biology: manual edited by Gelvin et al., Kluwer Academic Publishers.
41. Clark T. J., Bunch J. E., 1997, Qualitative and quantitative analysis of flavor additives on tobacco products using SPME-GC-Mass Spectroscopy. J. Aagric. Food Chem. 45 (3), 844-849.
42. Lewin B., 1994, The apparatus for protein localization, In Gene V, Oxford University Press. Pp: 279-314.
43. Prodi J. A., 2000, The role of N-oligosaccharide endoplasmic reticulum processing reactions in glycoprotein folding and degradation. Biochem. J., 348, 1-13.

What is claimed is:

1. A method of producing a recombinant β-glucosidase expressing cell, the method comprising the step of introducing, in an expressible form a nucleic acid construct into a host cell, said nucleic acid construct comprising a polynucleotide encoding a polypeptide having the amino acid sequence as set forth in SEQ ID NO:2, said polypeptide having a β-glucosidase catalytic activity, said cell having greater β-glucosidase catalytic activity as compared to β-glucosidase catalytic activity of a host cell not expressing said recombinant β-glucosidase.

2. The method of claim 1, wherein said host cell is selected from the group consisting of a prokaryotic cell and a eukaryotic cell.

3. The method of claim 2, wherein said eukaryotic cell is selected from the group consisting of a yeast cell, a fungous cell, a plant cell and an animal cell.

4. The method of claim 1, wherein said polynucleotide is as set forth in SEQ ID NO: 1.

5. A method of producing an aroma spreading plant, the method comprising the step of expressing in the plant a nucleic acid construct which comprises a polynucleotide encoding a polypeptide having the amino acid sequence as set forth in SEQ ID NO:2, said polypeptide having a β-glucosidase catalytic activity, said plant having greater β-glucosidase catalytic activity as compared to β-glucosidase catalytic activity of a plant not expressing said nucleic acid construct, thereby increasing aroma spread from the plant.

6. The method of claim 5, wherein expressing said nucleic acid construct is limited to a tissue selected from the group consisting of fruit, seed, root, stem, pollen and leaves.

7. The method of claim 5, wherein said polynucleotide is as set forth in SEQ ID NO: 1.

* * * * *